(12) United States Patent
Karpishin et al.

(10) Patent No.: US 7,563,890 B2
(45) Date of Patent: *Jul. 21, 2009

(54) AMPHIPHILIC MOLECULAR MODULES AND CONSTRUCTS BASED THEREON

(75) Inventors: Timothy B. Karpishin, Castro Valley, CA (US); Josh Kriesel, San Francisco, CA (US); Grant Merrill, San Francisco, CA (US); Donald B. Bivin, Oakland, CA (US); Thomas H. Smith, San Carlos, CA (US); Martin Stuart Edelstein, Foster City, CA (US)

(73) Assignee: Covalent Partners, LLC, Hayward, CA (US)

( * ) Notice: Subject to any disclaimer, the term of this patent is extended or adjusted under 35 U.S.C. 154(b) by 260 days.

This patent is subject to a terminal disclaimer.

(21) Appl. No.: 11/207,383

(22) Filed: Aug. 18, 2005

(65) Prior Publication Data

US 2006/0270846 A1  Nov. 30, 2006

Related U.S. Application Data

(63) Continuation of application No. 10/071,377, filed on Feb. 7, 2002, now abandoned.

(51) Int. Cl.
*C07D 487/00* (2006.01)
*C07D 491/00* (2006.01)
*C07D 513/00* (2006.01)

(52) U.S. Cl. ................................... 540/476

(58) Field of Classification Search ............... None
See application file for complete search history.

(56) References Cited

U.S. PATENT DOCUMENTS

| | | | |
|---|---|---|---|
| 6,045,821 A | 4/2000 | Garrity et al. | |
| 7,368,564 B2 | 5/2008 | Whiteford et al. | |
| 2003/0199688 A1* | 10/2003 | Kriesel et al. | 540/454 |
| 2004/0106741 A1 | 6/2004 | Kriesel et al. | |
| 2004/0260085 A1* | 12/2004 | Kriesel et al. | 540/471 |
| 2006/0041077 A1* | 2/2006 | Kriesel et al. | 525/327.4 |
| 2006/0128680 A1* | 6/2006 | Kriesel et al. | 514/183 |

OTHER PUBLICATIONS

Korupoju et al. Chemical Communications, 1998, 1267-68.*
Gawrowski et al. Journal of Organic Chemistry, 2000, 65, 5768-73.*
International Search Report mailed Dec. 18, 2003, issued in co-pending PCT Application No. PCT/US03/03830.
International Search Report mailed Feb. 23, 2004, issued in co-pending PCT Application No. PCT/US03/03829.
International Search Report mailed Jul. 6, 2005, issued in co-pending PCT Application No. PCT/US03/027749.
Korupoju, et al., "New Optically Active Hexaaza Triphenolic Macrocycles: Synthesis, Molecular Structure and Crystal Packing Features," *Chem. Commun.* pp. 1267-1268 (1998).
Korupoju, et al., Formation of Dinuclear Macrocyclic and Mononuclear Acyclic Complexes of a New Trinucleating Hexaaza Triphenoiic Schiff Base Macrocycle: Structure and NLO Properties, *J. Chem. Soc. Dalton Trans.* pp. 2845-2852 (2000).

* cited by examiner

*Primary Examiner*—James O Wilson
*Assistant Examiner*—Noble Jarrell
(74) *Attorney, Agent, or Firm*—Finnegan, Henderson, Farabow, Garrett & Dunner, LLP

(57) ABSTRACT

Certain amphiphilic modules comprising 3-24 synthons are provided herein. Each synthon is independently selected from aryl, heteroaryl, alicyclic, and heteroalicyclic substituents, wherein each synthon selected is bonded to the next through a linker to form a closed ring that defines a nanopore. One or more lipophilic moieties and one or more hydrophilic moieties are bonded to one or more of the synthons, resulting in the formation of the desired amphiphilic modules. Those modules may be subsequently linked to one another to form two-dimensional close-packed planar arrays, referred to as nanomembranes. Nanomembranes may be useful in filtering certain ionic species from a solution. Selective passage of particular species is determined, in part, by the size of the module's nanopore and the nature of the lipophilic/hydrophobic species attached thereto. Also provided are methods of making and using amphiphilic modules and nanomembranes.

11 Claims, 15 Drawing Sheets

2A

4A

4B

5A

AMPHIPHILIC MOLECULAR MODULES AND CONSTRUCTS BASED THEREON

CROSS REFERENCE TO RELATED APPLICATION

This application is a continuation of U.S. patent application Ser. No. 10/071,377, filed on Feb. 7, 2002, now abandoned the contents of which is incorporated herein by reference in its entirety.

FIELD OF THE INVENTION

This invention is related to the fields of organic chemistry and nanotechnology. In particular, it relates to materials and methods for the construction of amphiphilic modules and the formation of nanomembranes, from the modules.

BACKGROUND OF THE INVENTON

In 1959, Richard Feynman addressed a meeting of the American Physical Society with a talk titled "There's Plenty of Room at the Bottom." Professor Feynman, drawing on his own fascination with biology ("Biological systems can be exceedingly small . . . but they are active; they manufacture substances, they walk around; . . . and they do all kind of marvelous things-all on a very small scale."), predicted that amazing feats of man-made miniaturization would be realized in the not too distant future.

Twenty-six years later, K. Eric Drexler wrote a book entitled "Engines of Creation" in which he described nanotechnology as "the knowledge and means for designing, fabricating and employing molecular scale devices by the manipulation and placement of individual atoms and molecules with precision on the atomic scale."

In 1990, Donald Eigler, working in the IBM Almaden Research Center, used the then recently developed scanning probe microscope (SPM) to manipulate 35 individual xenon atoms into the letters IBM on the surface of a crystal of nickel. Since that time a tremendous amount of effort has been, and continues to be, spent on devising practical applications for this new-found ability to work directly with the atom.

In organic chemistry, the quest has not been so much to work with individual atoms as to work with small groups of atoms—molecules—and use them to build, under totally controlled conditions, multimolecular architectures capable of performing, on a submicroscopic scale, functions normally reserved for large-scale constructs. For example, rotaxanes and polyrotaxanes, molecules that are interlocked but not chemically bound to one another, exhibit some mechanical characteristics—they act like micro-machines are being widely studied. Likewise, dendrimers, mono-dispersed macromolecules with a regular and highly branched three-dimensional architecture, also are receiving substantial attention, especially in the area of catalysis. Carbon nanotubes, isolated from the carbon soot on graphite electrodes, have elicited a tremendous amount of interest for a wide range of applications such as strength enhancing fillers for conventional polymers, fuel cell construction, electrical field emitters and quantum wires.

The use of biological processes is also being studied as an approach to the assembly of non-biological nano-devices. For example, in 1995, U.S. Pat. No. 5,468,851, entitled "Construction of Geometrical Objects from Poly-nucleotides," was issued to Seeman and Zhang. The inventors claimed the ability to produce " . . . almost any structure one can imagine . . . " starting with a double stranded polynucleotide segment having a loop at one end that contains a restriction site. The loop is cleaved at the restriction site, and another double stranded polynucleotide segment itself having a loop containing an endonuclease recognizable sequence different from that of the first segment, is ligated to the first segment at the cleavage site. The loop of the second segment is then cleaved and a third polynucleotide segment is ligated into the system. The process is continued until the desired structure is achieved.

The formation of monomolecular thick, selectively permeable membranes was described in 1997 by Hendel, et al., *JACS*, 1997, 119:6909-18. Hendel and his coworkers reported the synthesis of calix[6]arenes and their deposition as Langmuir-Blodgett films on a porous poly[1(trimethylsilyl)-1-propyne] substrate. They found that, when the calixarenes were positioned on the substrate such that individual calixarene molecules exactly spanned a pore in the substrate, a selectively permeable membrane was formed; i.e., nitrogen was found to pass through the membrane about 10,000 times more slowly than helium.

Another approach to the synthesis of molecular scale constructs was patented in 1999 by Michl, et al. (U.S. Pat. No. 5,876,830). Michl analogized his approach to the children's construction toy "TINKERTOY™" (Playskool, Inc., Pawtucket, R.I.). That is, Michl builds macromolecular structures by linking together complex molecular modules using connectors, spacers, binders, etc. The procedure requires adhering modules to a surface and then reacting connector groups on adjacent modules with molecular "rods" to form monomolecular grids or nets.

In 2001, an international patent application, WO 01/27028 A1, to Spencer and Allis and entitled "Design and Fabrication of Molecular Nanosystems," published. There, Spencer and Allis describe structural sub-units they term "synthons" which they claim can be used for the design and manufacture of molecular nanostructures, machines and devices. Their synthons are rigid polyhedral structures, namely closocarboranes, which were selected based on their synthetic availability and the fact that they exhibit the requisite substitutional control and structural diversity the inventors considered necessary creation of nano-scale constructs.

For a further review of the above and other areas of research in nanotechnology, see *Chemical Reviews*, 1999(7).

The present invention provides novel, extremely versatile molecular modules, methods for their synthesis and fabrication into nanoscale devices, in particular selectively permeable membranes.

SUMMARY OF THE INVENTION

Thus, in one aspect, the present invention relates to an amphiphilic module, comprising 3-24 synthons independently selected from the group consisting of aryl, heteroaryl, alicyclic and heteroalicyclic, provided at least one of the synthons is different from the others. The synthons are arranged such that a first synthon is bonded to a second synthon through a linker, the second synthon is bonded to a third synthon through a second linker, the third synthon is bonded to a fourth synthon, if four synthons are desired in the module, the fourth to a fifth, etc., until an nth synthon is bonded to its predecessor through an $(n-1)^{th}$ linker, where n is 4-24. The $n^{th}$ synthon is then bonded to the first synthon through an $n^{th}$ linker to form a closed ring of synthons There are also one or more lipophilic moieties bonded to one or more of the synthons and one or more hydrophilic moieties bonded to one or more of the synthons.

In an aspect of this invention, each synthon is independently selected from the group consisting of benzene, naphthalene, anthracene, phenylene, phenathracene, pyrene, triphenylene, phenanthrene, pyridine, pyrimidine, pyridazine, biphenyl, bipyridyl, cyclohexane, cyclohexene, decaline, piperidine, pyrrolidine, tetrahydropyran, tetrahydrothiane, 1,3-dioxane, 1,3-dithiane, 1,3-diazane, tetrahydrothiophene, tetrahydrofuran, pyrrole, cyclopentane, triptycene, adamantane, bicyclo[2.2.1]heptane, bicyclo[2.2.1]heptene, 7-azabicyclo[2.2.1]heptane, 1,3-diazabicyclo[2.2.1]heptane, bicyclo[2.2.2]octane, bicyclo[2.2.2]octene, bicyclo[3.3.0]octane, bicyclo[3.3.1]nonane, bicyclo[3.3.1)]nonene, bicyclo[4.2.2]decane or bicyclo[4.2.2]decene.

In a further aspect of this invention, the lipophilic moiety is selected from the group consisting of -(8C-28C)alkyl, —O(8C-28C)alkyl, —NH(8C-28C)alkyl, —OC(O)-(8C-28C)alkyl, —C(O)O-(8C-28C)alkyl, —NHC(O)-(8C-28C)alkyl, —C(O)NH-(8C-28C)alkyl, —CH=CH-(8C-28C)alkyl and —C≡C-(8C-28C)alkyl. The carbon atoms of the (8C-28C)alkyl group may be interrupted by one or more —S—, double bond, triple bond or —SiR'R"—groups, substituted with one or more fluorine atoms or any combination of these. R' and R" independently comprise (1C-18C)alkyl.

In a still further aspect of this invention, the hydrophilic moiety is selected from the group consisting of —OH, —OCH$_3$, —NH$_2$, —C≡N, —NO$_2$, —$^+$NRR'R", —SO$_3^-$, OPO$_2^{2-}$, —OC(O)CH=CH$_2$, —SO$_2$NH$_2$, SO$_2$NRR', OP(O)(OCH$_2$CH$_2$N$^+$RR'R")O$^-$, —C(O)OH, —C(O)O$^-$, guanidinium, aminate, pyridinium, —C(O)OCH$_3$, —C(O)OCH$_2$CH$_3$, —C(O)OCH=CH$_2$—, O(CH$_2$)$_y$C(O)NH$_2$, —O(CH$_2$CH$_2$O)$_z$R''' and

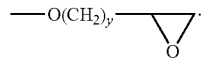

R, R' and R" are independently selected from the group consisting of hydrogen and (1C-4)alkyl, R''' is selected from the group consisting of hydrogen, —CH$_2$C(O)OH and —CH$_2$C(O)NH$_2$. In the preceding groups, y is 1-6 and z is 1-50.

In an aspect of this invention, each linker is independently selected from the group consisting of —O—, —S—, —NR$^{17}$—, —SS—, —CR$^{17}$R$^{18}$—, —CH(OH)—, —C(OH)R$^{17}$—CH$_2$NR$^{18}$—, —CH(OH)CH(NHR$^{17}$)—, —CR$^{17}$=CR$^{18}$—, —C≡C—, —C(O)O—, —C(O)S—, —OC(O)O—, —C(O)NR$^{17}$—, —CR$^{17}$=N—, —CR$^{17}$=NNH—, —NHC(O)O—, —NHC(O)NR$^{17}$—, —CH(OH)CH(CO$_2$R$^{17}$)—, —CH=CR$^{17}$C(O)—, —C≡C—C≡C—, —CH(CHR$^{17}$R$^{18}$)S—,

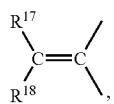

—CH(CH(CH$_3$)$_2$)Si(CH$_3$)$_2$—, —C(O)CH(CO$_2$R$^{17}$)—, and

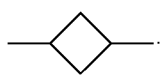

R17 and R18 are independently selected from the group consisting of hydrogen, (1C-4C)alkyl and a group that confers a selected chemical or physical characteristic, or a combination thereof, on the module.

It is an aspect of this invention that, in the above amphiphilic modules, every other synthon is the same; that the first, third, and if present, fifth, seventh, etc., synthons are the same and the second, and if present, the fourth, sixth, eighth, etc., synthons are the same.

It is an aspect of this invention that, in the above amphiphilic modules, all the linkers are the same.

An aspect of this invention is an amphiphilic module comprising 12 synthons.

An aspect of this invention is an amphiphilic module comprising 10 synthons.

An aspect of this invention is an amphiphilic module comprising 8 synthons.

An aspect of this invention is an amphiphilic module comprising 6 synthons.

An aspect of this invention is an amphiphilic module comprising 4 synthons.

An aspect of this invention is an amphiphilic module of claim 1, comprising the formula:

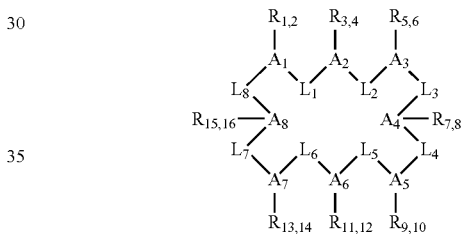

$A_1$-$A_8$ are synthons. $L_1$-$L_8$ are linkers. One or more of $R_1$, $R_3$, $R_5$, $R_7$, $R_9$, $R_{11}$, $R_{13}$ and $R_{15}$ comprises a lipophilic group, which may be same as, or different from, each of the other lipophilic groups. One or more of $R_2$, $R_4$, $R_6$, $R_8$, $R_{10}$, $R_{12}$, $R_{14}$ and $R_{16}$ comprises a hydrophilic group, which may be the same as, or different from, each other hydrophilic group. Each R group that is not a lipophilic or a hydrophilic group is independently either absent or comprises a group that confers a selected chemical or physical characteristic or combination thereof on the module. Each A and each L may also optionally be bonded to one or more additional substituents that confer selected chemical or physical characteristics or combinations thereof on the module.

It is an aspect of this invention that, in the above amphiphilic module, $A_1$, $A_3$, $A_5$ and $A_7$, comprise the same synthon.

It is an aspect of this invention that, in the above amphiphilic module, $A_2$, $A_4$, $A_6$ and $A_8$ comprise the same synthon, which is different from the $A_1$, $A_3$, $A_5$ and $A_7$, synthon.

It is an aspect of this invention that, in the above amphiphilic module all the linkers are the same.

An aspect of this invention is an amphiphilic module, comprising the chemical structure:

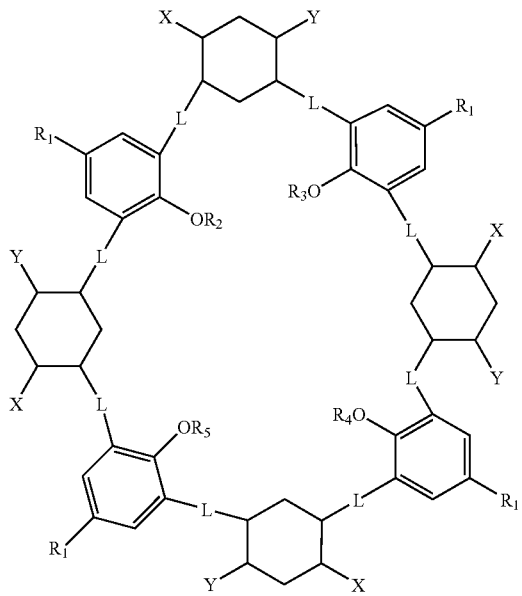

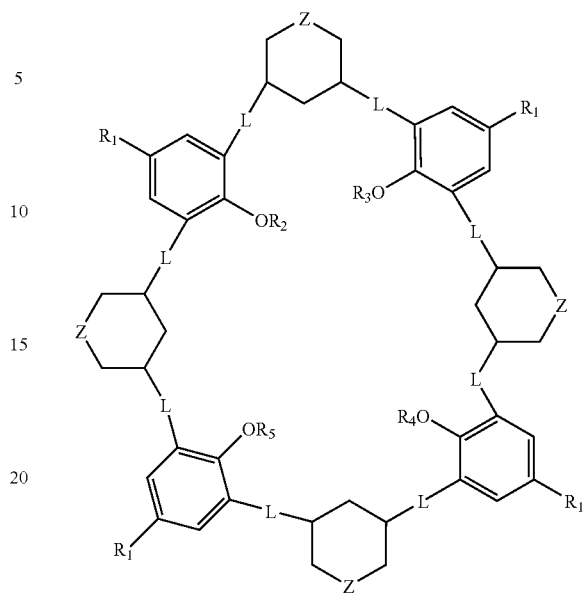

X and Y are independently hydrogen, —OC(O)CH=CH$_2$, —NHC(O)CH=CH$_2$,

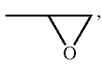

—SH or —NH$_2$. In the alternative, X can be —C(O)OH, —C(O)OCH$_3$, —C(O)Cl or another activated acid and Y is —NH$_2$, —OH or —SH. R1 is selected from the group consisting of —CH$_2$—(10C-18C)alkyl, —CH=CH-(10C-18C)alkyl, —C≡C—(10C-18C)alkyl, —OC(O)-(10C-18C)alkyl, —C(O)O-(10C-18C)alkyl, —NHC(O)-(10C-18C)alkyl, —C(O)NH-(10C-18C)alkyl and —O—(10C-18C)alkyl. One or more of R$_2$, R$_3$, R$_4$ and R$_5$ are independently selected from the group consisting of hydrogen, —C(O)(CH$_2$)$_2$C(O)OCH$_3$, —C(O)CH=CH$_2$,

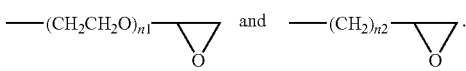

The subscript n1 is 1-50 and n2 is 1-4. At least one of R$_2$, R$_3$, R$_4$ must be other than hydrogen. L is selected from the group consisting of —C(O)O—, —C(O)NH—, CH$_2$NH— and —CH=N—, wherein the oxygen or nitrogen is bonded to either the benzene ring or the cyclohexyl ring.

In an aspect of this invention, the nitrogen or oxygen of the L group is bonded to the cyclohexyl group in the above amphiphilic module.

In another aspect of this invention, the nitrogen or oxygen of the L group alternate around the ring. Thus, if a nitrogen or oxygen of an L group is bonded to the cyclohexyl ring, the nitrogen or oxygen of the next L group going around the ring is bonded to the benzene ring.

An aspect of this invention is an amphiphilic module comprising the chemical structure:

Z is —NZ$_1$- or —CZ$_2$Z$_3$. Z$_1$ is selected from the group consisting of hydrogen, an amino acid residue and C(O)CH=CH$_2$. Z$_2$ is hydrogen and Z$_3$ is selected from the group consisting of hydrogen, —OH, —NH$_2$ and —SH. In the alternative, one of Z$_2$ or Z$_3$ is selected from the group consisting of hydrogen, —OH, —NH$_2$, —SH, —(CH$_2$)z4OH, —(CH$_2$)$_{z4}$NH$_2$ and —(CH$_2$)$_{z4}$SH and the other is selected from the group consisting of —(CH$_2$)$_{z4}$OH, —(CH$_2$)$_{z4}$NH$_2$ and —(CH$_2$)$_{z4}$, SH, wherein Z$_4$ is 1, 2, 3 or 4. R$_1$ is selected from the group consisting of CH$_2$-(10C-18C)alkyl, —CH=CH-(10C-18C)alkyl, —C≡C-(10C-18C)alkyl, —OC(O)-(10C-18C)alkyl, —C(O)O-(10C-18C)alkyl, —NHC(O)-(10C-18C)alkyl, —C(O)NH-(10C-18C)alkyl and —O-(10C-18C)alkyl. One or more of R$_2$, R$_3$, R$_4$, and R$_5$ are independently selected from the group consisting of hydrogen, —C(O)(CH$_2$)$_2$C(O)OCH$_3$, —C(O)CH=CH$_2$,

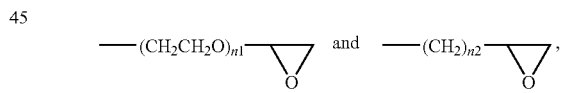

wherein n1 is 1-50 and n2 is 1-4. At least one of R$_2$, R$_3$, R$_4$ must be other than hydrogen. L is selected from the group consisting of —C(O)O—, —C(O)NH—, —CH$_2$NH— and —CH=N—, wherein the oxygen or nitrogen is bonded to either the benzene ring or the cyclohexane ring.

It is an aspect of this invention that, in the above amphiphilic module the nitrogen or oxygen of the L group is bonded to the cyclohexyl ring.

It is likewise an aspect of this invention that, in the above amphiphilic module, the nitrogen or oxygen of the L group alternates around the ring. Thus, if a nitrogen or oxygen of an L group is bonded to the cyclohexyl ring, the nitrogen or oxygen of the next L group going around the ring is bonded to the benzene ring.

An aspect of this invention is an amphiphilic module, comprising the chemical structure:

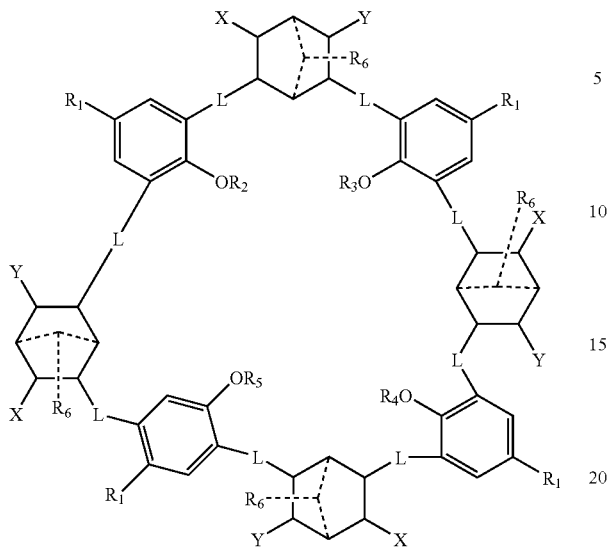

X and Y are independently hydrogen,

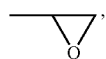

—OC(O)CH=CH$_2$, —NHC(O)CH=CH$_2$, —SH or —NH$_2$. In the alternative, X can be —C(O)OH, —C(O)OCH$_3$, —C(O)Cl or another activated acid and Y is —NH$_2$, —OH or —SH.

When X and Y are both hydrogen or —C(O)OCH$_3$, R$_1$ is selected from the group consisting of —CH=CH$_2$, —OC(O)CH=CH$_2$ and —NHC(O)CH=CH$_2$. When X and Y are both —SH or —NH$_2$ or X is —C(O)OCH$_3$ and Y is —NH$_2$, R$_1$ is hydrogen. R$_6$ is selected from the group consisting of CH$_2$-(10C-18C)alkyl, —CH=CH-(10C-18C)alkyl, —C≡C-(10C-18C)alkyl, —OC(O)-(10C-18C)alkyl, —C(O)O-(10C-18C)alkyl, —NHC(O)-(10C-18C)alkyl, —C(O)NH-(10C-18C)alkyl and —O-(10C-18C)alkyl. One or more of R$_2$, R$_3$, R$_4$, and R$_5$ are independently selected from the group consisting of hydrogen, —C(O)(CH$_2$)$_2$C(O)OCH$_3$, —C(O)CH=CH$_2$,

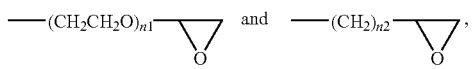

wherein n1 is 1-50 and n2 is 1-4. At least one of R$_2$, R$_3$, R$_4$ must be other than hydrogen. L is selected from the group consisting of —C(O)O—, —C(O)NH—, —CH$_2$NH— and —CH=N—, wherein the oxygen or nitrogen is bonded to either the benzene ring or the bicyclo[2.2.1]heptane ring.

In an aspect of this invention, in the above amphiphilic module, the nitrogen or oxygen of the L group is bonded to the bicyclo[2.2.1]heptane ring.

In an aspect of this invention, in the above amphiphilic module, the nitrogen or oxygen of the L group alternates around the ring. Thus, if a nitrogen or oxygen of an L group is bonded to the bicyclo[2.2.1]heptane ring, the nitrogen or oxygen of the next L group going around the ring is bonded to the benzene ring.

An aspect of this invention is an amphiphilic module comprising the structure:

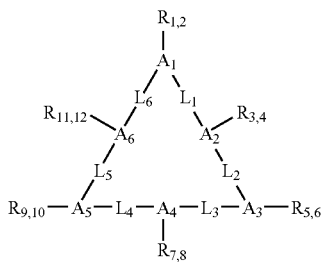

A$_1$-A$_6$ are the synthons. L$_1$-L$_6$ are the linkers. One or more of R$_1$, R$_3$, R$_5$, R$_7$, R$_9$, and R$_{11}$, comprises a lipophilic group, which may be same as, or different from, each other. One more of R$_2$, R$_4$, R$_6$, R$_8$, R$_{10}$ and R$_{12}$ comprises a hydrophilic group, which may be the same as, or different from, each other. Each R group that is not a lipophilic or a hydrophilic group is independently either absent or comprises a group that confer a selected chemical or physical characteristic or combination thereof on the module. Each A and each L may optionally be bonded to one or more additional substituents that confer selected chemical or physical characteristics or combinations thereof on the module.

In an aspect of this invention, in the above amphiphilic module, A$_1$, A$_3$ and A$_5$ comprise the same synthon.

In an aspect of this invention, A$_2$, A$_4$ and A$_6$ in the above amphiphilic module also comprise the same synthon, which is different from the A$_1$, A$_3$ and A$_5$ synthon.

In an aspect of this invention, in the above amphiphilic module, all the linkers are the same.

An aspect of this invention is an amphiphilic module comprising the structure:

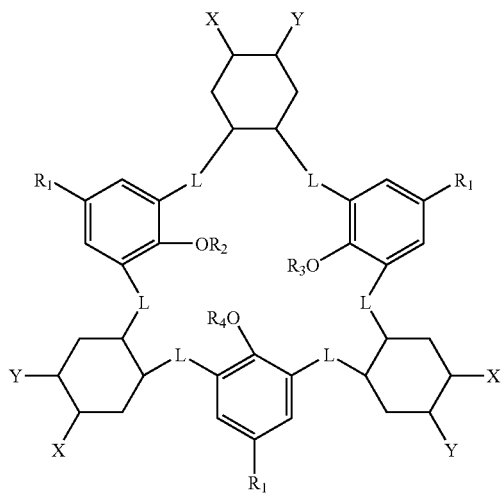

X and Y are both —SH or —NH$_2$. In the alternative, X is —C(O)OH, —C(O)OCH$_3$, —C(O)Cl or another activated acid and Y is —NH$_2$. R$_1$ is selected from the group consisting of —CH$_2$-(10C-18C)alkyl, —CH=CH-(10C-18C)alkyl, —C≡G(10C-18C)alkyl, —OH(O)-(10C-18C)alkyl, —C(O)O-(10C-18C)alkyl, —NHC(O)-(10C-18C)alkyl, —C(O)NH-(10C-18C)alkyl and —O-(10C-18C)alkyl. $R_2$, $R_3$ and $R_4$ are independently selected from the group consisting of hydrogen, —C(O)(CH$_2$)$_2$C(O)OCH$_3$, —C(O)CH=CH$_2$,

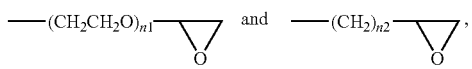

wherein n1 is 1-50 and n2 is 1-4. At least one of $R_2$, $R_3$ or $R_4$ must be other than hydrogen. L is selected from the group consisting of —C(O)O—, —C(O)NH—, CH$_2$NH— and —CH=N— wherein the oxygen or nitrogen is bonded to either the benzene ring or the cyclohexyl ring.

In an aspect of this invention, in the above amphiphilic module, the nitrogen or oxygen of the L group is bonded to the cyclohexyl ring.

In a further aspect of this invention, in the above amphiphilic module the nitrogen or oxygen of the L group alternates around the ring. Thus, if a nitrogen or oxygen of an L group is bonded to the cyclohexyl ring, the nitrogen or oxygen of the next L group going around the ring is bonded to the benzene ring.

An aspect of this invention is an amphiphilic module, comprising the chemical structure:

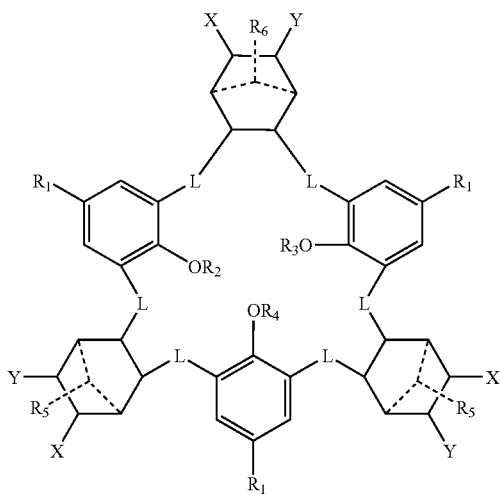

X and Y are independently hydrogen,

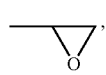

—OC(O)CH=CH$_2$, —NHC(O)CH=CH$_2$, —SH or —NH$_2$. In the alternative, X is —C(O)OH, —C(O)OCH$_3$, —C(O)Cl or another activated acid and Y is —NH$_2$, —OH or —SH. When X and Y are both hydrogen or —C(O)OCH$_3$, $R_1$ is selected from the group consisting of —CH=CH$_2$, —OC(O)CH=CH$_2$ and —NHC(O)CH=CH$_2$. When X and Y are both —SH or —NH$_2$ or X is —C(O)OCH$_3$ and Y is —NH$_2$, $R_1$ is hydrogen. $R_5$ is selected from the group consisting of CH$_2$-(1OC-18C)alkyl, —CH=CH-(10C-18C)alkyl, —C≡C-

(10C-18C)alkyl, —OC(O)-(10C-18C)alkyl, —C(O)O(1OC-18C)alkyl, —NHC(O)-(10C-18C)alkyl, —C(O)NH-(10C-18C)alkyl and —O-(10C-18C)alkyl. $R_2$, $R_3$ and $R_4$ are independently selected from the group consisting of hydrogen, —C(O)(CH$_2$)$_2$C(O)OCH$_3$, —C H$_2$C(O)CH=CH$_2$,

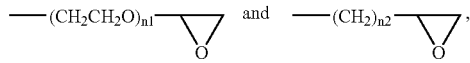

wherein n1 is 1-50 and n2 is 1-4. At least one of $R_2$, $R_3$ or $R_4$, must be other than hydrogen. L is selected from the group consisting of —C(O)O—, —C(O)NH—, —CH$_2$NH— and —CH=N —, wherein the oxygen or nitrogen is bonded to either the benzene ring or the bicyclo[2.2.1]heptane ring.

In an aspect of this invention, in the above amphiphilic module, the nitrogen or oxygen of the L group is bonded to the bicyclo[2.2.1]heptane ring.

In another aspect of this invention, in the above amphiphilic module, the nitrogen or oxygen of the L group alternates around the ring. Thus, if a nitrogen or oxygen of an L group is bonded to the bicyclo[2.2.1]heptane ring, the nitrogen or oxygen of the next L group going around the ring is bonded to the benzene ring.

An aspect of this invention is an amphiphilic module, comprising the chemical structure:

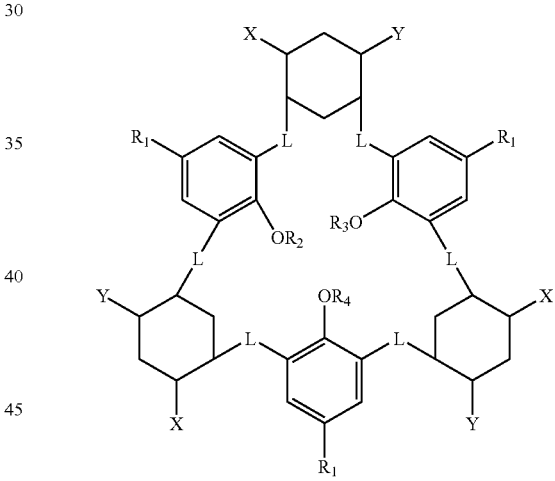

X and Y are independently hydrogen,

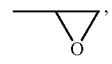

—OC(O)CH=CH$_2$, —NHC(O)CH=CH$_2$, —SH or —NH$_2$. In the alternative, X is —C(O)OH, —C(O)OCH$_3$, —C(O)Cl or another activated acid and Y is —NH$_2$, —OH or —SH. $R_1$ is selected from the group consisting of —CH$_2$-(10C-18C)alkyl, —CH=CH-(10C-18C)alkyl, —C≡C—(10C-18C)alkyl, —OC(O)-(10C-18C)alkyl, —C(O)O-(10C-18C)alkyl, —NHC(O)-(10C-18C)alkyl, —C(O)NH-(10C-18C)alkyl and —O-(10C-18C)alkyl. $R_2$, $R_3$ and $R_4$ are independently selected from the group consisting of hydrogen, —C(O)(CH$_2$)$_2$C(O)OCH$_3$, —C(O)CH=CH$_2$,

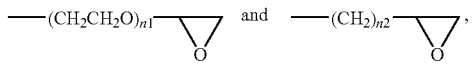 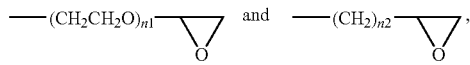

wherein n1 is 1-50 and n2 is 1-4. At least one of $R_2$, $R_3$ or $R_4$ must be other than hydrogen. L is selected from the group consisting of —C(O)O—, —C(O)NH—, —CH$_2$NH— and —CH=N—, wherein the nitrogen or oxygen is bonded to either the benzene ring or the cyclohexyl ring.

In an aspect of this invention, in the above amphiphilic module, the nitrogen or oxygen of the L group is bonded to the cyclohexyl ring.

In another aspect of this invention, in the above amphiphilic module, the nitrogen or oxygen of the L group alternates around the ring. Thus, if a nitrogen or oxygen of an L group is bonded to the cyclohexyl ring, the nitrogen or oxygen of the next L group going around the ring is bonded to the benzene ring.

An aspect of this invention is an amphiphilic module, comprising the chemical structure:

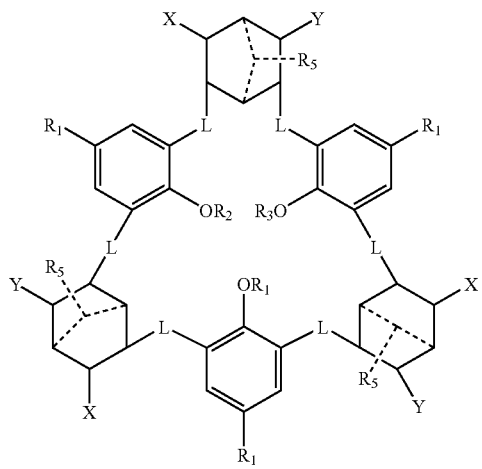

X and Y are independently hydrogen,

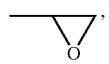

—OC(O)CH=CH$_2$, —NHC(O)CH=CH$_2$, —SH or —NH$_2$. In the alternative, X is —C(O)OH, —C(O)OCH$_3$, —C(O)Cl or another activated acid and Y is —NH$_2$, —OH or H. When X and Y are both hydrogen or —C(O)OCH$_3$, $R_1$ is selected from the group consisting of —CH=CH$_2$, —OC(O)CH=CH$_2$ and —NHC(O)CH=CH$_2$. When X and Y are both —SH or —NH$_2$ or X is —C(O)OCH$_3$ and Y is —NH$_2$, $R_1$ is hydrogen. $R_5$, is selected from the group consisting of CH$_2$-(10C-18C)alkyl, —CH=CH-(10C-18C)alkyl, —C≡C-(10C-18C)alkyl, —OC(O)-(10C-18C)alkyl, —C(O)O-(10C-18C)alkyl, —NHC(O)-(10C-18C)alkyl, —C(O)NH-(10C-18C)alkyl and —O-(10C-18C)alkyl. $R_2$, $R_3$ and $R_4$, are independently selected from the group consisting of hydrogen, —C(O)(CH$_2$)$_2$C(O)OCH$_3$, —C(O)CH=CH$_2$, wherein n1 is 1-50 and n2 is 1-4. At least one of $R_2$, $R_3$ or $R_4$ must be other than hydrogen. L is selected from the group consisting of —C(O)O—, —C(O)NH—, —CH$_2$NH— and —CH=N—, wherein the oxygen or nitrogen is bonded to either the benzene ring or the bicyclo[2.2.1]heptane ring.

In an aspect of this invention, in the above amphiphilic module, the nitrogen or oxygen of the L group is bonded to the bicyclo[2.2.1]heptane ring.

In a further aspect of this invention, in the above amphiphilic module, the nitrogen or oxygen of the L group alternates around the ring. Thus, if a nitrogen or oxygen of an L group is bonded to the cyclohexyl ring, the nitrogen or oxygen of the next L group going around the ring is bonded to the benzene ring.

Another aspect of this invention relates to a method of synthesizing an amphiphilic module. A plurality of a first synthon comprising two functional groups that may be the same or different is provided. A plurality of a second synthon, which is different than the first synthon, but also comprising two functional groups that may be the same or different, is also provided. The functional groups of the first synthons are selected such that they can only react with the functional groups of the second synthons. The first and second synthons are then put together in a solvent under conditions that cause the functional groups to react to form an amphiphilic module. The amphiphilic module is then isolated.

In the above method, a reagent or reagents that catalyzes the reaction of the functional groups of the first synthon with the functional groups of the second synthon may be used.

A further aspect of this invention relates to an alternative method for preparing an Amphiphilic module. This method comprises placing a first synthon comprising a functional group in a solvent and then adding a second synthon comprising a functional group that reacts with the functional group of the first synthon to form a dimer. Then a third synthon is added. The third synthon may be the same as, or different from, the first synthon and comprises a functional group that reacts with a second functional group of the second synthon to form a trimer. The preceding step is repeated until an $n^{th}$ (n is 1-24) synthon is added. The $n^{th}$ synthon comprises a functional group that reacts with a second functional group of the first synthon to form a ring.

In an aspect of this invention, a reagent or reagents may be added to catalyze the reaction of a functional group of a synthon with a functional group of the next synthon being added. In the alternative a reagent may be added that reacts with a functional group of a synthon to form an intermediate, which then reacts with a functional group of the next synthon that is added.

An aspect of this invention is a two-dimensional array comprising a plurality of amphiphilic modules wherein each module is bonded to one or more adjacent modules by one or more connectors between each pair of adjacent modules.

In an aspect of this invention, in the above array, each connector is independently selected from the group consisting of —O—, —S—, —NR19-, —SS—, —CR$^{19}$R$^{20}$—, —CH(OH)—, —C(OH)R$^{19}$—CH$_2$NR$^{20}$—, —CH(OH)CH(NHR$^{19}$)—, —CR$^{19}$=CR$^{20}$—, —C≡C—, —C(O)O—, —C(O)S—, —OC(O)O—, —C(O)NR$^{19}$—, —CR$^{19}$=N—, —CR$^{19}$=NNH—, —NHC(O)O—, —NHC(O)NR$^{19}$—, —NHCH$_2$NH—, —NHC(NH)CH$_2$C(NH)NH—, —CH(OH)CH(CO$_2$R$^{19}$)—, —CH═CR$^{19}$C(O)—, —C≡C—C≡C—, —CH(CHR$^{19}$R$^{20}$)S—,

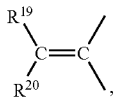

—CH(CH(CH$_3$)$_2$)Si(CH$_3$)$_2$—, —C(O)CH(CO$_2$R$_{19}$)—,

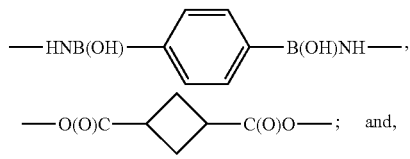

and, an acrylate copolymer formed by reaction of a —OC(O)CH═CH$_2$ group on each module and ethyl acrylate. R19 and R20 are independently selected from the group consisting of hydrogen, (1C-4C)alkyl and a group that confers a selected chemical or physical characteristic, or a combination thereof.

In an aspect of this invention, in the above array, the connector is separated from one or both of the modules by a spacer.

The spacer comprises a —(CH$_2$) n-group, wherein n is 1-28, in another aspect of this invention.

DETAILED DESCRIPTION OF THE INVENTION

Brief Description of the Tables

Table 1 is a list of functional groups that can react to form the presently preferred linkers. The linkers formed are also shown.

Table 2 shows the results of quantum mechanical and molecular mechanical computations of the size of the pores formed from selected sets of synthons and linkers.

Table 3 shows the results of quantum mechanical and molecular mechanical computations of the size of the pores formed by additional sets of synthons and linkers.

Table 4 shows the results of experiments carried to determine what size ion can pass through a selected module of this invention.

BRIEF DESCRIPTION OF THE FIGURES

The figures are provided solely as visual aids in understanding the present invention. They are not intended, nor should they be construed, to limit the scope of this invention in any manner whatsoever. For example, hexameric modules are used to exemplify close-packed arrays (FIG. 2A). Certain synthons are shown with functional groups that form connectors (FIGS. 2B and 2C). Certain functional groups, e.g., amino (—NH$_2$) groups are shown forming connectors (FIG. 5). It is understood that other size modules, other synthons and other functional groups could just as easily have been used in the figures.

FIG. 1A shows the structure of a tetramer module, essentially a parallelogram.

FIG. 1B shows the structure of a hexamer module, essentially an equilateral triangle.

FIG. 1C show the structure of an octamer module, essentially a rhombus.

FIG. 2A shows the array without any connectors between modules.

FIG. 4A shows an imidate connector.

FIG. 4B shows an urea connector.

FIG. 5A shows connectors formed when two functional functional groups are bonded to the same synthon in each module. In 5A, the connector is an aminal.

FIG. 6A shows amphiphilic modules in chloroform which is floating on a layer of water.

FIG. 6B shows the amphiphilic modules on the surface of the water after the chloroform has been evaporated.

DISCUSSION

Figure 1A:
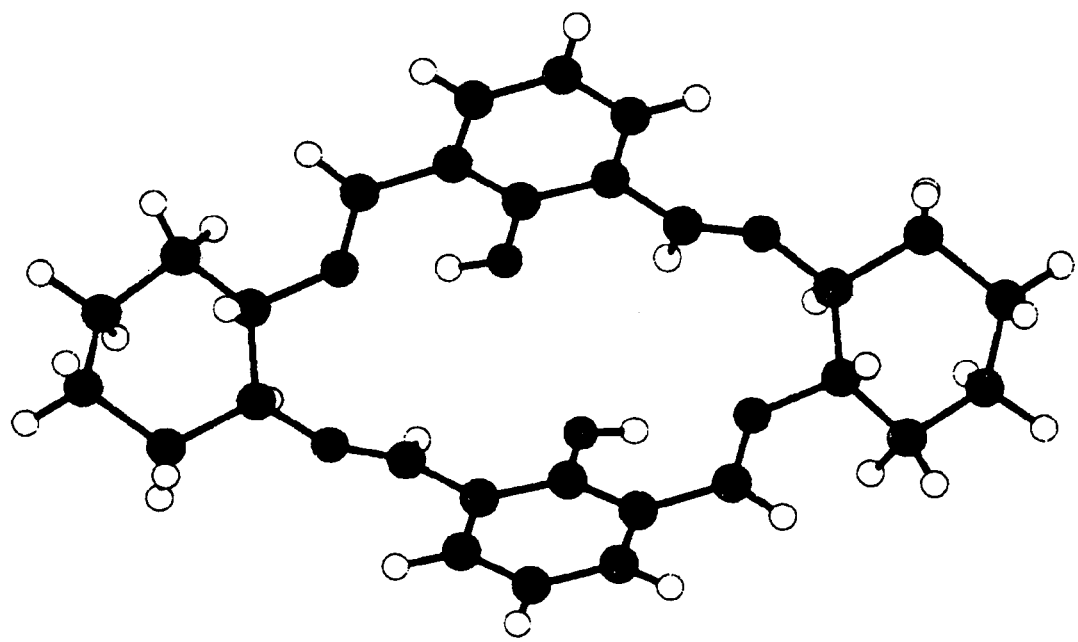
FIGS. 1A-1C show the structure of modules of this invention as determined by energy minimization computation.

As used herein, an "(nC-mC)alkyl, wherein n is 1 to 8 and m is 8 to 28, refers to all alkyl groups comprising n to m carbon atoms. For example, a (1 C-4C)alkyl refers to a methyl (1 carbon atom), ethyl (2 carbon atoms), propyl (3 carbon atoms) or butyl (4 carbon atoms) group. All possible isomers of the indicated alkyl are also included. Thus "propyl" includes isopropy, "butyl" includes n-butyl, isobutyl and t-butyl, etc.

As used herein, "amphiphilic" refers to a molecule that contains both hydrophilic and lipophilic (or, synonymously, hydrophobic) moieties.

Hydrophilic means "water-loving." The hydrophilic moiety of an amphiphilic molecule has an affinity for and is generally miscible with water. If placed at a water/water-immiscible liquid (or a water/air) interface, the hydrophilic moiety will partition into the water layer. Examples of hydrophilic moieties include, without limitation, hydroxyl, methoxy, phenol, carboxylic acids and salts thereof, methyl and ethyl esters of carboxylic acids, amides, amino, cyano, ammonium salts, sulfonium salts, phosphonium salts, polyethyleneglycols, epoxy groups, acrylates, sulfonamides, nitro, —OP(O)(OCH$_2$CH$_2$N$^+$RR'R")O$^-$, guanidinium, aminate, acrylamide and pyridinium.

Lipophilic means "lipid-loving," which, because lipids are oily, water insoluble compounds, is understood to mean generally "oil-loving." The lipophilic moiety of an amphiphilic molecule avoids water and has an affinity for and is generally miscible with water-immiscible liquids. Thus, if placed at a water/water immiscible liquid (or a water/air) interface, a lipophilic moiety will partition into the water-immisible liquid layer (or into the air). The most common example of a lipophilic moiety is a long, straight or branched chain hydrocarbon. Presently preferred lipophilic groups consist of at least eight (8) carbon atoms in a branched or straight chain. More preferably, the total number of carbon atoms in the chain will be 10 or more, still more preferably 12 or more. A straight chain or each branch of a branched chain may comprise any number of carbon atoms over the indicated minimum. However, the straight chain or each branch of a branched chain will comprise a maximum of 28 carbon atoms in a presently preferred embodiment of this invention. Each chain may independently comprise, without limitation, alkenyl, alkynyl, alicyclic or aromatic groups. Each chain may also contain, interspersed among the carbons of the chain, one or more silicon atoms substituted with alkyl, alkenyl, alkynyl, alicyclic or aryl groups. Likewise the carbon atoms of each chain may independently be substituted with one or more fluorine atoms.

Other lipophilic and hydrophilic moieties useful in the present invention will become apparent to those skilled in the art based on the disclosure herein. All such moieties are within the scope of this invention.

Based on the above, it should be clear that an amphiphilic molecule, placed at a water/water-immiscible liquid (or water/air) interface will orient itself such that its hydrophilic moiety is in the water layer and its lipophilic moiety is in the water-immiscible layer (or in the air).

In general, a "synthon" refers to a molecule that can be connected with other molecules, which may be the same as, or different than, the initial molecule and each other, to create a larger molecule. As used herein, a "synthon" refers to a multifunctional organic molecule of predominantly one stereochemical configuration. It may also refer to a molecule that is predominantly a single enantiomer. By "multifunctional" is meant that the molecule is substituted with at least two functional groups, which may be the same as, or different than, each other. Connection of synthons of this invention to create larger molecular entities occurs through covalent bonds resulting from reaction of a functional group on one synthon with a functional group on another synthon. A synthon may also be substituted with additional functional groups that do not participate in synthon interconnections but rather impart selected physical or chemical characteristics to the synthon. Presently preferred synthons of this invention are cyclic.

By a "cyclic" synthon is meant a monocyclic or multicyclic ring system. The monocyclic ring or each ring of a multicyclic system may independently be aryl, heteroaryl, alicyclic or heteroalicyclic. "Aryl" refers to an all-carbon ring that contains a π-electron system that is delocalized throughout the ring, that is, the ring is "aromatic." "Heteroaryl" refers to an aromatic ring that contains nitrogen, oxygen or sulfur in addition to carbon. "Alicyclic" refers to an all-carbon ring that, while it may contain one or more double bonds, does not have a fully delocalized π-electron system. "Heteroalicyclic" refers to a ring that contains atoms other than carbon and that, likewise, does not have a fully delocalized π-electron system. Multicyclic ring systems may consist of fused rings, i.e., each ring shares at least one ring atom with another ring or they may simply be connected to one another through one or more covalent bonds. Examples of cyclic synthons of this invention include, without limitation, benzene, naphthalene, anthracene, phenylene, phenathracene, pyrene, triphenylene, phenanthrene, pyridine, pyrimidine, pyridazine, biphenyl, bipyridyl, cyclohexane, cyclohexene, decalin, piperidine, pyrrolidine, tetrahydropyran, tetranhydrothiane, 1,3-dioxane, 1,3-dithiane, 1,3-diazane, tetrahydrothiophene, tetrahydrofuran, pyrrole, cyclopentane, triptycene, adamantane, bicyclo[2.2.1]heptane, bicyclo[2.2.1]heptene, bicyclo[2.2.2]octane, bicyclo[2.2.2]octene, bicyclo[3.3.0]octane, bicyclo[3.3.0]octene, bicyclo[3.3.1]nonane, bicyclo[3.3.1]nonene, bicyclo[3.2.2]nonane, bicyclo[3.2.2]nonene, bicyclo[4.2.2]decane, 7-azabicyclo[2.2.1]heptane, 1,3-diazabicyclo[2.2.1]heptane, spiro[4.4]nonane and the like.

As used herein, a "linker" refers to the reaction product of a functional group on one synthon with a functional group on another synthon resulting in a bridge of covalently bonded atoms between synthons. The reaction may involve the direct chemical interaction of a functional group on one synthon with a functional group on another synthon to form the linker. For example, a linker might comprise an ester, which is the reaction product of a hydroxyl group on one synthon with an acid or acid halide on another synthon. Another example is an amide, which would result from the reaction of an amine on one synthon with an acid or acid halide on another synthon. A further example would be the reaction of an aldehyde or ketone on one synthon with an amine on another synthon to form an imine. A linker might comprise the reaction product of a 2+2 cycloaddition of two alkenes, one on each synthon. A linker could also contain one or more atoms provided by a moiety other than the two functional groups. This external moiety is selected so as to react with the functional group on one synthon to form an intermediate that then reacts with a functional group on another synthon to form the covalent bridge of atoms between the synthons. An example, without limitation, of such a linker is the reaction product of an amino group on one synthon, a methyl ketone on another synthon and formaldehyde as the external molecule. Under either acidic or basic conditions, this combination of moieties will enter into the Mannich reaction. In presently preferred embodiments of this invention, the linker is the reaction product of a functional group directly bonded to one synthon with a functional group directly bonded to another synthon. Thus, a presently preferred linker is the imine, —CH=N—, resulting from the reaction of an aldehyde, —CH=O, on one synthon with an amine, —NH$_2$, on another synthon. Other presently preferred linkers are esters and amides, which are discussed above. It is also possible, and is within the scope of this invention, that the linker may be separated from one or both synthons by a spacer. The spacer can be any chemical entity that forms a bridge of covalently bonded atoms between the synthon and a functional group and that does not interfere with the linker-forming reaction. The simplest example of a spacer is methylene, —CH$_2$—; for example, if a methylene spacer were inserted between an aldehyde group and its synthon in the above imine linker-forming reaction, the linker would be —CH$_2$CH=N—. A list of presently preferred linker-forming functional groups and the linkers that they form are shown in Table 1.

TABLE 1

| | Functional Group A | Functional Group B | Linker Formed |
|---|---|---|---|
| 1 | R—NH$_2$ | R'—C(O)H | R—N=CH—R' |
| 2 | R—NH$_2$ | R'—CO$_2$R" | R—NHC(O)—R' |
| 3 | R—OH | R'—CO$_2$R" | R—OC(O)—R' |
| 4 | R—X | R'-Ona | R'—O—R |
| 5 | R—SH | R'—SH | R—S—S—R' |
| 6 | R—X | R'Sna | R—S—R' |
| 7 | R—X | (R')$_2$NH | R—N—(R')$_2$ |
| 8 | R—X | (R'CH$_2$)CuLi | R—CH$_2$—R' |
| 9 | R—X | R'—X | R—R' |
| 10 | R-Sna | R'C(O)OR" | R'C(O)SR |
| 11 | R—X | R'—≡—H | R'—≡—R |
| 12 | R—≡—H | R'—≡—H | R—≡—≡—R |
| 13 | R—MgX | R'C(O)H | RCH(OH)R' |
| 14 | R—NH$_2$ | epoxide R' | R'—CH(OH)—CH$_2$—NHR |
| 15 | R—MgX | epoxide R' | R'—CH(OH)—CH$_2$—R |
| 16 | CH$_2$=CHR | R'—X | R'—C(CH$_3$)=CHR |
| 17 | RC(O)H | R'C(O)H | RHC=CHR' |
| 18 | CH$_2$=CHR | R'C(O)Cl | enone with R', R |
| 19 | RN=C=O | R'NH$_2$ | urea R-NH-C(O)-NH-R' |
| 20 | RN=C=O | HOR' | carbamate R-NH-C(O)-O-R' |
| 21 | RC(O)H | R'NH—NH$_2$ | RCH=NNHR' |
| 22 | R—OH | R'OC(O)X | ROC(O)OR' |
| 23 | CH$_2$=CHR | R'—SH | R'S—CH$_2$—CHR |
| 24 | isobutyryl ester | R'C(O)R" | β-hydroxy ester |
| 25 | RCH$_2$C(O)OR' | R"C(O)OR''' | β-ketoester RC(R)(C(O)OR')C(O)R" |
| 26 | CH$_2$=CHR | (CH$_3$)$_2$(R')—SiH | silyl adduct |
| 27 | CH$_2$=CHR | CH$_2$=CHR' | cyclobutane with R, R' |
| 28 | RP(O)(OH)$_3$ | R'OH | RP(O)(OH)$_2$OR' |

Other linkers and spacers will become apparent to those skilled in the art based on the disclosure herein; all such linkers and spacers are within the scope of this invention.

In general, a "module" refers to two or more synthons bonded to one another by linkers. In particular, an "amphiphilic module" refers to a module in which one or more of the synthons is substituted with one or more lipophilic moieties and one or more of the synthons is substituted with one or more hydrophilic moieties. The same synthon may, if desired, be substituted with both a lipophilic and a hydrophilic moiety. A presently preferred module comprises a two-dimensional array of three (3) or more synthons in which each synthon is covalently bonded to two other synthons to form a ring of synthons. It is also a presently preferred embodiment of this invention that the ring of synthons, i.e., the amphiphilic module, defines a pore.

As used herein, a "pore" refers to the hole created by the ring of synthons that form a module.

As used herein, a "nanopore" refers to a pore, which is from 0.5 nanometer (nm) to approximately 100 nm in diameter.

As used herein, an "activated acid" refers to a —C(O)R moiety in which the R is readily displaced by a nucleophile to form a covalent bond between the —C(O)— and the nucleophile. Examples, without limitation, of activated acids include acid chlorides, acid fluorides, p-nitrophenyl esters, pentafluorophenyl esters and N-hydroxysuccinimide esters.

As used herein, a "reagent" refers to a chemical entity or a physical agent that interacts with functional groups to cause or facilitate the reaction of the functional groups to form a covalent bond or chain of covalent bonds between the moieties to which the functional groups are bonded. Examples of chemical reagents are, without limitation, acids and bases. Examples of physical agents are, without limitation, ultraviolet light, ion plasma and temperature changes. In addition to causing or facilitating the reaction of functional groups, the reagent might also itself react with one of the functional groups to form an intermediate chemical entity. The intermediate then reacts with another functional group to create a chain of covalently bonded atoms between the moieties to which the functional groups are attached. An "intermediate" refers to a chemical entity that forms during a reaction but which is not itself isolated, in fact is often not isolable, but which reacts further with other entities in the reaction mixture to give a final product.

As used herein, an "amino acid residue" refers to the chemical entity formed when a compound comprising at least one amino (—NH$_2$) and at least one carboxyl (—C(O)O) group reacts, through the amino or carboxyl group, with an atom or functional group of a synthon. Whichever of the two groups, is not participating in the linker or connector forming reaction may be blocked with a removable protective group.

As used herein, "bond," "bonding" or "bonded" refers, unless otherwise expressly stated, to covalent bonds between the entities which are the subject of the bonding.

As used herein, the phrase "confer selected chemical or physical characteristics or combinations thereof on the module" refers to functional groups that are present on the modules for purposes other than forming linkers, forming connectors, or conferring amphiphilicity on the module. For example, without limitation, a functional group might be bonded to the module in such a manner that it extends into the pore of the module and is capable of chelating a particular atom or molecule should that atom or molecule attempt to traverse the pore. The functional group might be a charged species, e.g., a carboxylate anion or ammonium group, which could be positioned in or near a pore to trap oppositely-charged species. A functional group that alters electrical conductivity in the region of a pore might be incorporated into a module. The functional group might also be one that varies the hydrophilicity or lipophilicity in the vicinity of a pore. Of course, a functional group might also be bonded to the module at locations other than the pore and might be used to modify other chemical or physical characteristics of the module. A functional group might also serve more than one purpose. For example, without limitation, a functional group might initially be part of a moiety that confers hydrophilicity on a module. Once the module has formed a Langmuir film, the functional group might be used to form a connector.

As used herein, a "functional group" or "chemical moiety" refers broadly to any group that is covalently bonded, directly or indirectly, to any of the synthons that comprise the module. By "indirectly" is meant that the functional group can be separated form the synthon's ring structure by one or more spacers. The terms include, but are not limited to, the traditional groups considered "functional" by those skilled in the art, e.g., amino (—$NH_2$), hydroxyl (—OH), cyano (—C≡N), nitro ($NO_2$), carboxyl (—COOH), formyl (—CHO), keto (—$CH_2$C(O)$CH_2$—), alkenyl (—C=C—), alkynyl (—C≡C—), halo (F, Cl, Br and I) groups and the like. The term also refers to groups such as aryl, heteroaryl, alicyclic and heteroalicyclic, which may themselves be further substituted with one or more of the preceding groups.

An amphiphilic module of the present invention is comprised of three or more synthons covalently bonded to one another to form a ring. In a presently preferred embodiment, the ring of synthons circumscribes an open region or pore. In a further presently preferred embodiment of this invention the pore is a nanopore. Thus, a first synthon is covalently bonded to a second synthon through a linker, the second synthon is bonded to a third synthon through another linker, the third to a fourth through yet another linker and so on until the desired number of synthons have been linked. The last synthon in the chain is then covalently bonded to the first synthon through a linker to form a ring of synthons that encloses an open region, which comprises the nanopore. In a presently preferred embodiment of this invention, the synthons are prepared or isolated as essentially single configurational isomers or as essentially pure enantiomers. By "essentially" is meant as near to configurational or enantiomeric purity as is practically achievable. In general, this means at least 80%, preferably 90% and most preferably 98+% pure.

Synthons

To avoid the need to separate single configurational or enantiomeric isomers from complex mixtures resulting from non-specific reactions, it is preferred to employ stereospecific, or at least stereoselective, reactions in the preparation of the synthons of this invention. The following are examples of synthetic schemes that employ such reactions to give several classes of synthons useful in the preparation of amphiphilic modules of this invention. The examples are not intended to be, and are not to be construed as, limiting on the scope of this invention in any manner whatsoever, it being understood that countless synthons and schemes for their preparation will become apparent to those skilled in the art based on the disclosures herein. All such synthons and schemes are with the scope of this invention. For clarity, no lipophilic moieties are shown on the structures in the following examples. However, it is understood that any of the following synthetic schemes could readily be modified to include a step for the inclusion of a lipophilic moiety if in fact it were desired to have such on the particular synthon.

1,3-Diaminocyclohex-5-ene Synthons

An approach to this class synthons is outlined in Scheme 1. The key reaction in this process is the enzymatically assisted partial hydrolysis of the

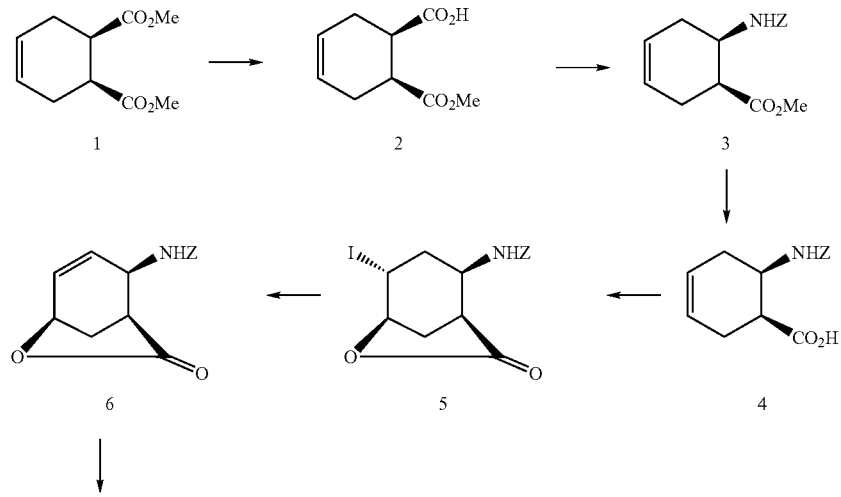

SCHEME 1

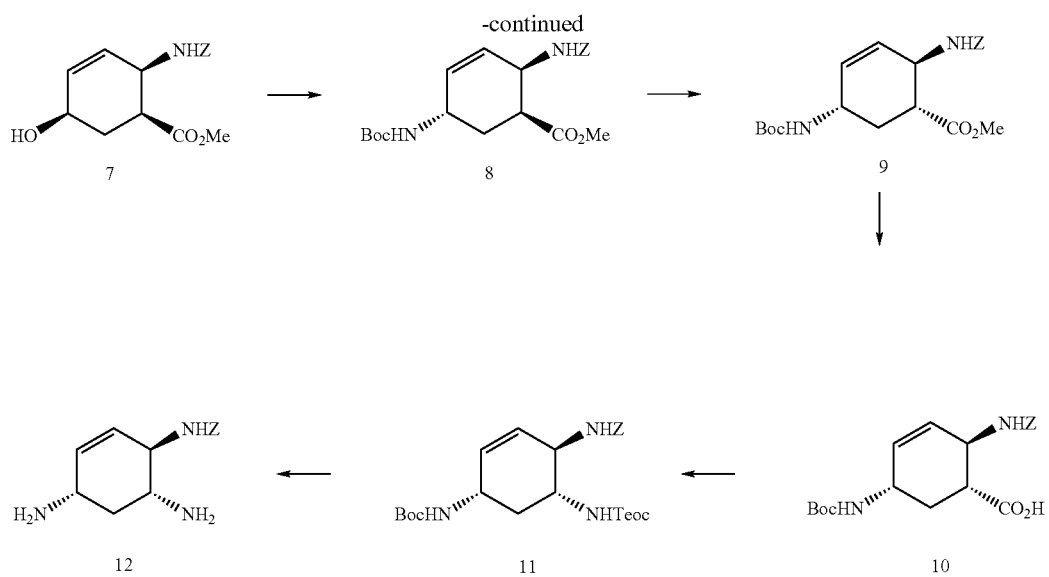

-continued symmetrical diester S1-1 (for the sake of clarity, compounds will be numbered in relation to the scheme in which they appear; thus "S1-1" refers to the structure 1 in Scheme 1, etc.) to give enantiomerically pure S1-2. S1-2 was subjected to the Curtius reaction and then quenched with benzyl alcohol to give protected amino acid S1-3. Iodolactonization of carboxylic acid S1-4 followed by dehydrohalogenation gives unsaturated lactone S1-6. Opening of the lactone ring with sodium methoxide gives alcohol S1-7, which is converted with inversion of configuration to S1-8 in a one-pot reaction involving mesylation, $SN_2$ displacement with azide, reduction and protection of the resulting amine with di-tert-butyl dicarbonate. Epimerization of S1-8 to the more stable diequatorial configuration followed by saponification gives carboxylic acid S1-10. S1-10 is subjected to the Curtius reaction. A mixed anhydride is prepared using ethyl chloroformate followed by reaction with aqueous $NaN_3$ to give the acyl azide, which is thermally rear-ranged to the isocyanate in refluxing benzene. The isocyanate is quenched with 2-trimethylsilylethanol to give differentially protected tricarbamate S1-11. Reaction with trifluoroacetic acid (TFA) selectively deprotects the 1,3-diamino groups to provide the desired synthon S1-12.

Norbornane Diamine Synthons

Norbornanes (bicycloheptanes) are presently preferred synthons of this invention due, in part, to the relative ease with which stereochemically controlled multifunctionalization can be achieved. For example, Diels-Alder cycloaddition can be used to form norbornanes incorporating various functional groups having specific, predictable stereochemistry. Enantiomerically enhanced products may also be obtained through the use of appropriate reagents, thus limiting the need for chiral separations.

1,2-Diaminonorbornane Synthons

An approach to a this class synthon is outlined in Scheme 2. 5-(Benzyloxy-methyl)-1,3-cyclopentadiene (S2-13) was reacted with

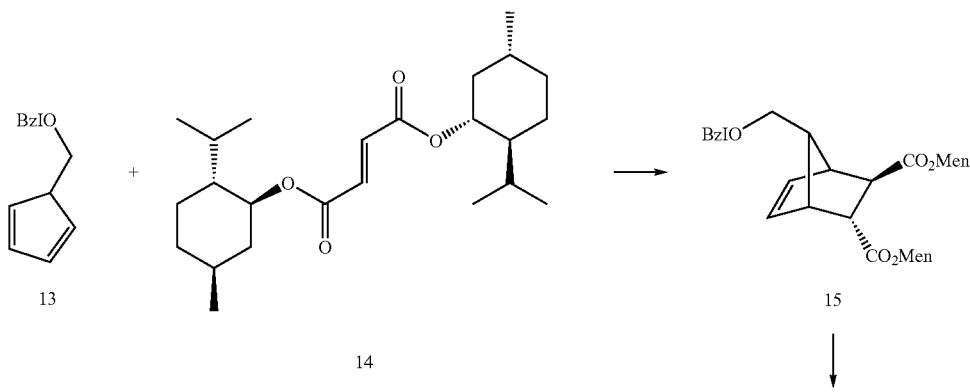

SCHEME 2

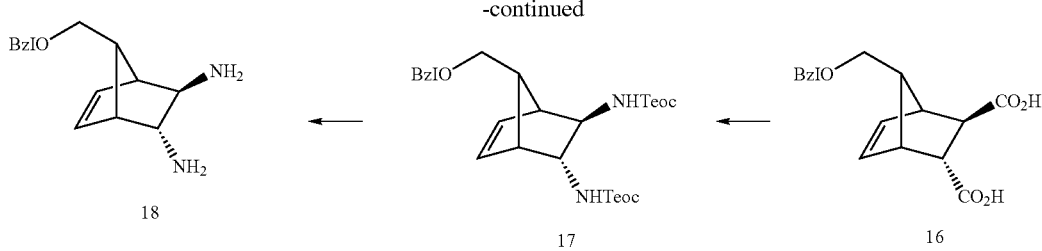

diethylaluminum chloride Lewis acid complex of di-(l)-menthyl fumarate (S2-14) at low temperature to give the diastereomerically pure norbornene S2-15. Saponification with potassium hydroxide in aqueous ethanol gives the diacid S2-16, which is subjected to a tandem Curtius reaction with diphenylphosphoryl azide (DPPA), the reaction product being quenched with 2-trimethylsilylethanol to give the biscarbamate S2-17. Deprotection with TFA gives diamine S2-18.

Another approach to this synthon class is outlined in Scheme 3. Opening of anhydride S3-19 with methanol in the presence of quinidine gives the enantiomerically pure ester acid S3-20. Epimerization of the ester group with sodium methoxide (NaOMe) gives S3-21. A Curtius reaction with DPPA followed by quenching with trimethylsilylethanol give carbamate S3-22. Saponification with NaOH gives the acid S3-23, which then undergoes a Curtius reaction endo,endo-1,3-Diaminonorbornane Synthons An approach to this class synthons is outlined in Scheme 4. 5-Trimethylsilyl-1,3-cyclopentadiene (S4-25) is reacted with the diethylaluminum chloride Lewis acid complex of di-(l)-menthyl fumarate at low temperature to give nearly diastereomerically pure norbornene S4-26. Crystallization of S4-26 from alcohol results in recovery of greater than 99% of the single diastereomer. Bromolactonization followed by silver mediated rearrangement gives mixed diester S4-28 with an alcohol moiety at the 7-position. Protection of the alcohol with benzyl bromide and selective deprotection of the methyl ester gives the free carboxylic acid S4-30. A Curtius reaction results in trimethylsilylethyl carbamate norbornene S4-31. Biscarbonylation of the olefin in methanol, followed by a single-step deprotection and dehydration gives the monoanhydride S4-33. Quinidine mediated opening of the anhydride

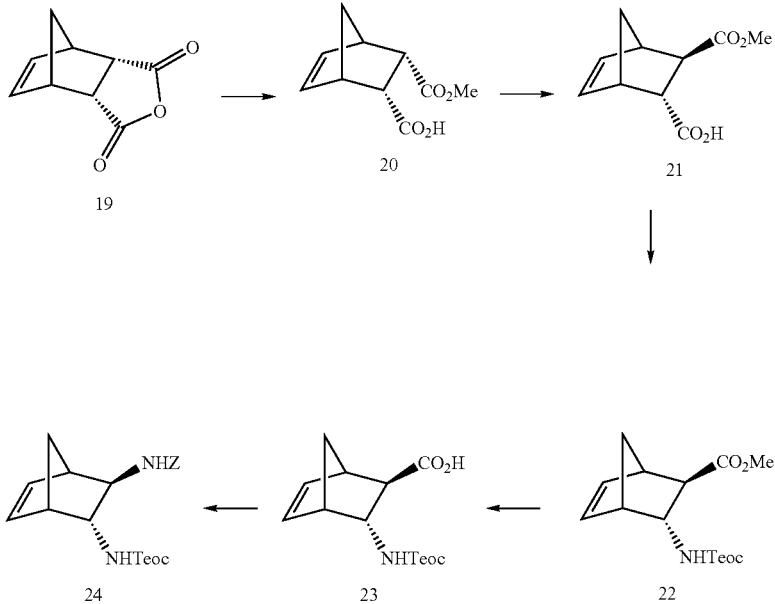

SCHEME 3 which is quenched with benzyl alcohol to give differentially protected biscarbamate S3-24. Compound S3-24 can be fully deprotected to provide the diamine or either of the carbamates can be selectively deprotected.

with methanol S4-34. Curtius transformation of S4-34 gives the biscarbamate S4-35, which is deprotected with TFA or tetrabutylammonium fluouride (TBAF) to give diamine S4-36.

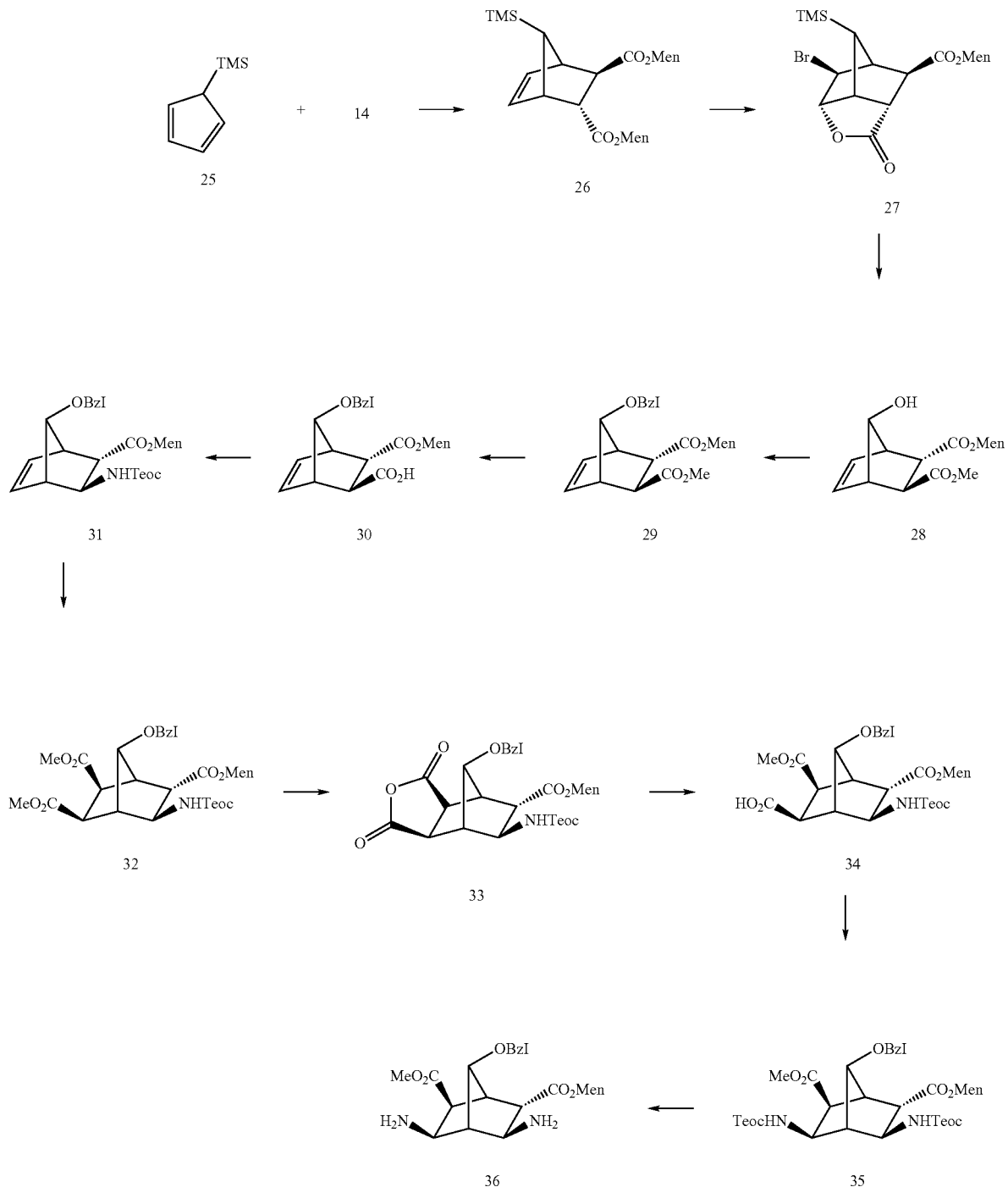

SCHEME 4

Another approach to this class of synthons is outlined in Scheme 5. Benzyl alcohol opening of S3-19 in the presence of quinidine gives S5-37 in high enantiomeric excess. Iodolactonization followed by NaBH4 reduction gives lactone S5-39. Treatment with NaOMe liberates the methyl ester and the free alcohol to generate S5-40. Trans-formation of the alcohol S5-40 to the inverted t-butyl carbamate protected amine S5-41 is accomplished in a one-pot reaction by azide deplacement of the mesylate S5-40 followed by reduction to the amine, which is protected with di-tert-butyl dicarbonate. Hydrogenolytic cleavage of the benzyl ester and epimerization of the methyl ester to the exo configuration is followed by protection of the free acid with benzyl bromide to give S5-44. Saponification of the methyl ester followed by a trimethylsilylethanol quenched Curtius reaction

SCHEME 5

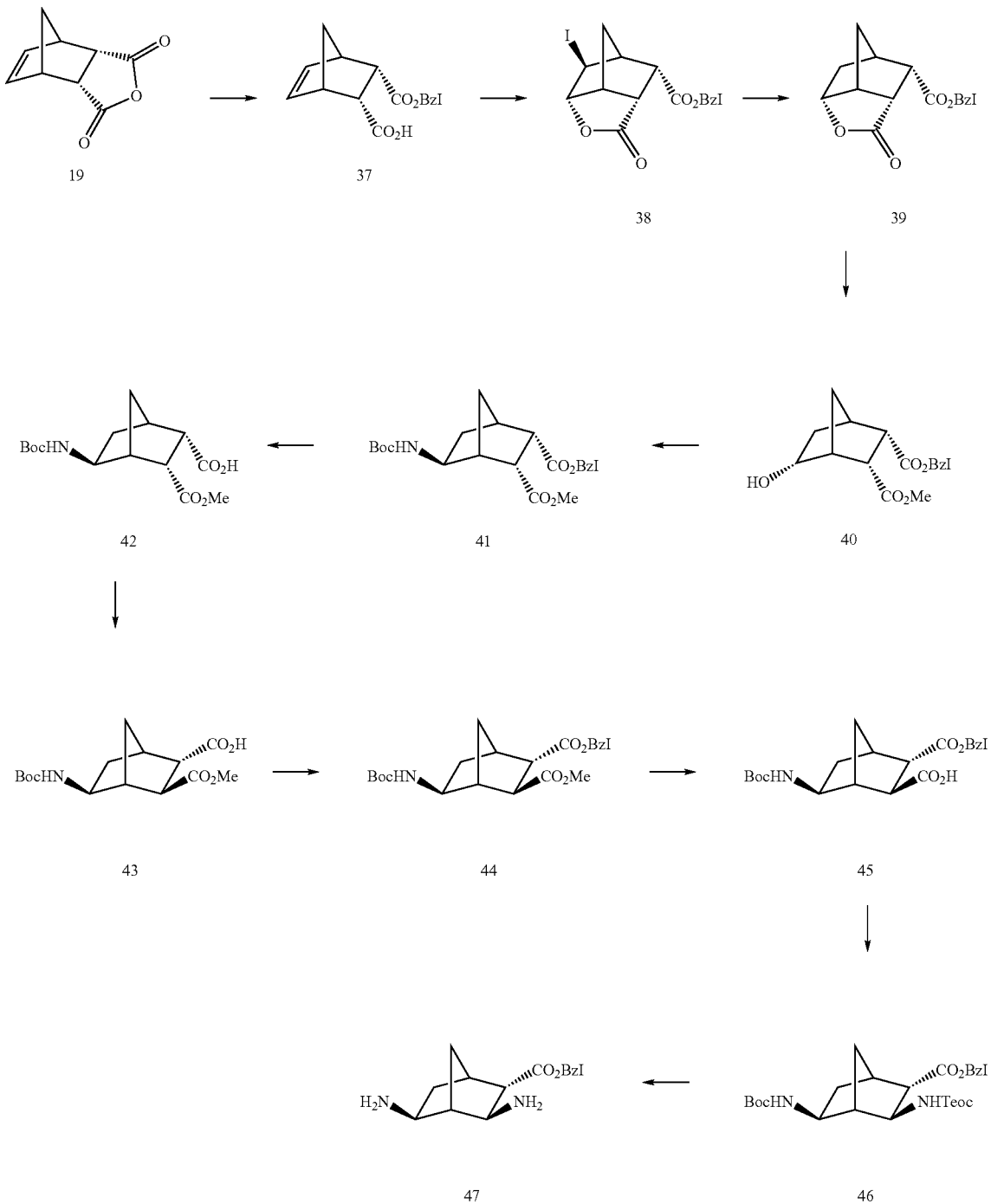

gives the biscarbamate S5-46, which is cleaved with TFA to give the desired diamine S5-47.

exo,endo-1,3-Diaminonorbornane Synthons

An approach to this class of synthons is outlined in Scheme 6. p-Methoxybenzyl alcohol opening of norbornene anhydride S3-19 in the presence of quinidine gives monoester S6-48 in high enantiomeric excess. Curtius reaction of the free acid gives protected all endo monoacid-monoamine S6-49. Biscarbonylation and anhydride formation gives exo-monoanhydride S6-51. Selective methanolysis in the presence of quinine gives S6-52. A trimethylsilylethanol quenched Curtius reaction gives biscarbamate S6-53. Epimerization of the two esters results in the more sterically stable S6-54. Cleavage of the carbamate groups provides synthon S6-55.

SCHEME 6

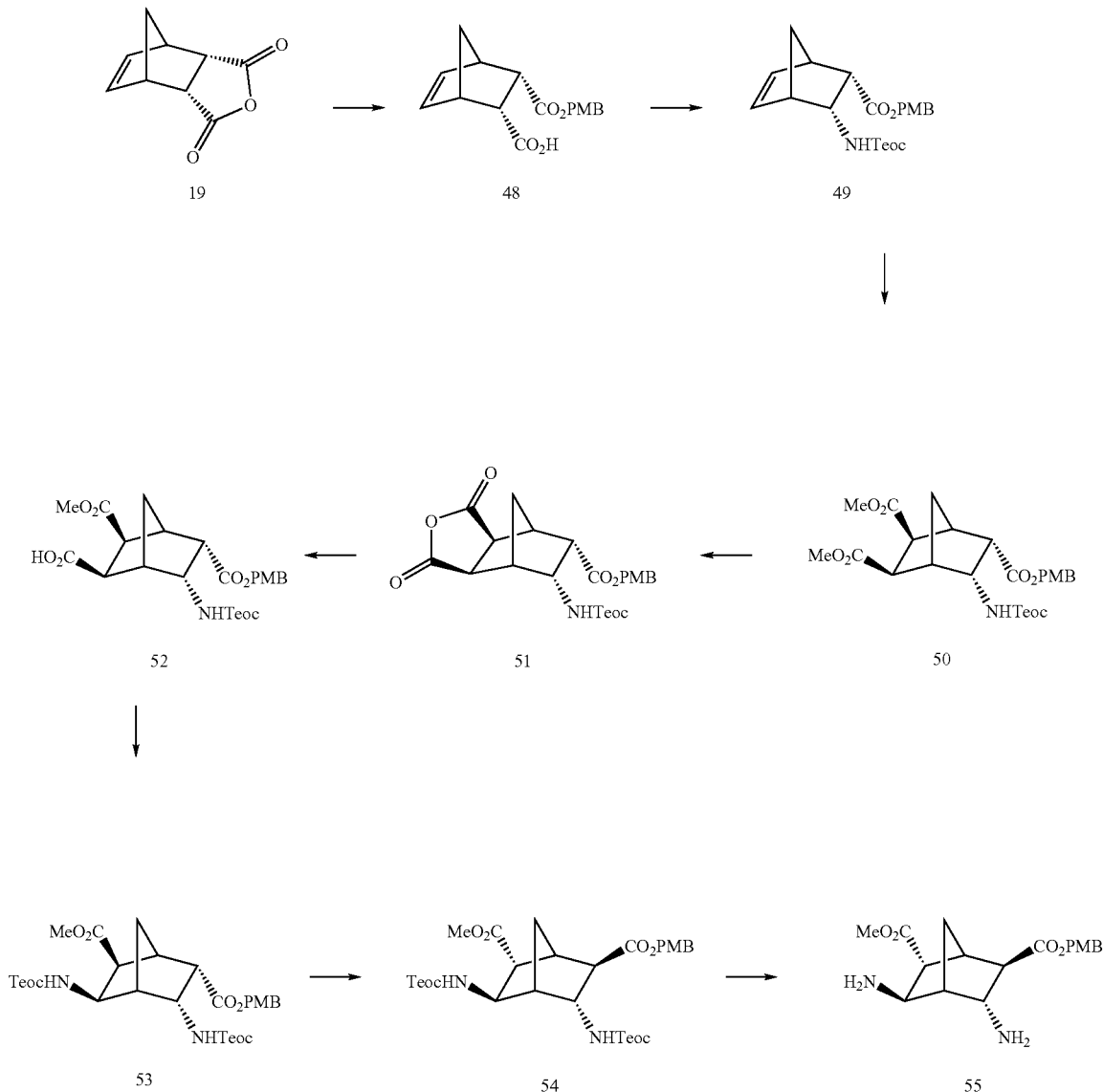

Amphiphilic Modules

Once the desired synthons are in hand, the next step is to connect them to one another through linkers to form the amphiphilic modules of this invention. This can be accomplished in a concerted or stepwise fashion.

A concerted module synthesis requires two synthons, each of which is substituted with at least two functional groups. The groups are selected such that a functional group "A" bonded to one of the synthons can react only with one functional group, "A*" on the other synthon. Likewise, the other functional group, "B," on the first synthon can react only with "B*" on the other synthon. When the synthons are combined under appropriate conditions, a chain of alternating synthons will form until an "A" (or "B") on the last synthon to be added to the chain encounters an "A*" (or "B*") on the first synthon, which will result in the creation of a ring of synthons, i.e., a module. Scheme 7 illustrates a concerted module synthesis.

1,2-Diaminocyclohexane, S7-1, is a synthon in which A and B are the same, i.e., amino groups. Likewise, 2,6-diformyl-4-dodec-1-ynylphenol, S7-2, is a synthon in which A* and B* are the same, i.e., formyl groups. Under the proper conditions, A and B will react with A* and B* to form imine linkers. The hexamer is the product shown below; it is in fact the thermodynamic product. However, the tetramer and octamer may also be formed depending on the reactions conditions. In fact, by appropriate choice of reaction conditions including, without limitation, synthon concentrations, solvent, reaction temperature and reaction time enhanced yields of various sized rings can be realized.

SCHEME 7

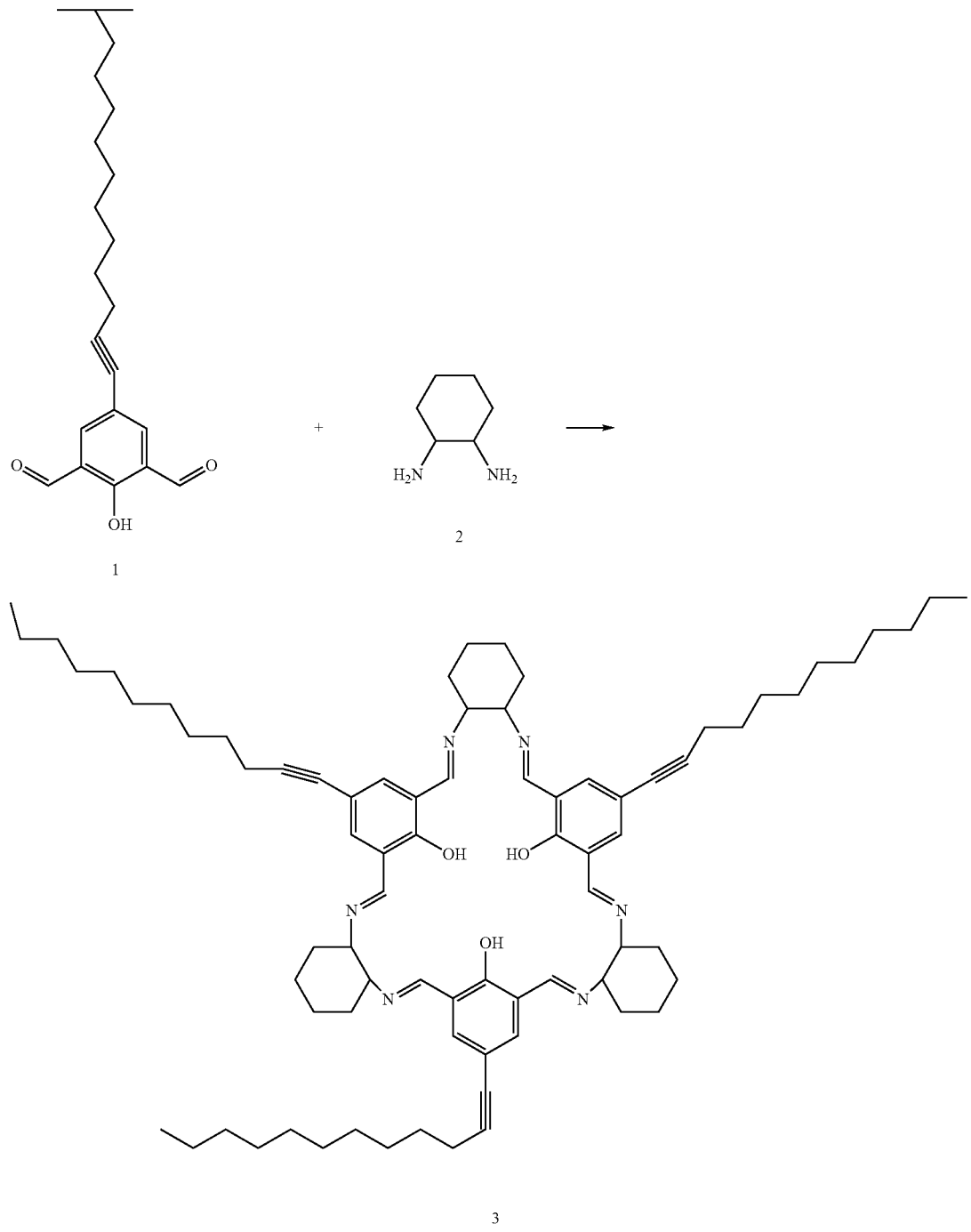

The imine groups of S7-3 can be reduced, e.g. with sodium borohydride, to give amine linkers. If the reaction is carried out using 2,6-di(chlorocarbonyl)-4-dodec-1-ynylphenol instead of 2,6-diformyl-4-dodec-1-ynylphenol, the resulting module will contain amide linkers. Similarly, if 1,2-dihydroxycyclohexane is reacted with 2,6-di(chlorocarbonyl)-4-dodec-1-ynylphenol, the resulting module will contain ester linkers. Many such concerted module syntheses will become apparent to those skilled in the art based on the disclosures herein; all such syntheses are within the scope of this invention.

The stepwise synthesis of modules is somewhat more versatile. A first synthon is substituted with one protected and one unprotected functional group. By "protected" is meant that a functional group is substituted with a readily removable entity that, while bonded to the functional group, prevents the group from entering into the reactions it normally would.

A second synthon is provided that is substituted with an unprotected functional group that will react under appropriate conditions with the unprotected functional group on the first synthon to give a dimer. The second synthon is also substituted with another functional group that is either protected or that will not react under the dimer-forming conditions. The dimer, which may be isolated and purified or used directly in the next step, is then contacted with a third synthon, which also carries two functional groups, only one of which is capable or reacting with the remaining functional group of the second synthon. This forms a trimer. The trimer is reacted with a fourth synthon to form a tetramer and so on until the desired number of synthons has been added to the chain. A last synthon to be added to the chain is substituted with a functional group that is capable of reacting only with the second functional group, after it is deprotected, of the first synthon. A ring of synthons, that is, a module of this invention, will thus be formed. The stepwise synthesis is more time consuming and difficult to perform but the choice of synthons is virtually limitless and permits much greater diversity in the structure of the amphiphilic modules. Scheme 8 illustrates a step-wise synthesis of module SC8-1.

Compound S8-2 is reacted with SC8-3, in which the phenol is protected as the benzyl ether and the nitrogen is shown as protected with a group "P," which can be any of a large number of protecting groups well-known in the art, in the presence of methanesulfonyl chloride (Endo, K.; Takahashi, H. *Heterocycles*, 1999, 51, 337), to give S8-4. Removal of the N-protecting group give the free amine S8-5, which can be coupled with synthon S8-6 using any standard peptide coupling reaction such as BOP/HOBt to give S8-7. Deprotection/coupling is repeated, alternating synthons S8-3 and S8-6 until a linear construct with eight residues is obtained. The remaining acid and amine protecting groups on the 8-mer are removed and the oligomer is cyclized using standard procedures (e.g., Caba, J. M., et al., *J. Org. Chem.*, 2001, 66:7568 (PyAOP cyclization) and Tarver, J. E. et al., *J. Org. Chem.*, 2001, 66:7575 (active ester cyclization). The R group may be any functional group that is desired in the target module or it can be a link to a solid support such as a Wang resin. Using such a solid support might simplify the procedure by obviating purification of intermediates along the way. It is even be possible to do the final cyclization in a solid phase mode. In fact, a "safety-catch linker" approach (Bourne, G. T., et al., J. *Org. Chem.*, 2001, 66:7706) might be used to obtain cyclization and resin cleavage in a single operation.

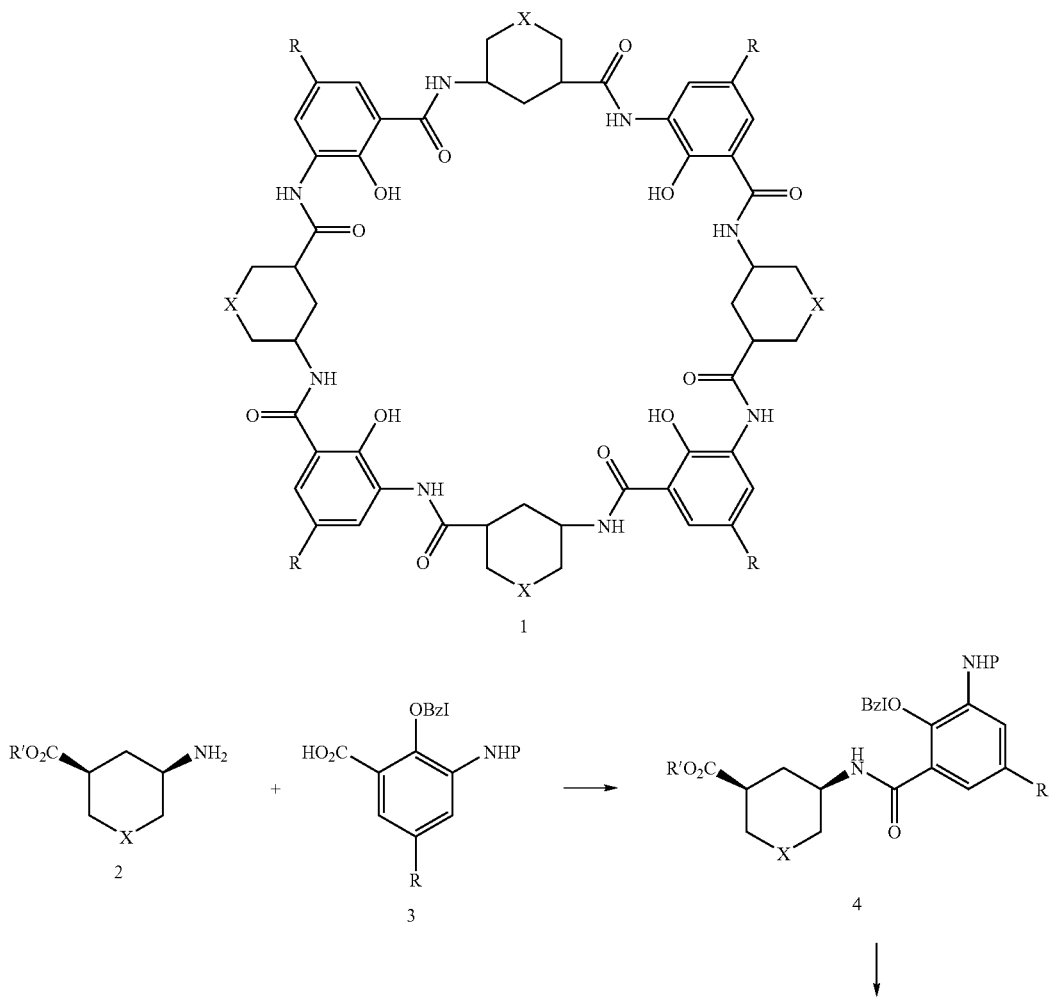

SCHEME 8

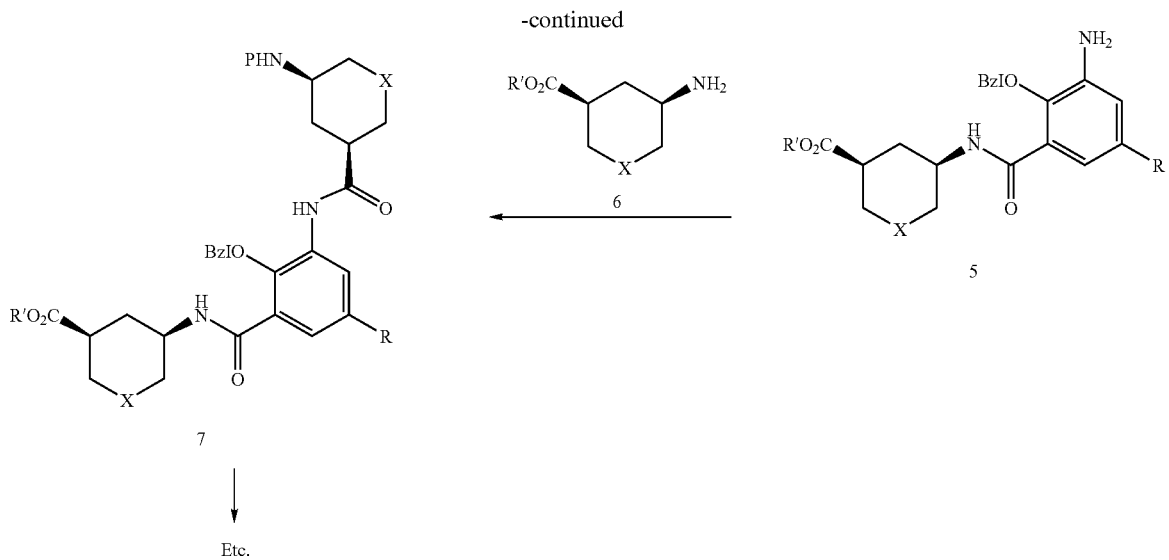

Module Pores

In a presently preferred embodiment of this invention, the ring of synthons; i.e., the module, defines a cavity or pore in the module. As noted previously, in a presently preferred embodiment of this invention the pore is a nanopore. The size of the pore will determine the size of molecules that can pass through the module. Of course, size need not be the sole determinant of what will be able to pass through a pore. Ionic, chelating or coordinating moieties, moieties that render the interior of the pore more or less hydrophilic, etc., can be disposed within or proximate to a pore to provide an additional means of control over the nature of molecules that will pass through. Moieties can be placed within pores as part of the synthons initially or they can be added later by various derivatization reactions. For example, module S7-1 could be reacted with $ClC(O)(CH_2)_2C(O)OCH_2CH_3$ to convert the phenol groups to succinyl esters.

The size of a pore will depend on the nature of the synthons used, the number of synthons in a module and the nature of the linkers. A first approximation to pore size can be obtained using quantum mechanical (QM) and molecular mechanical (MM) computations.

Figure 1B:
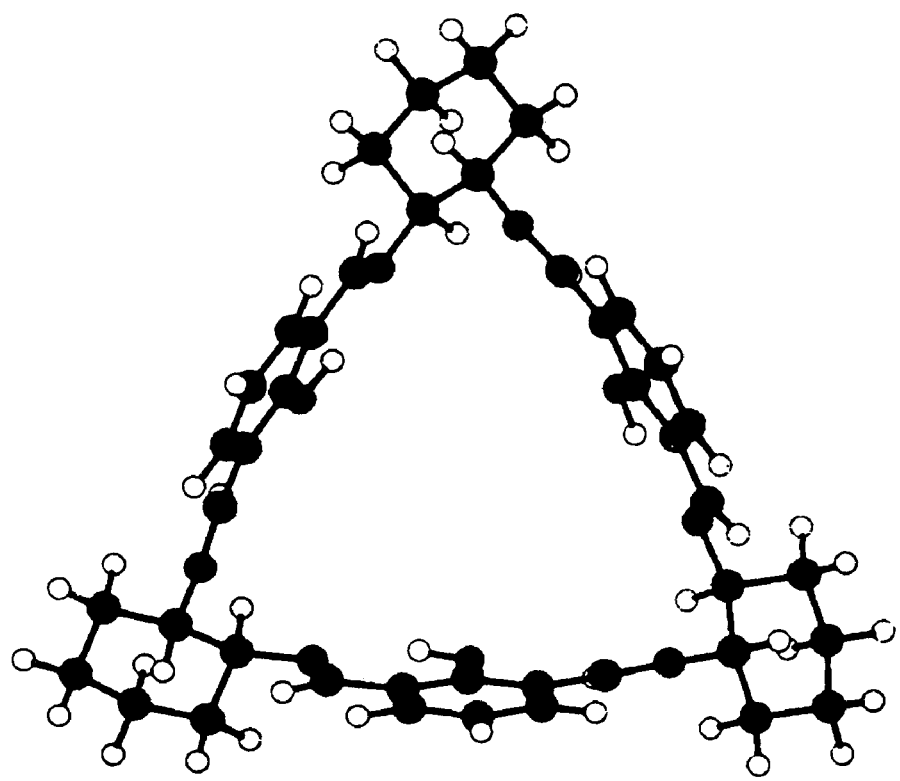
Figure 1C:
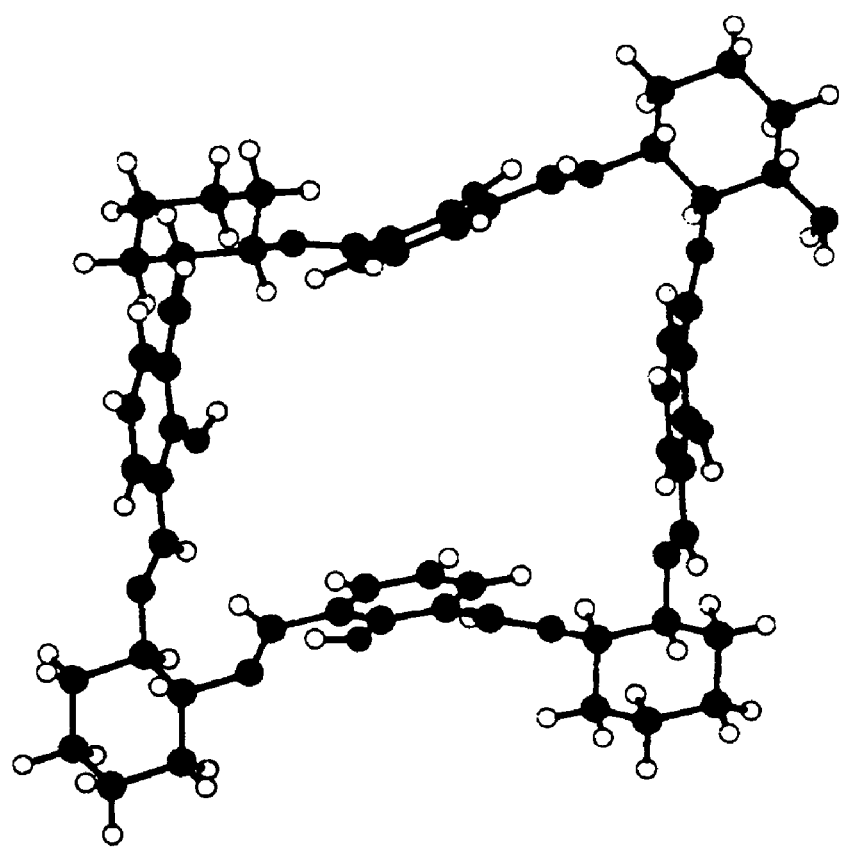

As the basis for the computations, modules were assumed to constitute two synthons, "A" and "B," and all linkers were assumed to be the same. As it turns out, the modules approximate various regular polyhedrons quite well depending on the number of synthons in the module. Thus, when stereochemically defined modules comprised of 4, 6, and 8 synthons were subjected to MM3 energy minimization, the structures shown in FIGS. 1A-C, which are at, or very near, the thermodynamic energy minimums were obtained. As can be seen, the tetramer essentially describes a parallelogram, the hexamer an equilateral triangle and the octamer a rhombus. For the purposes of QM and MM computations, root mean square deviations in the pore areas were computed over the dynamic runs.

For quantum mechanical computations, each module was first optimized using the MM+force field approach of Allinger (JACS, 1977, 99:8127) and Burkert, et al., (Molecular Mechanics, ACS Monograph 177, 1982). They were then re-optimized using the AM1 Hamiltonian (Dewar, et al., JACS, 1985, 107:3903; Dewar, et al., JACS, 1986, 108:8075; Stewart, J. Comp. Aided Mol. Design, 1990, 4:1). To verify the nature of the potential energy surface in the vicinity of the optimized structures, the associated Hessian matrices were computed using numerical double differencing.

As for MM computations, the OPLS-AAforce field approach (Jorgensen, et al., JACS, 1996, 118:11225) was used. For imine linkers, the dihedral angle was confined to 180°±10°. The structures were minimized and equilibrated for one picosecond using 0.5 femtosecond time steps. Then a 5 nanosecond dynamics run was carried out with a 1.5 femtosecond time step. Structures were saved every picosecond. The results are shown in Tables 2 and 3.

In Table 2, Synthon "A" is 2,6-benzenediol while in Table 3, synthon "A" is 2,7-naphthanediol. Synthon B is shown in the left-hand column. Nanopore sizes derived from QM and MM computations for various linkers and module size are shown.

TABLE 2

| SYNTHON B | TETRAMER QM | TETRAMER MM | HEXAMER QM | HEXAMER MM | OCTAMER QM | OCTAMER MM |
|---|---|---|---|---|---|---|
| trans-1,2-cyclohexane | | | imine (trans) 14.3 Å$^2$ | Imine (trans) 13.2 ± 1.4 Å$^2$ | | |
| trans-1,2-cyclohexane | | | Acetylene 14.3 Å$^2$ | | | |
| trans-1,2-cyclohexane | | | Amine 23.1 Å$^2$ | Amine 13.9 ± 1.9 Å$^2$ | | |

TABLE 2-continued

| SYNTHON B | TETRAMER QM | TETRAMER MM | HEXAMER QM | HEXAMER MM | OCTAMER QM | OCTAMER MM |
|---|---|---|---|---|---|---|
| trans-1,2-cyclohexane | | | Amide 19.7 Å$^2$ | Amide 17.5 ± 2.0 Å$^2$ | | |
| trans-1,2-cyclohexane | | | Ester 18.9 Å$^2$ | Ester 19.6 ± 2.0 Å$^2$ | | |
| Equatorial-1,3-cyclohexane | | | imine (trans) 18.1 Å$^2$ | Imine (trans) 21.8 ± 1.6 Å$^2$ | imine (trans) 66.2 Å$^2$ | Imine (trans) 74.5 ± 7.7 Å$^2$ |
| Equatorial-1,3-cyclohexane | | | Amine 14.7 Å$^2$ | Amine 19.9 ± 2.6 Å$^2$ | | |
| Equatorial-1,3-cyclohexane | | | Amide 24.8 Å$^2$ | Amide 21.7 ± 1.8 Å$^2$ | | |
| Equatorial-1,3-cyclohexane | | | Ester 22.9 Å$^2$ | Ester 22.8 ± 2.4 Å$^2$ | | |
| Equatorial-3-amino-cyclohexene | imine (trans) oxygen-xygen distance 2.481 Å | imine (trans) oxygen-oxygen distance 3.7 ± .3 Å | imine (trans) 18.4 Å$^2$ | Imine (trans) 21.0 ± 1.5 Å$^2$ | imine (trans) 56.7 Å$^2$ | Imine (trans) 60.5$^+$ – 8.3 Å$^2$ |
| trans-1,2-pyrrolidine | | | imine (trans) 10.4 Å$^2$ | Imine (trans) 9.2 ± 1.4 Å$^2$ | | |
| Equatorial-1,3-piperidine | | | imine (trans) 19.2 Å$^2$ | Imine (trans) 20.9 ± 1.1 Å$^2$ | | |
| Endo-exo-1,2-bicycloheptane | | | imine (trans) 11.1 Å$^2$ | Imine (trans) 14.1 ±+– 11 Å$^2$ | | |
| Endo-endo-1,3-bicycloheptane | | | imine (trans) 18.8 Å$^2$ | Imine (trans) 20.7 ± 1.4 Å$^2$ | | |
| Endo-exo-1,3-bicycloheptane | | | Imine 19.5 Å$^2$ | Imine 10.1 ± 4.9 Å$^2$ | | |
| Equatorial-1,3-cyclohexane | | | Amine 9.8 Å$^2$ | Amine 9.9 ± 2.4 Å$^2$ | | |
| Endo-endo-1,3-bicyclooctene | | | imine (trans) 18.9 Å$^2$ | Imine (trans) 21.6 ± 1.5 Å$^2$ | | |
| Endo-exo-1,3-bicyclooctene | | | imine (trans) 15.6 Å$^2$ | Imine (trans) 18.7 ± 1.6 Å$^2$ | | |
| Equatorial-3,9-decalin | | | imine (trans) 35.4 Å$^2$ | Imine (trans) 40.0 ± 2.2 Å$^2$ | | |

TABLE 3

| SYNTHON B | HEXAMER QM | HEXAMER MM |
|---|---|---|
| Trans-1,2-cyclohexane | imine (trans) 23.5 Å$^2$ | imine (trans) 25.4 ± 4.9 Å$^2$ |
| Endo-endo-1,3-bicycloheptane | imine (trans) 30.1 Å$^2$ | imine (trans) 30.0 ± 3.6 Å$^2$ |

The computed nanopore size was tested and confirmed experimentally using a voltage-clamped bilayer procedure. Modules are inserted into a lipid bilayer, for example, the bilayer formed by phosphatidylcholine and phosphatidylethanolamine. On one side of the bilayer is placed a solution containing a test cationic species. On the other side is a solution containing an cationic species known to be able to pass through a pore of the calculated size. Anions required for charge neutrality are selected such that they will not pass through pores of the calculated size. When a positive potential is created in the solution on the side of the lipid bilayer containing the test species, if the test cations are of such a size that they cannot pass through the pores in the modules, no current will be detected. The voltage is then reversed to create a positive potential on the side of the lipid bilayer having the solution containing the cationic species known to be able to traverse the pore. Observation of the expected current confirms the integrity of the membrane and the availability of the pores as transporters of cations of that size (and, of course, smaller) across the membrane.

Using the above technique, a hexamneric module comprised of R,R-1,2-transdiaminohexane and 2,6-diformal-4-(1-dodec-1-ynyl)phenol as the synthons and imine groups as the linkers (the first module in Table 2) was inserted in the above-described lipid bylayer. A number of different ionic species were then tested to see if they could traverse the pore. The results are shown in Table 4.

TABLE 4

| Ionic species | Calculated van der Waals radius of ionic species (VdW) (in Angstroms, Å) | Calculated van der Waals radius of ionic species with one water shell | Does ionic species pass through nanopore? |
|---|---|---|---|
| Na$^+$ | 1.0 | 2.2 | Yes |
| K$^+$ | 1.3 | 2.7 | Yes |
| Ca$^{2+}$ | 1.0 | 2.7 | Yes |
| Mg$^{2+}$ | 0.7 | 2.8 | Yes |
| NH$_4^+$ | 1.9 | 2.9 | Yes |
| Cs$^+$ | 1.7 | 3.0 | Yes |
| MeNH$_3^+$ | 2.0 | 3.0 | Yes |
| EtNH$_3^+$ | 2.6 | 3.6 | No |
| NMe$_4^+$ | 2.6 | 3.6 | No |
| Aminoguanidinium | 3.1 | 4.1 | No |
| NEt$_4^+$ | 3.9 | 4.4 | No |
| Choline | 3.8 | 4.8 | No |
| Glucosamine | 4.2 | 5.2 | No |

From Table 4 it can be deduced that the cut-off for passage through the pore in the selected module is a van der Waals radius of somewhere between 2.0 and 2.6 Å. In Table 2, the QM and MM computed nanopore sizes are given as areas. Using the equation for area of a circle, $A=\pi r^2$, the computed area of the pore in the first module of Table 1, 14.3 Å$^2$, gives a value for r of 2.13 Å. Thus, ions having van der Waals radii of less than 2.13 would be expected to traverse the pore and those with larger radii would not. This is exactly what was observed. $CH_3NH_3^+$, having a radius of 2.0 Å, passed through the pore while $CH_3CH_2NH_3^+$, with a radius of 2.6 Å, did not. Without being held to a particular theory, the observed ability of hydrated ions to pass through the pore may be due to partial dehydration of the species at the pore with water molecules and ions passing through single file and then re-coordinating on the other side. In addition, the ions may coordinate with atoms of the pore during the process.

Arrays of Modules

Modules of the present invention can be arranged in a virtually infinite number of ways. They can be randomly distributed in a plane defined by the plane of the ring of synthons without any means of controlling the location of individual modules. The randomly distributed modules may be connected to one another to form a somewhat more robust array. On the other hand, the modules may be arranged in an ordered array such as, without limitation, a close-packed or a dendridic array. In a presently preferred embodiment of this invention, a two-dimensional close-packed planar array of modules is constructed.

Two-Dimensional Close-Packed Planar Arrays

It is, of course, understood that the arrays cannot technically be two-dimensional because atoms have volume. Furthermore, functional groups attached to the modules may extend above and below the plane defined by the rings of synthons that comprise the modules that, in turn, comprise the arrays. Thus, as used herein, "two-dimensional" refers simply to the fact that presently preferred arrays of this invention are one module thick.

By "planar" is meant that the modules are disposed in a plane defined by the planes of the synthons comprising the modules.

Figure 2:
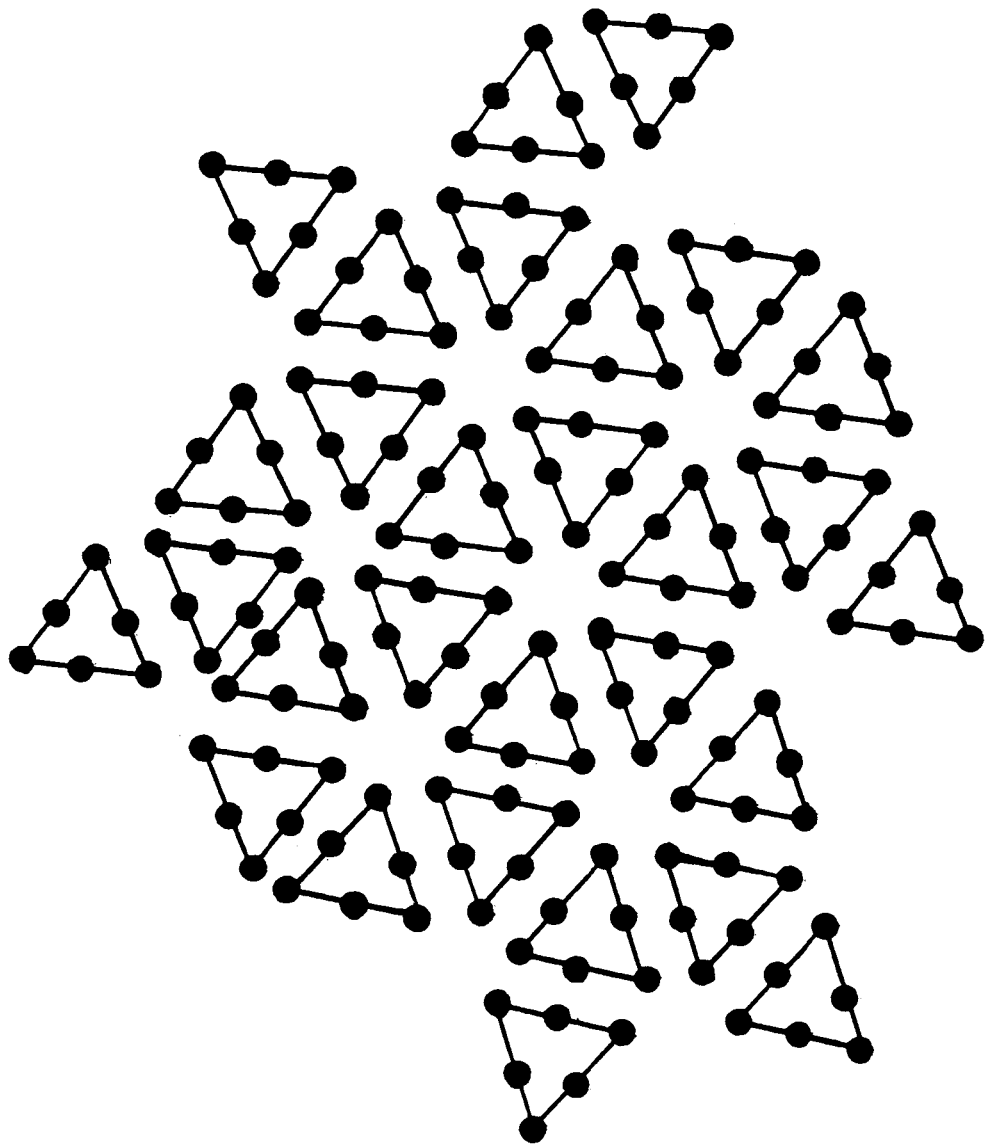
FIG. 2 depicts a close-packed two-dimensional array of hexameric modules.

As used herein, "close-packed" refers to an array in which, for a given polygonal-shaped module, the edges of the polygon fit together such that voids between the modules are minimized. For example, FIG. 2 shows a two-dimensional planar close-packed array of hexameric (i.e., essentially triangular) modules. In FIG. 2, the circles represent synthons. In FIG. 2A, the modules are shown in a close-packed array without any means of maintaining the structure. Such arrays can be formed and may have practical application. However, in most instances, to form a robust array that can withstand a variety of external forces and therefore should be more practically useful, it is preferred to connect the modules to one another. This is depicted schematically in FIGS. 2B and 2C, in which the lines between the synthons represent connectors. A "connector," as used herein, is similar to a linker in that it is the reaction product of a functional group associated with one module with a functional group associated with a second module. The term "associated" is used to signify that a connector functional group may be separated from the synthon to which it is attached by a substantially longer spacer than those used with linkers. That is, whereas functional groups comprising linkers are either bonded directly to synthons or, at most, are separated by a methylene or two, connector functional groups may be substantially remote from the synthon. For example, an acrylate double bond at the end of an 8C hydrophilic group may serve as a connector-forming functional group (see infra).

Figure 2B:
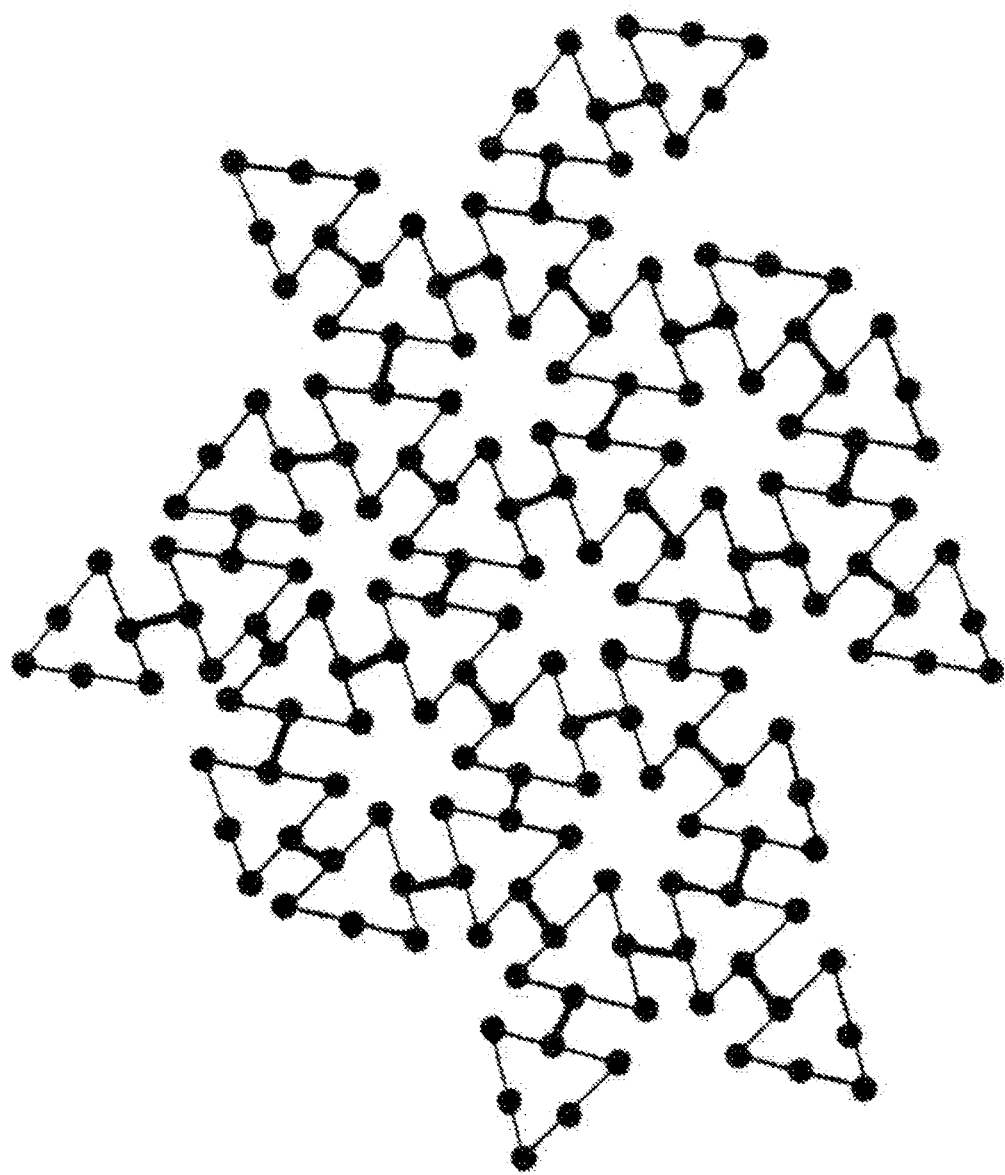
FIG. 2B show the array with one connector between each pair of adjacent
Figure 2C:
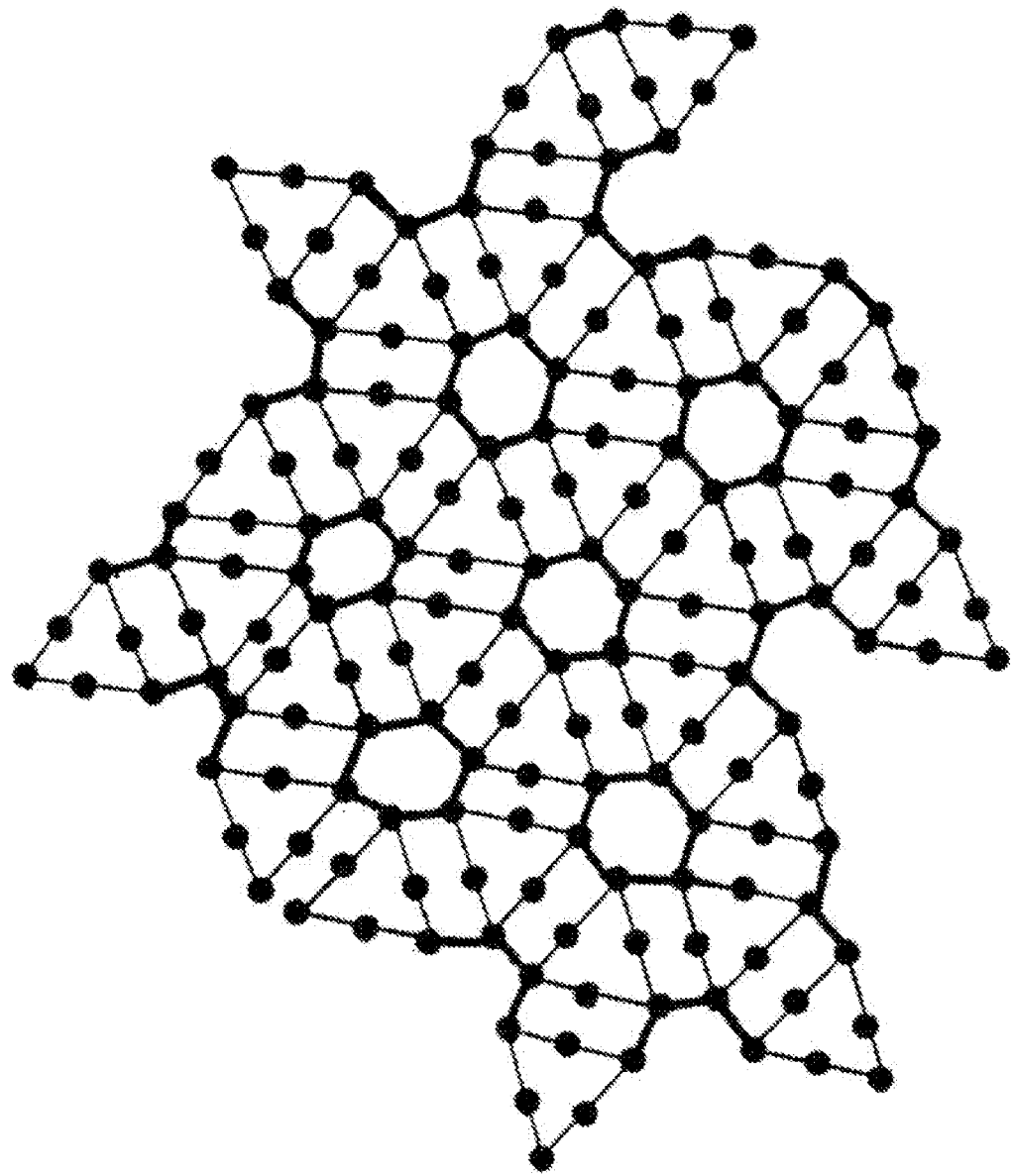
FIG. 2C shows the array with two connectors between each pair of adjacent modules.

Connectors may be formed using one or more functional group on each module. In FIG. 2B, one line is shown between adjacent modules indicating a single connector formed by the reaction of one functional group on each module. However, it is possible to have more than one connector between the same two modules, as shown in FIG. 2C, wherein two functional groups on each module have reacted to from connectors.

The connector functional groups may be bonded to a synthon along an edge of a module (FIG. 2B) or at an apex (triangle/hexamer, FIG. 2C) or at a corner (tetramer, octamer). Of course, any combination of these may also be employed.

Figure 6:
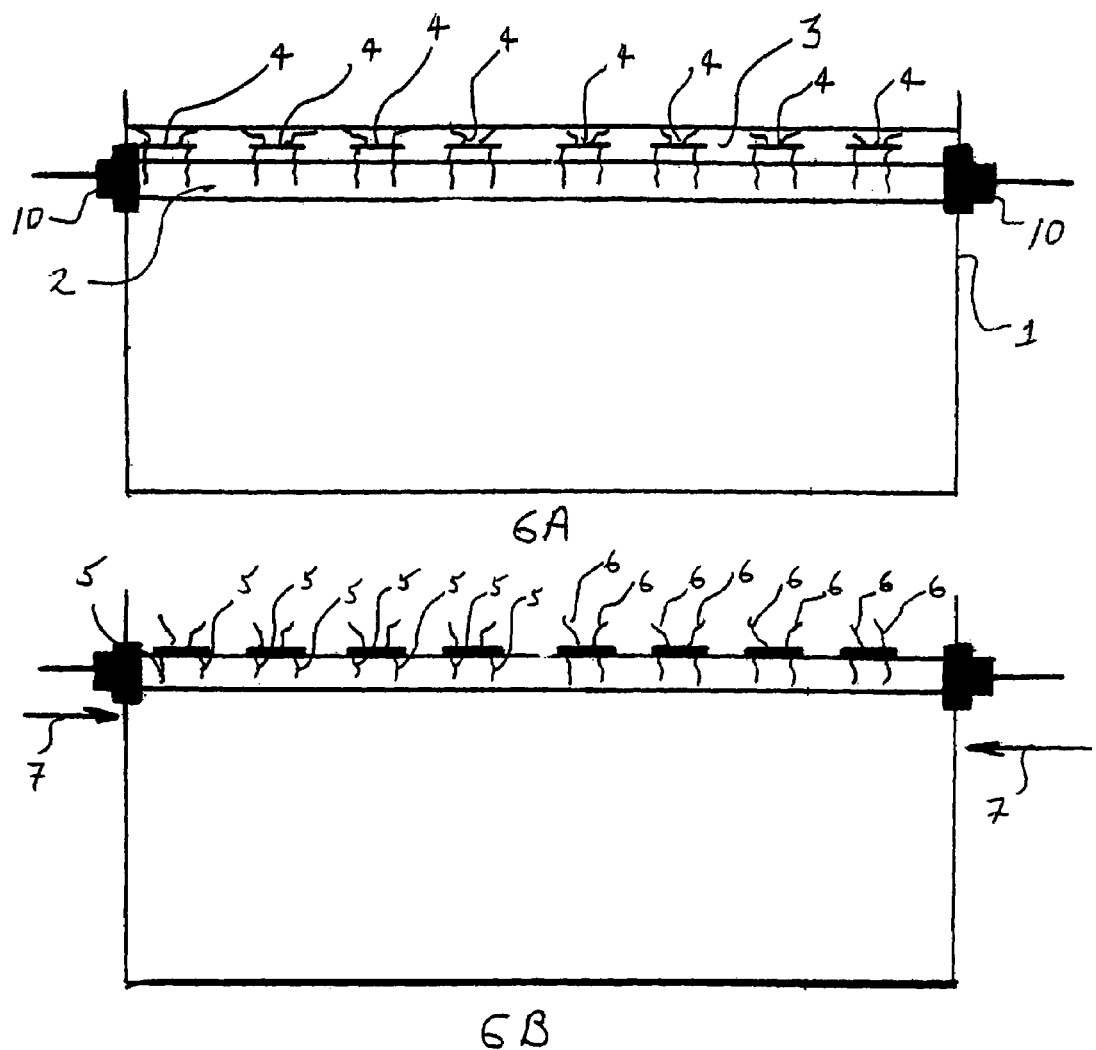
FIG. 6 depicts the preparation of a nanomembrane. The figures are cartoon representations only and are not intended to depict an actual Langmuir-Blodgett trough.
Figure 6C:
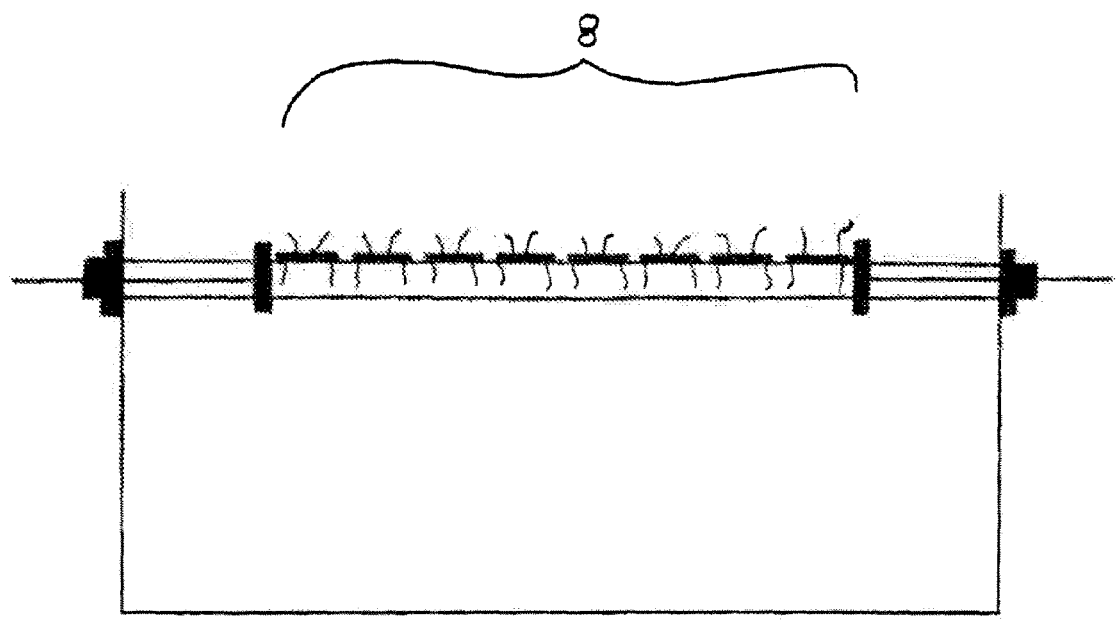
FIG. 6C shows the amphiphilic modules compressed into a close-packed array.
Figure 6D:
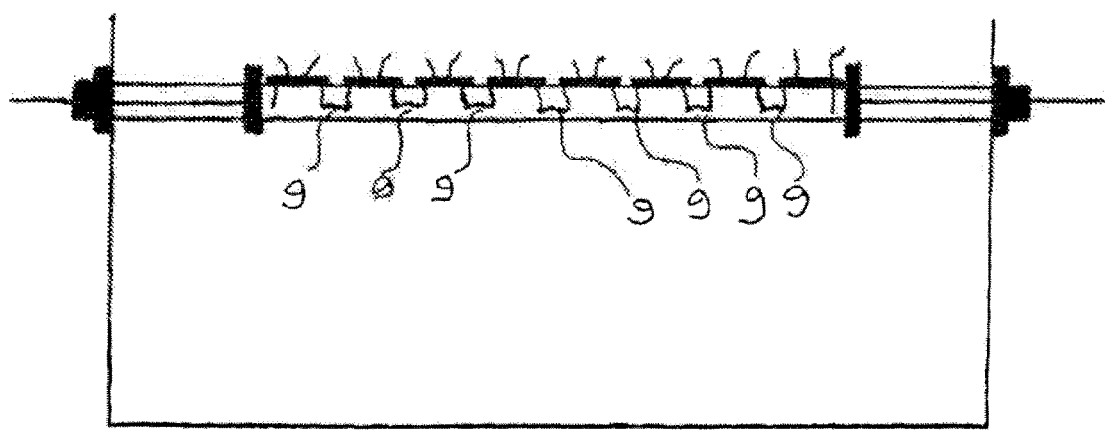
FIG. 6D shows the close-packed array in which connectors have been formed between the amphiphilic modules.

To bring the modules into close proximity such that connectors may be formed, their amphiphilicity is exploited. It is known in the art that, when placed at the interface of water and a water-immisible liquid (or air), amphiphilic molecules will orient themselves such that their hydrophilic moieties are immersed in the water layer and their lipophilic moieties are in the water-immiscible liquid layer (or extend up into the air). If pressure is applied horizontally to the monomolecular film of amphiphilic modules so formed, the modules will condense into a close-packed array, called a Langmuir film. The apparatus in which Langmuir films are created is called a Langmuir-Blodgett (L-B) trough. Langmuir films and L-B troughs are well known in the art. The following is an example of a procedure that can be employed to form a Langmuir film. It is not to be construed as limiting the scope of this invention in any way. The procedure is schematically depicted in FIG. 6.

Figure 3:
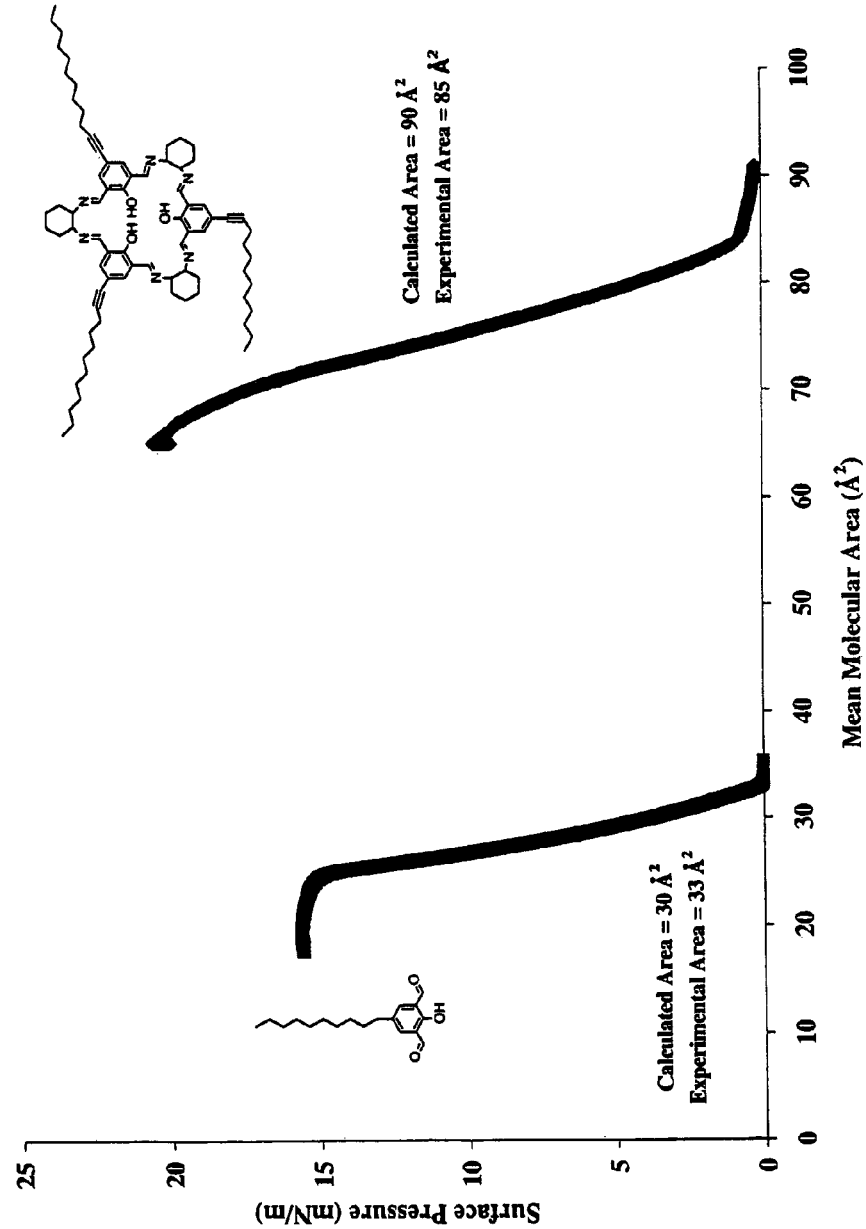
FIG. 3 is a graph of a Languir isotherm demonstrating that the modules of this invention do form mono-molecular Langmuir films.

Amphiphilic modules 4 are dissolved in HPLC-grade chloroform at a concentration of approximately 1 mg/ml. The chloroform solution 3 is applied to a water (Millipore Milli-Q) surface 2 in an L-B trough 1 (such as that marketed by KSV, Helsinki, Finland). The chloroform is allowed to evaporate, leaving the amphiphilic modules on the surface of the water with their hydrophilic groups 5 immersed in the water and their lipophilic groups 6 in the air. The temperature in the system is carefully controlled (preferably to within ±0.2° C. or better). The barriers 10 of the L-B trough are slowly compressed (1-10 mm/min). The surface pressure is monitored using an appropriate technique such as the Wilhelmy plate procedure until a sudden change in surface pressure signifies that the film has collapsed. Pressure is released until the film reforms. A plot of surface pressure as a function of the area of water surface available to each module at a constant temperature, known as the surface pressure/area isotherm, often abbreviated "isotherm," is an indicator of the monolayer properties of a material, which can confirm that a Langmuir film has in fact formed. An example of an isotherm is shown for an amphiphilic synthon and an amphiphilic module of this invention in FIG. 3. The shape of the isotherm confirms that the module does in fact form a Langmuir film on the surface of the water. Furthermore, it can be seen that the calculated water surface area required by the synthon and module when in a Langmuir film configuration agrees very well with that experimentally determined. The result of the compression of the trough is the formation of a close-packed array 8 of amphiphilic modules.

Once a Langmuir film has formed, selected functional groups will, by virtue of their pre-determined locations on the modules and the predictable alignment of the amphiphilic modules in the Langmuir film, be located in the correct relationship to one another to react and form connectors 9. As noted previously, the connector-forming functional groups may have served other purposes prior to being recruited for connector duty. For example, a functional group might be employed as part of a hydrophilic moiety to assist in the formation of a Langmuir film and then, once the film has formed, may be used to form a connector. Other multiple-use functional groups will be envisioned by those skilled in the art based on the disclosures herein and are within the scope of this invention.

A connector functional group may, as was the case with linker precursors, be covalently bonded directly to a synthon. In fact, the same functional groups shown to form linkers in Table 1 may be used to form connectors in exactly the same way. In practice, if the same functional groups are going to be used for form both linkers and connectors, those that will be used later to form connectors are blocked with protecting groups that prevent their reaction until the protecting group is removed. As with linkers, connector formation may also comprise the reaction of three or more moieties, for example, a functional group on one module, a second functional group on an adjacent module and a third external molecule. An example of this would be the Mannich reaction, discussed above with regard to linkers.

Figure 4:
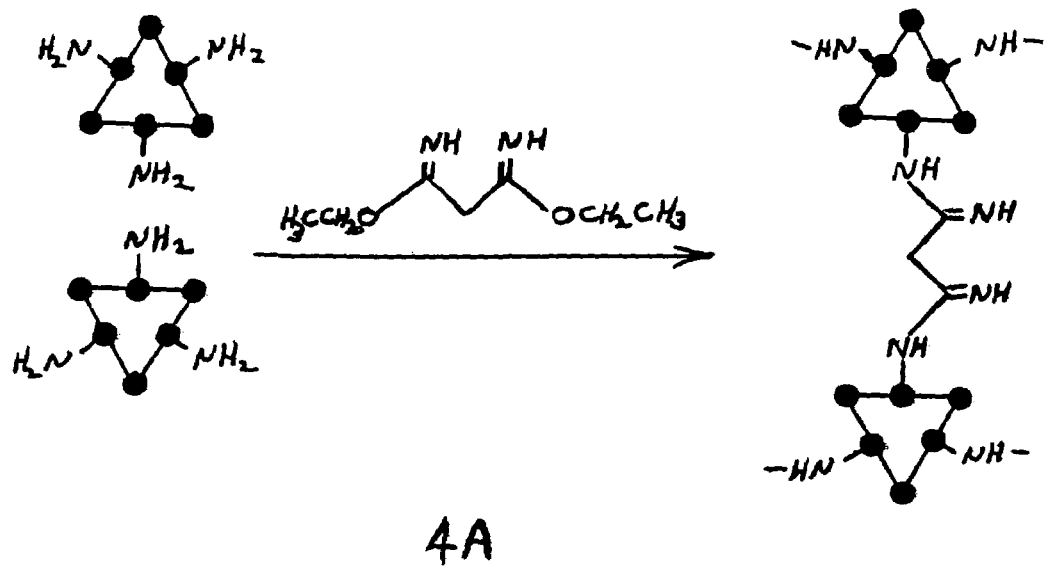
FIG. 4 depicts some presently preferred connectors and the functional groups and reactants used for their formation.
Figure 4:
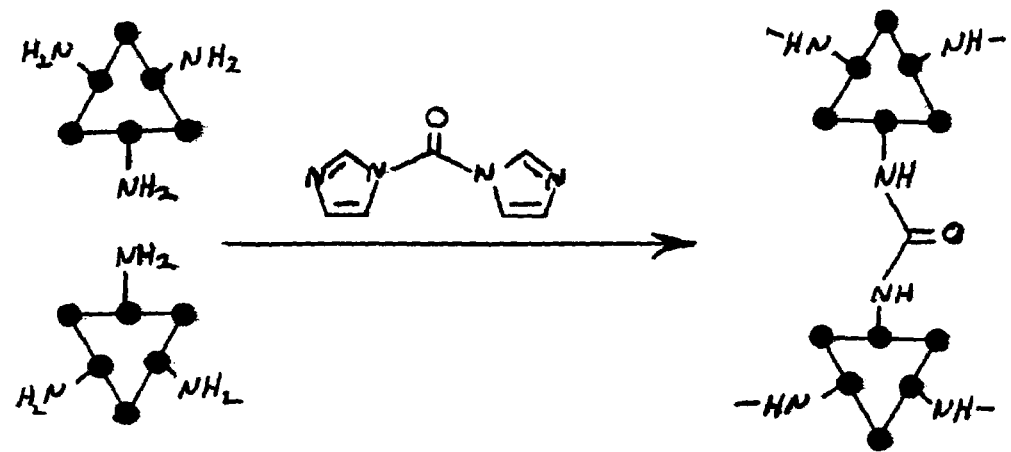

However, an even broader range of external molecules may be useful in the formation of connectors than in the formation of linkers. Some of these external molecules are shown in FIG. 4. In the figure, the modules are again shown as triangles, implying hexamers. Likewise, the circles represent synthons and the solid lines, covalent bonds that is understood, however, that the same functional groups could be used and the same connector-forming reactions carried out with any size module.

Figure 4C:
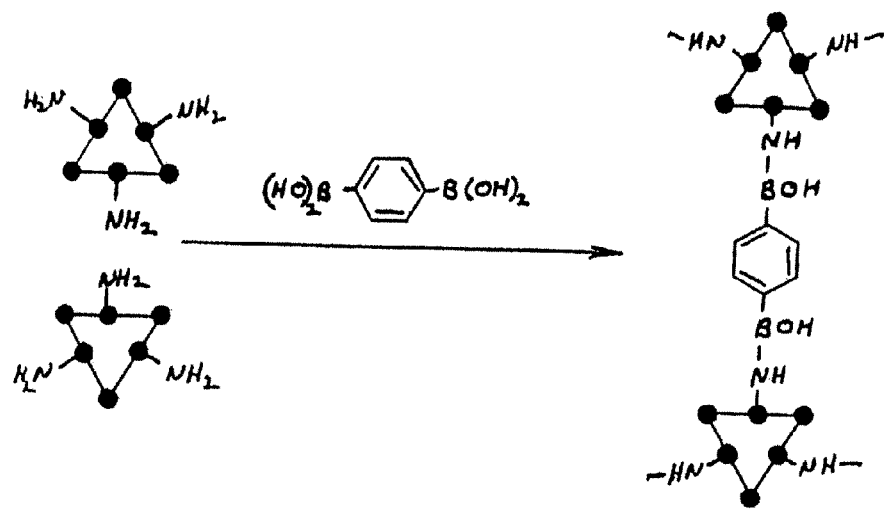
FIG. 4C shows a boronic acid amide connector.
Figure 4D:
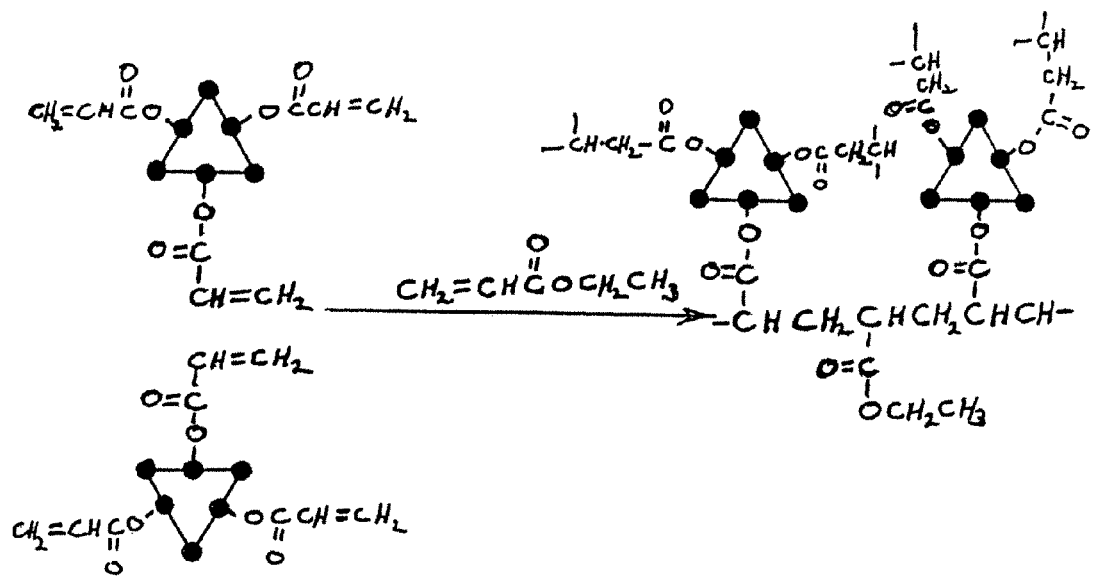
FIG. 4D shows a copolymeric connector formed by the reaction of acrylate functional groups on the synthons with external ethyl acrylate.

Thus, bisamidates (FIG. 4A), dicarbonyidiimidazoles (FIG. 4B), bisboronic acids or esters (FIG. 4C) and acrylates (FIG. 4D) may be used to form connectors. Numerous other connector-forming functional groups, reactants and reactions will become apparent to those skilled in the art based on the disclosures herein and are within the scope of this invention.

It is presently preferred, however, that the distance between modules as defined by the length of the connectors be such that the holes created between modules in the array by the connectors be smaller in size than the pores within the individual modules.

Figure 5:
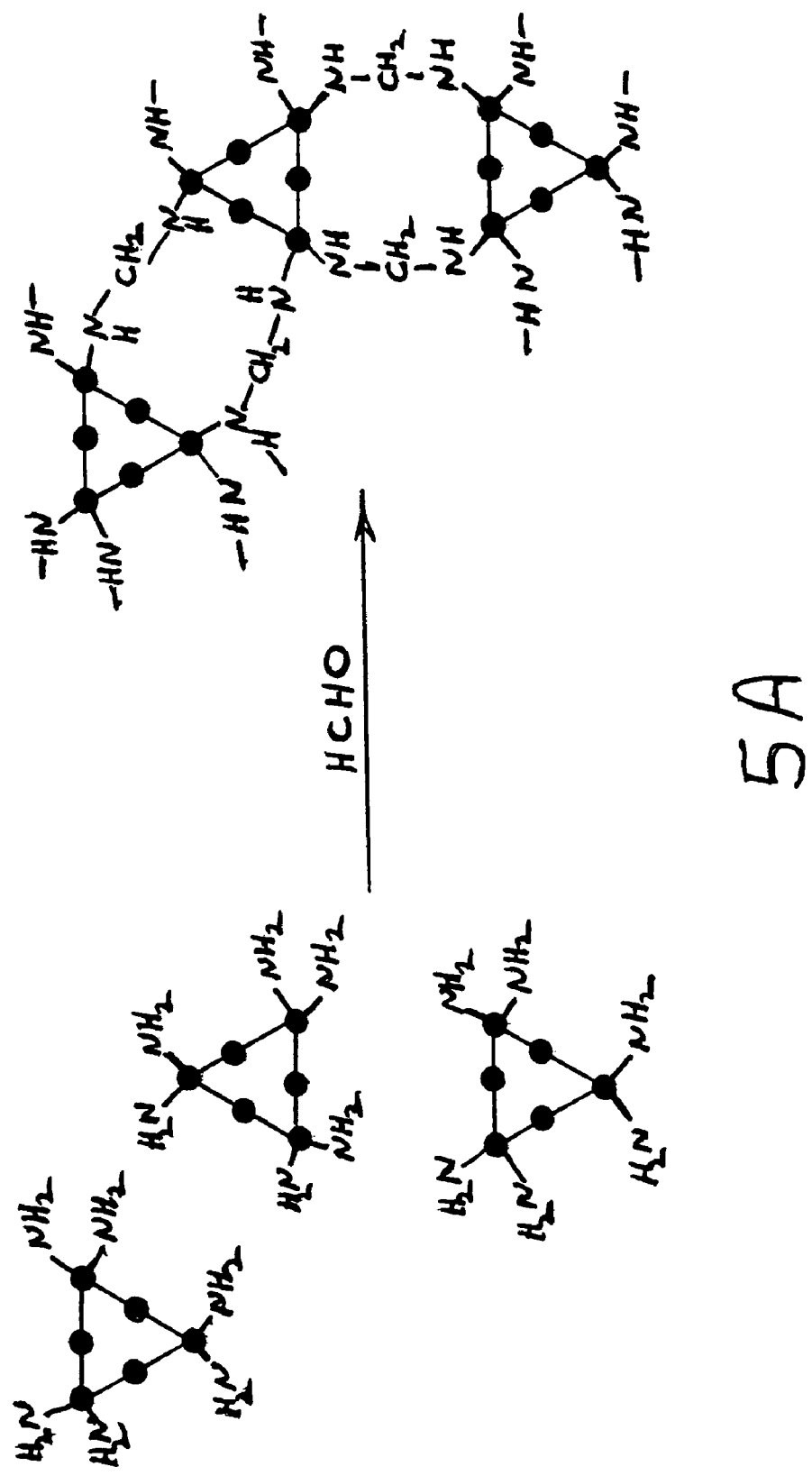
FIG. 5 depicts some additional presently preferred connectors.
Figure 5B:
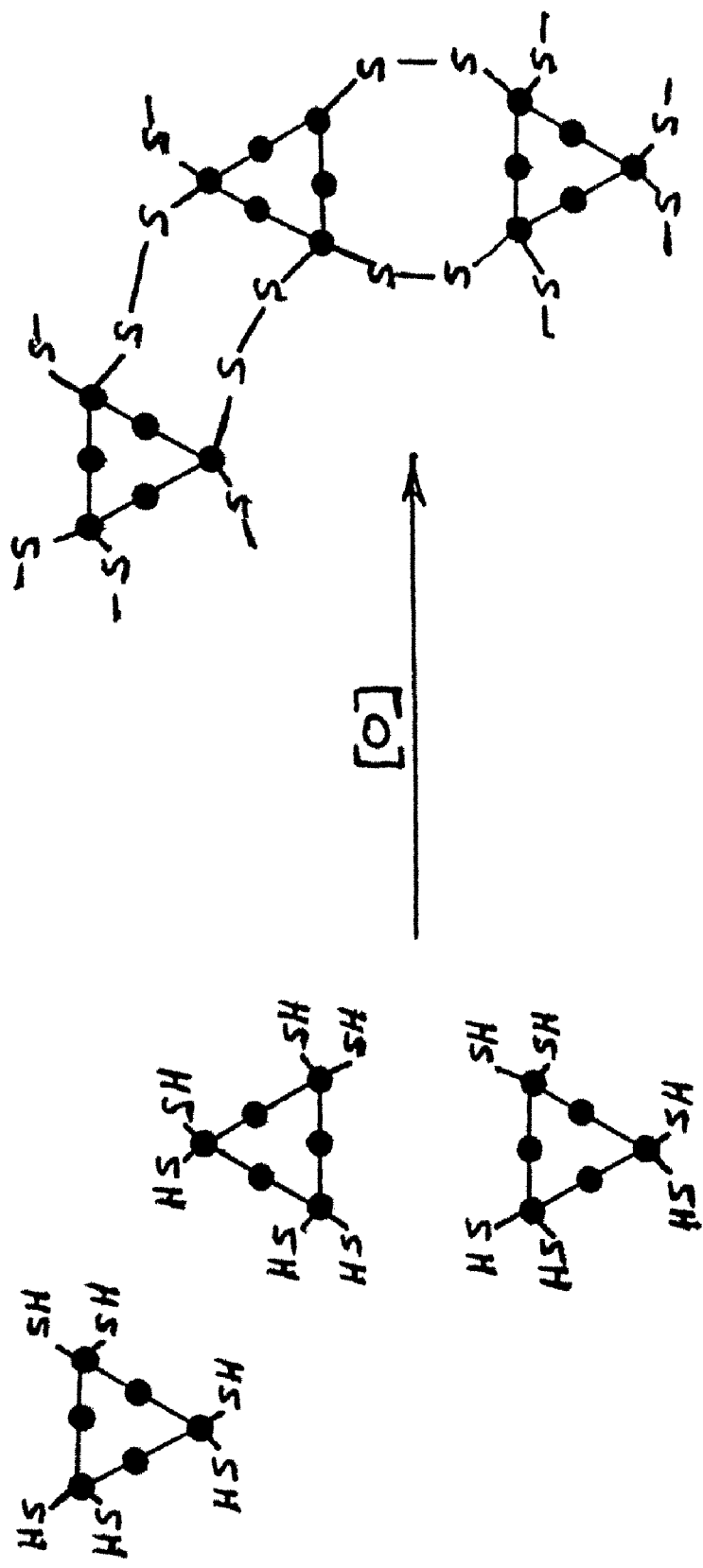
FIG. 5B shows the formation of disulfide connectors from mercaptans.
Figure 5C:
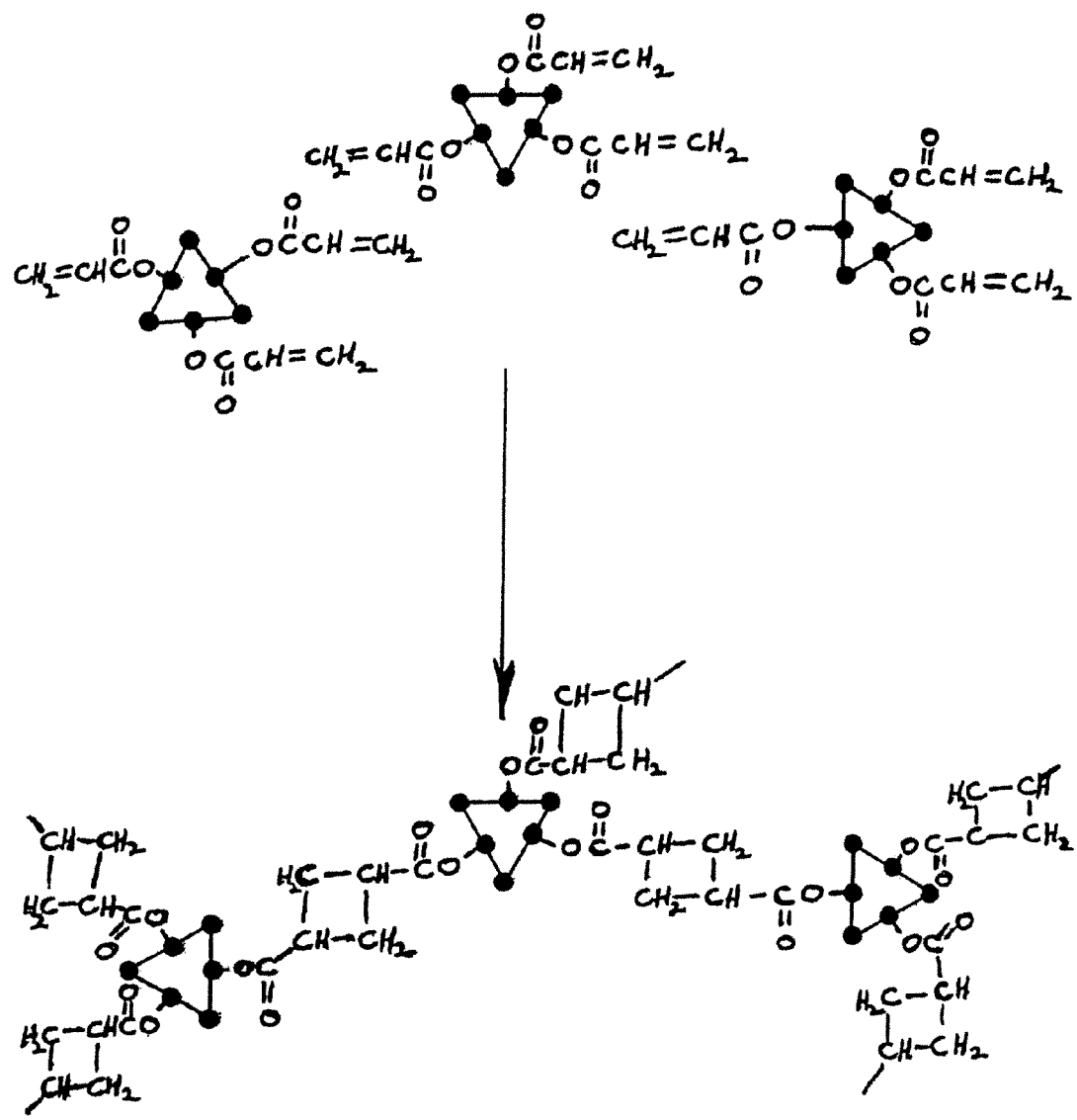
FIG. 5C shows the formation of cyclobutyl connectors by the [2+2] cycloaddition of acrylates on the synthons.

Two functional groups used to form two connectors may be bonded to the same synthon. Such an arrangement is depicted in FIG. 5. In FIG. 5A, two amino groups are bonded to the same synthon in each module. Reaction with formaldeyde gives the connectors shown, i.e., aminals. In FIG. 5B, two mercapto (—SH) groups are shown bonded to the same synthon. These can be oxidatively coupled to form sulfides. It is, of course, possible, if desired, to have the amino or mercapto groups on different synthons and still form connectors. In FIG. 5C acrylate groups are shown coupled by a 2+2 cycloaddition reaction to form cyclobutane connectors.

Figure 5D:
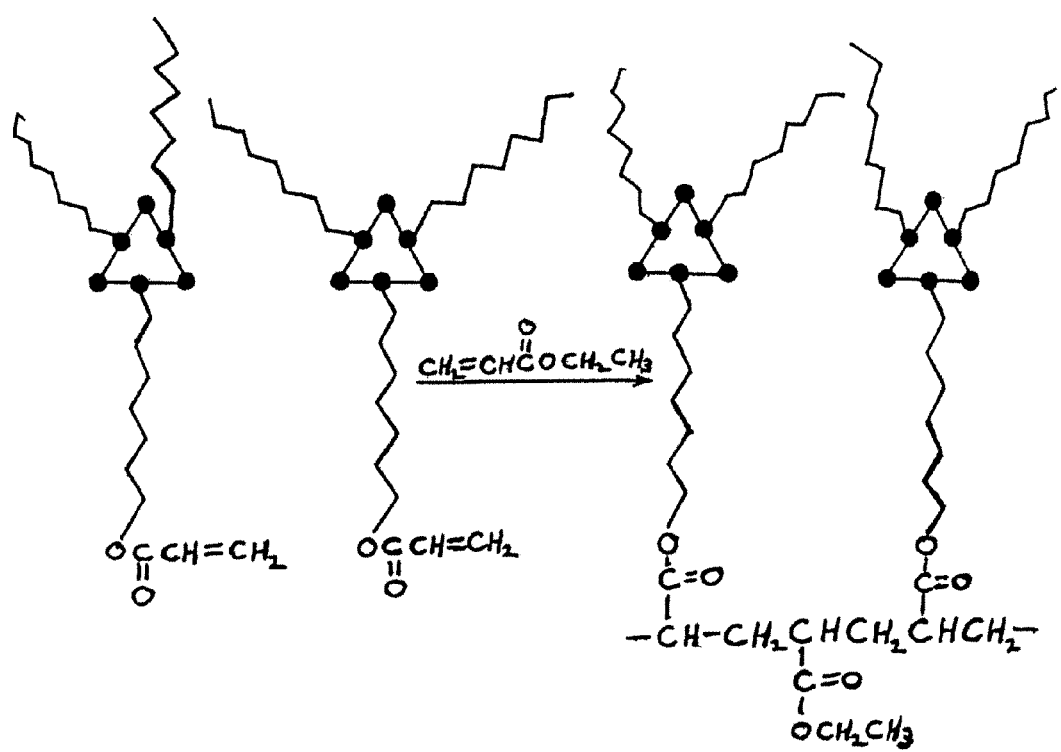
FIG. 5D shows a copolymeric connector formed by the reaction of acrylate functional groups isolated from the synthons by seven methylene spacers with external ethyl acrylate.

As indicated above, connector-forming functional groups may be separated from the modules by spacers just as linkers could be. However, connector functional groups may be separated from the ring of the module by a substantially greater distance than linkers, which usually, but not necessarily, equates to a larger number of spacer groups, particularly if the spacers are small moieties such as methylene (—CH$_2$—) groups. For example, in FIG. 5D, acrylate groups, which are separated from the body of the module by 7 methylene groups, may have initially been used as hydrophilic groups for the formation of a Langmuir film, are reacted with added acrylate to form a polyacrylate connector.

Numerous other functional groups and reactions that could be used to form connectors will become apparent to those skilled in the art based on the disclosures of this invention.

A two-dimensional, close-packed planar array of modules bonded to one another by connectors to form a cohesive one module thick sheet is referred to herein as a nanomembrane.

Applications

The modules of the present invention each contain a pore. In a presently preferred embodiment of this invention, the pores are nanopores, that is, they have a diameter between 0.5 and approximately 100 nm. The simplest application would be one involving size exclusion separations. By appropriate selection of synthons, number of synthons in each module and linkers, pores, and more specifically nanopores, of virtually any size can be created. Such filters would be useful in such applications as ion separation, gas separation, small molecule separation, water purification, sewage treatment, toxin removal, etc. Physiological uses such as filtration of bacteria, fungi, viruses and the like are also envisioned.

As mentioned previously, it is also possible to decorate the interior of the pores of the modules of this invention with functional groups that alter the environment in and around the pores. Thus, separations based on factors other than size alone will be possible using the nanomembrane filters of this invention. Chelating groups, ion traps, hydrophilicity or lipophilicity affecting groups, antibodies and histochemically active groups are but a few of the moieties that could be positioned proximate to or within the pores of the modules to affect the nature of atoms/molecules/ biological entities that can pass through the nanomembrane. Other modifications and uses of membranes of this invention will become apparent based on the disclosures herein and are within the scope of this invention.

EXAMPLES

Reagents were obtained from Aldrich Chemical Company and VWR Scientific Products. All reactions were carried out under nitrogen or argon atmosphere unless otherwise noted. Solvent extracts of aqueous solutions were dried over anhydrous Na$_2$SO$_4$. Solutions were concentrated under reduced pressure using a rotary evaporator. Thin layer chromatography (TLC) was done on analtech Silica gel GF (0.25 mm) plates or on Machery-Nagel Alugram Sil G/UV (0.20 mm) plates. Chromatograms were visualized with either UV light, phosphomolybdic acid, or KMnO$_4$. All compounds reported were homogenous by TLC unless otherwise noted. HPLC analyses were performed on a Hewlett Packard 1100 system using a reverse phase C-18 silica column. Enantiomeric excess was determined by HPLC using a reverse phase (I)-leucine silica column from Regis Technologies. All $^1$[H] and $^{13}$[C] NMR spectra were collected at 400 MHz on a Varian Mercury system. Electrospray mass spectra were obtained by Synpep Corp., or on a Thermoquest Finnegan LC-MS system.

2,6-Diformyl-4-bromophenol

Hexamethylenetetramine (73.84 g, 526 mmol) was added to TFA (240 mL) with stirring. 4-Bromophenol (22.74 g, 131 mmol) was added in one portion and the solution heated in an oilbath to 120° C. and stirred under argon for 48 h. The reaction mixture was then cooled to ambient temperature. Water (160 mL) and 50% aqueous H$_2$SO$_4$ (80 mL) were added and the solution stirred for an additional 2 h. The reaction mixture was poured into water (1600 mL) and the resulting precipitate collected on a Büchner funnel. The precipitate was dissolved in ethyl acetate (EtOAc) and the solution was dried over MgSO$_4$. The solution was filtered and the solvent removed on a rotary evaporator. Purification by column chromatography on silica gel (400 g) using a gradient of 15-40% ethyl acetate in hexanes resulted in a isolation of the product as a yellow solid (18.0 g, 60%).

$^1$H NMR (400 MHz, CDCl$_3$) δ 11.54 (s, 1H, OH), 10.19 (s, 2H, CHO), 8.08 (s, 2H, ArH).

2,6-Diformyl-4-(dodecyn-1-yl)phenol 2,6-Diformyl-4-bromophenol (2.50 g, 10.9 mmol), 1-dodecyne (2.00 g, 12.0 mmol), CuI (65 mg, 0.33 mmol), and bis(triphenylphosphine)palladium)II)dichloride were suspended in degassed acetonitrile (MeCN) (5 mL) and degassed benzene (1 mL). The yellow suspension was sparged with argon for 30 min and degassed Et$_3$N (1 mL) was added. The resulting brown suspension was sealed in a pressure vial, warmed to 80° C. and held there for 12 h. The mixture was then partitioned between EtOAc and KHSO$_4$ solution. The organic layer was separated, washed with brine, dried MgSO$_4$) and concentrated under reduced pressure. The dark yellow oil was purified by column chromatography on silica gel (25% Et$_2$O in hexanes) to give 1.56 g (46%) of the title compound.

$^1$H NMR (400 MHz, CDCl$_3$) δ 11.64 (s, 1H, OH), 10.19 (s, 2H, CHO), 7.97 (s, 2H, ArH), 2.39 (t, 2H, J=7.2 Hz, propargylic), 1.59 (m, 3H, aliphatic), 1.43, (m, 2H, aliphatic), 1.28 (m, 11H, aliphatic), 0.88 (t, 3H, J=7.0 Hz, CH$_3$).

$^{13}$C NMR (400 MHz, CDCl$_3$) δ 192.5, 162.4, 140.3, 122.8, 116.7, 91.4, 77.5, 31.9, 29.6, 29.5, 29.3, 29.1, 28.9, 28.5, 22.7, 19.2, 14.1.

MS (FAB): Calcd. for C$_{20}$H$_{27}$O$_3$ 315.1960; found 315.1958 [M+H]$^+$.

2,6-Diformyl-4-(dodecen-1-yl)phenol 2,6-Diformyl-4-bromophenol (1.00 g, 4.37 mmol), 1-dodecene (4.8 mL, 21.7 mmol), 1.40 g tetrabutylammonium bromide (4.34 mmol), 0.50 g NaHCO$_3$ (5.95 mmol), 1.00 g LiCl (23.6 mmol) and 0.100 g palladium diacetate (Pd(OAc)$_2$) (0.45 mmol) were combined in 30 mL degassed anhydrous dimethylformamide (DMF). The mixture was sparged with argon for 10 min and then sealed in a pressure vial which was warmed to 82° C. and held for 40 h. The crude reaction mixture was partitioned between CH$_2$Cl$_2$ and 0.1 M HCl solution. The organic layer was washed with 0.1 M HCl (2×), brine (2×), and saturated aqueous NaHCO$_3$ (2×), dried over MgSO$_4$ and concentrated under reduced pressure. The dark yellow oil was purified by column chromatography on silica gel (25% hexanes in Et$_2$O) to give 0.700 g (51%) of the title compound as primarily the Z isomer.

$^1$H NMR (400 MHz, CDCl$_3$) δ 11.50 (s, 1H, OH), 10.21 (s, 2H, CHO), 7.95 (s, 2H, ArH), 6.38 (d, 1H, vinyl), 6.25 (m, 1H, vinyl), 2.21 (m, 2H, allylic), 1.30-1.61 (m, 16H, aliphatic), 0.95 (t, 3H, J=7.0 Hz, CH$_3$).

MS (FAB): Calcd. for C$_{20}$H$_{27}$O$_3$ 315.20; found 315.35 [M−H]$^−$.

(1R,6S)-6-Methoxycarbonyl-3-cyclohexene-1-carboxylic Acid (S1-2)

S1-1 (15.0 g, 75.7 mmol) was suspended in pH 7 phosphate buffer (950 mL). Pig liver esterase (2909 units) was added, and the mixture stirred at ambient temperature for 72 h with the pH maintained at 7 by addition of 2M NaOH. The reaction mixture was washed with ethyl acetate (200 mL), acidified to pH 2 with 2M HCl, and extracted with ethyl acetate (3×200 mL). The extracts were combined, dried, and evaporated to afford 13.8 g (99%) of S1-2.

$^1$H NMR: (CDCl$_3$) δ 2.32 (dt, 2H, 2$_{ax}$- and 5$_{ax}$-H's), 2.55 (dt, 2H, 2eq- and 5eq-H's), 3.00 (m, 2H, 1- and 6-H's), 3.62 (s, 3H, CO$_2$Me), 5.61 (m, 2H, 3- and 4-H's).

Methyl (1S, 6R)-6-Benzyloxycarbonylaminocyclo-hex-3-enecarboxylate (S1-3)

S1-2 (10.0 g, 54.3 mmol) was dissolved in benzene (100 mL) under N2. Triethylamine (13.2 g, 18.2 mL, 130.3 mmol) was added followed by DPPA (14.9 g, 11.7 mL, 54.3 mmol). The solution was refluxed for 20 h. Benzyl alcohol (5.9 g, 5.6 mL, 54.3 mmol) was added and reflux continued for 20 h. The solution was diluted with EtOAc (200 mL), washed with saturated aqueous NaHCO$_3$ (2×50 mL), water (20 mL), and saturated aqueous NaCl (20 mL), dried and evaporated to give 13.7 g (87%) of S1-3.

1H NMR: (CDCl$_3$) δ 2.19 (dt, 1H, 5ax-H), 2.37 (tt, 2H, 2$_{ax}$- and 5eq-H's), 2.54 (dt, 1H, 2eq-H), 2.82 (m, 1H, 1-H), 3.65 (s, 3H, CO$_2$Me), 4.28 (m, 1H, 6-H), 5.08 (dd, 2H, CH$_2$Ar), 5.42 (d, 1H, NH), 5.62 (ddt, 2H, 3- and 4-H's), 7.35 (m, 5H, Ar H's).

(1S, 6R)-6-Benzyloxycarbonylaminocyclohex-3-enecarboxylic Acid (S1-4)

S1-3 (23.5 g, 81.3 mmol) was dissolved in MeOH (150 mL) and the solution cooled to 0° C. 2M NaOH (204 mL, 0.41 mol) was added, the mixture allowed to come to ambient temperature and then it was stirred for 48 h. The reaction mixture was diluted with water (300 mL), acidified with 2M HCl, and extracted with dichloromethane (250 mL), dried, and evaporated. The residue was recrystallized from diethyl ether to give 21.7 (97%) of S1-4.

1H NMR: (CDCl$_3$) δ 2.20 (d, 1H, 5$_{ax}$-H), 2.37 (d, 2H, 2$_{ax}$- and 5eq-H's), 2.54 (d, 1H, 2eq-H), 2.90 (br s, 1H, 1-H), 4.24 (br s, 1H, 6-H), 5.08 (dd, 2H, CH$_2$Ar), 5.48 (d, 1H, NH), 5.62 (dd, 2H, 3- and 4-H's), 7.35 (m, 5H, Ar H's).

(1S,2R,4R,5R)-2-Benzyloxycarbonylamino-4-iodo-7-oxo-6-oxabicyclo[3.2.1]octane (S1-5)

S1-4 (13.9 g, 50.5 mmol) was dissolved in dichloromethane (100 mL) under N$_2$, 0.5 M NaHCO$_3$ (300 mL), KI (50.3 g, 303.3 mmol), and iodine (25.6 g, 101 mmol) were added and the mixture stirred at ambient temperature for 72 h. The mixture was diluted with dichloromethane (50 mL) and the organic phase separated. The organic phase was washed with saturated aqueous Na$_2$S$_2$O$_3$ (2×50 mL), water (30 mL), and saturated aqueous NaCl (20 mL), dried and evaporated to afford 16.3 g (80%) of S1-5.

$^1$H NMR: (CDCl$_3$) δ 2.15 (m, 1H, 8$_{ax}$-H), 2.42 (m, 2H, 3$_{ax}$- and 8eq-H's), 2.75 (m, 2H, 1- and 3eq-H's), 4.12 (br s, 1H, 2-H), 4.41 (t, 1H, 4-H), 4.76 (dd, 1H, 5H), 4.92 (d, 1H, NH), 5.08 (dd, 2H, CH$_2$Ar), 7.35 (m, 5H, Ar H's).

(1S,2R,5R)-2-Benzyloxycarbonylamino-7-oxo-6-oxabicyclo[3.2.1]oct-3-ene (S1-6).

S1-5 (4.0 g, 10 mmol) was dissolved in benzene (50 mL) under N$_2$. 1,8-Diazabicyclo[5.4.0]undec-7-ene (DBU) (1.8 g, 12 mmol) was added and the solution refluxed for 16 h. The precipitate was filtered and the filtrate was diluted with EtOAc (200 mL). The filtrate was washed with 1M HCl (20 mL), saturated aqueous Na$_2$S$_2$O$_3$ (20 mL), water (20 mL), and saturated aqueous NaCl (20 mL), dried and evaporated to give 2.2 g (81%) S1-6.

¹H NMR: (CDCl₃) δ 2.18 (d, 1H, 8$_{ax}$-H), 2.39 (m, 1H, 8eq-H), 3.04 (t, 1H, 1-H), 4.70 (m, 1H, 5-H), 4.82 (t, 1H, 2-H), 5.15 (dd, 3H, CH₂Ar and NH), 5.76 (d, 1H, 4-H), 5.92 (m, 1H, 3-H), 7.36 (s, 5H, Ar H's).

(1S,2R,5R)-Methyl 2-Benzyloxycarbonylamino-5-hydroxycyclohex-3enecarboxylate (S1-7)

S1-6 (9.0 g, 33 mmol) was suspended in MeOH (90 mL) and cooled to 0° C. NaOMe (2.8 g, 52.7 mmol) was added and the mixture stirred for 3 h during which time a solution gradually formed. The solution was neutralized with 2M HCl, diluted with saturated aqueous NaCl (200 mL), and extracted with dichloromethane (2×100 mL). The extracts were combined, washed with water (20 mL) and saturated aqueous NaCl (20 ml), dried, and evaporated. The residue was flash chromatographed (silica gel (250 g), 50:50 hexane/EtOAc) to give 8.5 g (85%) of S1-7.

¹H NMR: (CDCl₃) δ 1.90 (m, 1H, 6ax H), 2.09 (m, 1H, 6$_{eq}$-H), 2.81 (m, 1H, 1-H), 3.55 (s, 3H, CO₂Me), 4.15 (m, 1H, 5-H), 4.48 (t, 1H, 2-H), 5.02 (dd, 2H, CH₂Ar), 5.32 (d, 1H, NH), 5.64 (dt, 1H, 4-H), 5.82 (dt, 1H, 3-H), 7.28 (s, 5H, Ar H's).

(1S,2R,5S)-Methyl 2-Benzyloxycarbonylamino-5-t-butoxycarbonylaminocyclohex-3-enecarboxylate (S1-8).

S1-7 (7.9 g, 25.9 mmol) was dissolved in dichloromethane (150 mL) and cooled to 0° C. under N₂. Triethylamine (6.3 g, 8.7 mL, 62.1 mmol) and methanesulfonyl chloride (7.1 g, 62.1 mmol) were added and the mixture stirred at 0° C. for 2 h. (n-Bu)₄NN₃ (14.7 g, 51.7 mmol) in dichloromethane (50 mL) was added and stirring continued at 0° C. for 3 h followed by 15 h at ambient temperature. The mixture was cooled to 0° C. and P(n-Bu)₃ (15.7 g, 19.3 mL, 77.7 mmol) and water (1 mL) were added and the mixture stirred at ambient temperature for 24 h. Di-tert-butyl dicarbonate (17.0 g, 77.7 mmol) was added and stirring continued for 24 h. The solvent was removed, the residue dissolved in 2:1 hexane/EtOAc (100 mL), the solution filtered, and evaporated. The residue was flash chromatographed (silica gel (240 g), 67:33 hexane/EtOAc) to give 5.9 g (56%) of S1-8.

¹H NMR: (CDCl₃) δ 1.40 (s, 9H, Boc H's), 1.88 (m, 1H, 6ax-H), 2.21 (m, 1H, 6$_{eq}$-H), 2.95 (m, 1H, 1-H), 3.60 (s, 3H, CO₂Me), 4.15 (d, 1H, Boc NH), 4.50 (m, 2H, 2- and 5-H's), 5.02 (s, 2H, CH₂Ar), 5.38 (d, 1H, Z NH), 5.65 (m, 2H, 3- and 4-H's), 7.30 (s, 5H, Ar H's).

(1R,2R,5S)-Methyl 2-Benzyloxycarbonylamino-5-t-butoxycarbonylaminocyclohex-3-enecarboxylate (S1-9)

S1-8 (1.1 g, 2.7 mmol) was suspended in MeOH (50 mL). NaOMe (0.73 g, 13.6 mmol) was added and the mixture refluxed for 18 h after which 0.5 M NH₄Cl(50 mL) was added and the resulting precipitate collected. The filtrate was evaporated and the residue triturated with water (25 mL). The insoluble portion was collected and combined with the original precipitate to give 0.85 g (77%) of S1-9.

1H NMR: (CDCl₃) δ 1.38 (s, 9H, Boc H's), 1.66 (m, 1H, 6$_{ax}$-H), 2.22 (d, 1H, 6$_{eq}$-H), 2.58 (t, 1H, 1-H), 3.59 (3, 3H, CO₂Me), 4.22 (br s, 1H, Boc NH), 4.50 (m, 2H, 2- and 5-H's), 4.75 (d, 1H, Z NH), 5.02 (s, 2H, CH₂Ar), 5.62 (s, 2H, 3- and 4-H's), 7.30 (s, 5H, Ar H's).

(1R,2R,5S)-2-Benzyloxycarbonylamino-5-t-butoxycarbonylaminocyclohex-3-enecarboxylic Acid (S1-10)

S1-9 (0.85 g, 2.1 mmol) was suspended in 50:50 MeOH/dichloromethane (5 mL) and cooled to 0° C. under N₂ after which 2M NaOH (2.0 mL) was added and the mixture stirred at ambient temperature for 16 h. The mixture was acidified with 2M HCl upon which a white precipitate formed. The precipitate was collected, washed with water and hexane, and dried to give 0.74 g (90%) of S1-10.

¹H NMR: (CD₃OD) δ 1.42 (s, 9H, Boc H's), 1.66 (m, 1H, 6$_{ax}$-H), 2.22 (d, 1H, 6$_{eq}$-H), 2.65 (t, 1H, 1-H), 4.18 (m, 1H, 5-H), 4.45 (m, 1H, 5-H), 5.04 (s, 2H, CH₂Ar), 5.58 (m, 2H, 3- and 4-H's), 7.35 (s, 5H, Ar H's).

(1R,2R,5S)-2-Benzyloxycarbonylamino-5-t-butoxycarbonylamino-1-(2-trimethylsilyl)ethoxycarbonylaminocyclohex-3-ene (S1-11)

S1-10 (3.1 g, 7.9 mmol) was dissolved in THF (30 mL) under N₂ and cooled to 0° C. Triethylamine (1.6 g, 2.2 mL, 15.9 mmol) was added followed by ethyl chloroformate (1.3 g, 1.5 mL, 11.8 mmol). The mixture was stirred at 0° C. for 1 h. A solution of NaN₃ (1.3 g, 19.7 mmol) in water (10 mL) was added and stirring at 0° C. was continued for 2 h. The reaction mixture was partitioned between EtOAc (50 mL) and water (50 mL). The organic phase was separated, dried, and evaporated. The residue was dissolved in benzene (50 mL) and refluxed for 2 h. 2-Trimethylsilylethanol (1.0 g, 1.2 mL, 8.7 mmol) was added and reflux continued for 3 h. The reaction mixture was diluted with EtOAc (200 mL), washed with saturated aqueous NaHCO₃ (50 mL), water (20 mL), and saturated aqueous NaCl (20 mL), dried and evaporated. The residue was flash chromatographed (silica gel (100 g), 67:33 hexane/EtOAc) to give 3.1 g (77%) of S1-11.

¹H NMR: (CDCl₃) δ-0.02 (s, 9H, TMS), 0.90 (t, 3H, CH₂TMS), 1.40 (s, 9H, Boc H's), 2.38 (m, 1H, 6$_{eq}$-H), 362 (m, 1H, 1-H), 4.08 (m, 2H, OCH₂CH₂TMS), 4.18 (m, 1H), 4.38 (m, 1H), 4.62 (m, 1H), 5.07 (dd, 2H, CH₂Ar), 5.18 (m, 1H), 5.26 (m, 1H), 5.58 (d, 1H, olefinic H), 5.64 (d, 2H, olefinic H), 7.30 (s, 5, Ar H's).

(1R,2R,5S)-2-Benzyloxycarbonylamino-1,5-diaminocyclohex-3-ene (S1-12)

S1-11 (2.5 g, 4.9 mmol) was added to TFA (10 mL) and the solution stirred at ambient temperature for 16 h after which the solution was evaporated. The residue was dissolved in water (20 mL), basified to pH 14 with KOH and extracted with dichloromethane (3×50 mL). The extracts were combined, washed with water (20 mL), dried and evaporated to give 1.1 g (85%) of S1-12.

¹H NMR: (CDCl₃) δ 1.30 (m, 1H, 6$_{ax}$-H), 2.15 (br d, 1H, 6$_{eq}$-H), 268 (m, 1H, 1-H), 3.42 (br s, 1H, 5-H), 3.95 (m, 1H, 2-H), 4.85 (d, 1H, Z NH), 5.08 (t, 2H, CH₂Ar), 5.45 (d, 1H, 4-H), 5.62 (d, 1H, 3-H), 7.32 (s, 5H, Ar H's). ESCI MS m/e 262 M+1.

Di-(l)-menthyl bicyclo[2.2.1]hept-5-ene-7-anti-(trimethylsilyl)-2-endo-3-exo-dicarboxylate (S4-26)

To a solution of S4-25 (6.09 g, 0.0155 mol) in toluene (100 mL) was added diethylaluminum chloride (8.6 mL of a 1.8 M solution in toluene) at −78° C. under nitrogen and the mixture was stirred for 1 hour. To the resulting orange solution was added S2-14 (7.00 g, 0.0466 mol) dropwise as a −78° C. solution in toluene (10 mL). The solution was kept at −78° C.

for 2 hours, followed by slow warming to room temperature overnight. The aluminum reagent was quenched with a saturated solution of ammonium chloride (50 mL). The aqueous layer was separated and extracted with methylene chloride (100 mL) which was subsequently dried over magnesium sulfate. Evaporation of the solvent left a yellow solid that was purified by column chromatography (10% ethyl acetate/hexanes) to give S4-26 as a white solid (7.19 g, 0.0136 mol, 87% yield).

$^1$H NMR: (CDCl$_3$) δ -0.09 (s, 9H, SiMe$_3$), 0.74-1.95 (multiplets, 36H, menthol), 2.72 (d, 1H, α-menthyl carbonyl CH), 3.19 (bs, 1H, bridgehead CH), 3.30 (bs, 1H, bridgehead CH), 3.40 (t, 1H, α-menthyl carbonyl CH), 4.48 (d of t, 1H, α-menthyl ester CH), 4.71 (d of t, 1H, α-menthyl ester CH), 5.92 (d of d, 1H, CH=CH), 6.19 (d of d, 1H, CH=CH), 5-exo-Bromo-3-exo-(I)-menthylcarboxybicyclo[2.2.1]heptane-7-anti(trimethylsilyl)-2,6-carbolactone (S4-27)

A solution of bromine (3.61 g, 0.0226 mol) in methylene chloride (20 mL) was added to a stirring solution of S4-26 (4.00 g, 0.00754 mol) in methylene chloride (80 mL). Stirring was continued at room temperature overnight. The solution was treated with 5% sodium thiosulfate (150 mL), and the organic layer separated and dried over magnesium sulfate. The solvent was evaporated at reduced pressure, and the crude product purified by column chromatography (5% ethyl acetate/hexanes) to give S4-27 as a white solid (3.53 g, 0.00754 mol, 99% yield).

$^1$H NMR: (CDCl$_3$) δ -0.19 (s, 9H, SiMe$_3$), 0.74-1.91 (multiplets, 18H, menthol), 2.82 (d, 1H, α-lactone carbonyl CH), 3.14 (bs, 1H, lactone bridgehead CH), 3.19 (d of d, 1H, bridgehead CH), 3.29 (t, 1H, α-menthyl carbonyl CH), 3.80 (d, 1H, α-lactone ester), 4.74 (d of t, 1H, α-menthyl ester CH), 4.94 (d, 1H, bromo CH).

Bicyclo[2.2.1]hept-5-ene-7-syn-(hydroxy)-2-exo methyl-3-endo-(I)-menthyl dicarboxylate (S4-28)

S4-27 (3.00 g, 0.00638 mol) was dissolved in anhydrous methanol (150 mL), silver nitrate (5.40 g, 0.0318 mol) added and the suspension refluxed for 3 days. The mixture was cooled, filtered through Celite and the solvent evaporated to give an oily residue. Purification by column chromatography gave S4-28 as a light yellow oil (1.72 g, 0.00491 mol, 77% yield).

$^1$H NMR: (CDCl$_3$) δ 0.75-2.02 (multiplets, 18H, menthol), 2.83 (d, 1H, α-menthyl carbonyl CH), 3.03 (bs, 1H, bridgehead CH), 3.14 (bs, 1H, bridgehead CH), 3.53 (t, 1H, α-methyl carbonyl CH), 3.76 (s, 3H, CH$_3$), 4.62 (d of t, 1H, α-menthyl ester CH), 5.87 (d of d, 1H, CH=CH), 6.23 (d of d, 1H, CH=CH).

2-exo-Methyl-3-endo-(I)-menthylbicyclo[2.2.1]hept-5-ene-7-syn-(benzyloxy) dicarboxylate (S4-29)

Benzyl bromide (1.20 g, 0.0070 mol) and silver oxide (1.62 g, 0.0070 mol) were added to a stirring solution of S4-28 (0.490 g, 0.00140 mol) in DMF (25 mL). The suspension was stirred overnight and then diluted with ethyl acetate (100 mL). The solution was washed repeatedly with water followed by 1 N lithium chloride. The organic layer was separated and dried with magnesium sulfate. The solvent was evaporated under reduced pressure and the crude product was purified by column chromatography on silica gel to give S4-29 as an oil (0.220 g, 0.000500 mol, 36% yield).

$^1$H NMR: (CDCl$_3$) δ 0.74-2.08 (multiplets, 18H, menthol), 2.83 (d, 1H, α-menthyl carbonyl CH), 3.18 (bs, 1H, bridgehead CH), 3.44 (bs, 1H, bridgehead CH), 3.52 (t, 1H, bridge CH), 3.57 (s, 3H, CH$_3$), 3.68 (t, 1H, α-methyl carbonyl CH), 4.42 (d of d, 2H, benzyl-CH$_2$), 4.61 (d of t, 1H, α-menthyl ester CH), 5.89 (d of d, 1H, CH=CH), 6.22 (d of d, 1H, CH=CH), 7.25-7.38 (m, 5H, C$_6$H$_5$).

Bicyclo[2.2.1]hept-5-ene-7-syn-(benzyloxy)-2-exo-carboxy-3-endo-(I)-menthyl carboxylate (S4-30)

S4-29 (0.220 g, 0.00050 mol) was added to a mixture of tetrahydrofuran (1.5 mL), water (0.5 mL), and methanol (0.5 mL). Potassium hydroxide (0.036 g, 0.00065 mol) was added and the solution stirred at room temperature overnight. The solvent was evaporated under reduced pressure and the residue purified by column chromatography (10% ethyl acetate/hexanes) to give S4-30 (0.050 g, 0.00012 mol, 23% yield).

$^1$H NMR: (CDCl$_3$) δ 0.73-2.01 (multiplets, 18H, menthol), 2.85 (d, 1H, α-menthyl carbonyl CH), 3.18 (bs, 1H, bridgehead CH), 3.98 (bs, 1H, bridgehead CH), 3.53 (bs, 1H, bridge CH), 3.66 (t, 1H, α-methyl carbonyl CH), 4.44 (d of d, 2H, benzyl —CH$_2$—, 4.63 (d of t, 1H, α-menthyl ester CH), 5.90 (d of d, 1H, CH=CH), 6.23 (d of d, 1H, CH=CH), 7.25-7.38 (m, 5H, C$_6$H$_5$).

Mass Spec: calculated for C$_{26}$H$_{34}$O$_5$ 426.24; found 425.4 (M−1) and 851.3 (2M−1).

Bicyclo[2.2.1]hept-5-ene-7-syn-(benzyloxy)-2-exo-(trimethylsilylethoxycarbonyl)-amino-3-endo-(I)-menthyl Carboxylate (S4-31)

To a solution of S4-30 in benzene is added triethylamine and diphenylphosphoryl azide. The solution is refluxed for 24 hours then cooled to room temperature. Trimethylsilylethanol is added, and the solution refluxed for an additional 48 hours. The benzene solution is partitioned between ethyl acetate and 1 M sodium bicarbonate. The organic layers are combined, washed with 1 M sodium bicarbonate and dried over sodium sulfate. The solvent is evaporated under reduced pressure to give the crude Curtius reaction product.

Bicyclo[2.2.1]heptane-7-syn-(benzyloxy)-2-exo-(trimethylsilylethoxycarbonyl)amino-3-endo-(I)-menthyl-5-exo-methyl-6-exo-methyl tricarboxylate (S4-32)

S4-31, dry copper(II) chloride, 10% Pd/C, and dry methanol are added to a flask with vigorous stirring. After degassing, the flask is charged with carbon monoxide to a pressure just above 1 atm., which is maintained for 72 hours. The solids are filtered and the residue worked up in the usual way to afford the biscarbonylation product.

Bicyclo[2.2.1]heptane-7-syn-(benzyloxy)-2-exo-(trimethylsilylethoxycarbonyl)-amino-3-endo-(I)-menthylcarbox-5-exo-6-exo-dicarboxylic Anhydride (S4-33)

A mixture of S4-32, formic acid, and a catalytic amount of p-toluenesulfonic acid is stirred at 90° C. overnight. Acetic anhydride is added and the reaction mixture refluxed for 6 hours. Removal of the solvents and washing with ether gives the desired anhydride.

Bicyclo[2.2.1]heptane-7-syn-(benzyloxy)-2-exo-(trimethylsilylethoxycarbonyl)-amino-3-endo-(1)-menthyl-6-exo-carboxy-5-exo-methyl Dicarboxylate (S4-33)

To a solution of S4-32 in equal amounts of toluene and carbon tetrachloride is added quinidine. The suspension is cooled to −65° C. and stirred for 1 hour. Three equivalents of methanol are slowly added over 30 minutes. The suspension is stirred at −65° C. for 4 days followed by removal of the solvents under reduced pressure. The resulting white solid is partitioned between ethyl acetate and 2M HCl. The quinine is recovered from the acid layer and S4-33 obtained from the organic layer.

Bicyclo[2.2.1]heptane-7-syn-(benzyloxy)-2-exo-(trimethylsilylethoxycarbonyl)-amino-3-endo-(I)-menthyl-6-exo-(trimethylsilylethoxycarbonyl)amino-5-exo-methyl Dicarboxylate (S4-35)

To a solution of S4-34 in benzene is added triethylamine and diphenylphosphoryl azide. The solution is refluxed for 24 hours. After cooling to room temperature, 2-trimethylsilylethanol is added and the solution refluxed for 48 hours. The benzene solution is partitioned between ethyl acetate and 1 M sodium bicarbonate. The organic layers are combined, washed with 1 M sodium bicarbonate, and dried over sodium sulfate. The solvent is evaporated under reduced pressure to give the crude Curtius reaction product.

endo-Bicyclo[2.2.1]hept-5-ene-2-benzylcarboxylate-3-carboxylic Acid (S5-37)

Compound S3-19 (4.00 g, 0.0244 mol) and quinidine (8.63 g, 0.0266 mol) were suspended in equal amounts of toluene (50 mL) and carbon tetrachloride (50 mL). The suspension was cooled to −55° C. after which benzyl alcohol (7.90 g, 0.0732 mol) was added over 15 minutes. The reaction mixture became homogenous after 3 hours and was stirred at −55° C. for an additional 96 hours. After removal of the solvents, the residue was partitioned between ethyl acetate (300 mL) and 2M hydrochloric acid (100 mL). The organic layer was washed with water (2×50 mL) and saturated aqueous sodium chloride (1×50 mL). Drying over magnesium sulfate and evaporation of the solvent gave S5-37 (4.17 g, 0.0153 mol, 63% yield).
$^1$H NMR: (CDCl$_3$) δ 1.33 (d, 1H, bridge CH$_2$), 1.48 (d of t, 1H, bridge CH$_2$), 3.18 (bs, 1H, bridgehead CH), 3.21 (bs, 1H, bridgehead CH), 3.33 (t, 2H, α-acid CH), 4.98 (d of d, 2H, CH$_2$Ph), 6.22 (d of d, 1H, CH=CH), 6.29 (d of d, 1H, CH=CH), 7.30 (m, 5H, C$_6$H$_5$).

2-endo-Benzylcarboxy-6-exo-iodobicyclo[2.2.1]heptane-3,5-carbolactone (S5-38)

S5-37 (4.10 g, 0.0151 mol) was dissolved in 0.5 M sodium bicarbonate solution (120 mL) and cooled to 0° C. Potassium iodide (15.0 g, 0.090 mol) and iodine (7.66 g, 0.030 mol) were added followed by methylene chloride (40 mL). The solution was stirred at room temperature overnight. After dilution with methylene chloride (100 mL), sodium thiosulfate was added to quench the excess iodine. The organic layer was separated and washed with water (100 mL) and sodium chloride solution (100 mL). Drying over magnesium sulfate and evaporation of the solvent gave S5-38 (5.44 g, 0.0137 mol, 91% yield).
$^1$H NMR: (CDCl$_3$) δ 1.86 (d of q, 1H, bridge —CH$_2$—), 2.47 (d of t, 1H, bridge —CH$_2$—), 2.83 (d of d, 1H, α-lactone carbonyl CH), 2.93 (bs, 1H, lactone bridge-head CH), 3.12 (d of d, 1H, α-benzyl ester CH), 3.29 (m, 1H, bridgehead CH), 4.63 (d, 1H, α-lactone ester CH), 5.14 (d of d, 2H, CH$_2$Ph), 5.19 (d, 1H, iodo CH), 7.38 (m, 5H, C$_6$H$_5$).

2-endo-Benzylcarboxy-bicyclo[2.2.1]heptane-3,5-carbolactone (S5-39)

S5-38 (0.30 g, 0.75 mmol) was placed in DMSO under N2, NaBH$_4$ (85 mg, 2.25 mmol) added and the solution stirred at 85° C. for 2 h. The mixture was cooled, diluted with water (50 mL) and extracted with dichloromethane (3×20 mL). The extracts were combined, washed with water (4×15 mL) and saturated aqueous NaCl (10 mL), dried, and evaporated to give 0.14 g (68%) of S5-39.

5-endo-hydroxybicyclo[2.2.1]heptane-2-endobenzyl-3-endo-methyl Dicarboxylate (S5-40)

Compound S5-39 is dissolved in methanol and sodium methoxide added with stirring. Removal of the solvent gives S5-40.

Bicyclo[2.2.1]heptane-2-endo-benzyl-3-endo-methyl-5-exo-(t-butoxycarbonyl)-amino Dicarboxylate (S5-41)

In a one-pot reaction S5-40 is converted to the corresponding mesylate with methanesulfonyl chloride, sodium azide added to displace the mesylate to give exo-azide, which is followed by reduction with tributyl phosphine to give the free amine, which is protected as the t-Boc derivative to give S5-41.

Bicyclo[2.2.1]heptane-2-endo-carboxy-3-exo-methyl-5-exo-(t-butoxycarbonyl)-amino Carboxylate (S5-42)

The benzyl ether protecting group is removed by catalytic hydrogenolysis of S5-41 with 10% Pd/C in methanol at room temperature for 6 hours. Filtration of the catalyst and removal of the solvent yields crude S5-42.

Bicyclo[2.2.1]heptane-2-endo-carboxy-3-exo-methyl-5-exo-(t-butoxycarbonyl)-amino Carboxylate (S5-43)

Sodium is dissolved in methanol to generate sodium methoxide. S5-42 is added and the mixture stirred at 62° C. for 16 hr. The mixture is cooled and acetic acid added with cooling to neutralize the excess sodium methoxide. The mixture is diluted with water and extracted with ethyl acetate. The extract is dried and evaporated to give S5-43.

Bicyclo[2.2.1]heptane-2-endo-benzyl-3-exo-methyl-5-exo-(t-butoxycarbonyl)-amino Dicarboxylate (S5-44)

Compound S5-43 is reacted with benzyl bromide and cesium carbonate in tetrahydrofuran at room temperature to give benzyl ester S5-44, which is isolated by acid work-up of the crude reaction mixture.

Bicyclo[2.2.1]heptane-2-endo-benzyl-3-exo-carboxy-5-exo-(t-butoxycarbonyl)-amino late (S5-45)

Compound S5-44 is dissolved in methanol and cooled to 0° C. under $N_2$. 2M NaOH (2 equivalents) is added dropwise, the mixture allowed to come to ambient temperature and is stirred for 5 h. The solution is diluted with water, acidified with 2M HCI and extracted with ethyl acetate. The extract is washed with water, saturated aqueous NaCI, dried evaporated to give S5-45.

Bicyclo[2.2.1]heptane-2-endo-benzyl-3-exo-(trimethylsilylethoxycarbonyl)-amino-5-exo-(t-butoxycarbonyl)amino-5-exo-(t-butoxycarbonl)amino carboxylate (S5-46)

To a solution of S5-45 in benzene is added triethylamine and diphenylphosphoryl azide. The solution is refluxed for 24 hours and then cooled to room temperature. Trimethylsilylethanol is added and the solution refluxed for 48 hours. The solution is partitioned between ethyl acetate and 1 M sodium bicarbonate. The organic layer is washed with 1M sodium bicarbonate and dried over sodium sulfate. The solvent is evaporated under reduced pressure to give crude Curtius product S5-46.

endo-Bicyclo[2.2.1]hept-5-ene-2-(4-methoxy)benzylcarboxylate-3-carboxylic Acid (S6-48)

Compound S3-19 and quinidine are suspended in equal amounts of toluene and carbon tetrachloride and cooled to −55° C. p-Methoxybenzyl alcohol is added over 15 minutes and the solution stirred at −55° C. for 96 hours. After removal of the solvents, the residue is partitioned between ethyl acetate and 2 M hydrochloric acid. The organic layer is washed with water and saturated aqueous sodium chloride. Drying over magnesium sulfate and removal of the solvent gives S6-48.

endo-Bicyclo[2.2.1]hept-5-ene-2-(4-methoxy)benzyl-3-(trimethylsilylethoxycarbonyl)-amino Carboxylate (S6-49)

To a solution of S6-48 in benzene is added triethylamine and diphenylphosphoryl azide. The solution is refluxed for 24 hours, cooled to room temperature, trimethylsilylethanol is added, and the solution is refluxed for an additional 48 hours. The benzene solution is partitioned between ethyl acetate and 1M sodium bicarbonate. The organic layers are combined, washed with 1M sodium bicarbonate, and dried with sodium sulfate. The solvent is evaporated under reduced pressure to give crude Curtius product S6-49.

Bicyclo[2.2.1]heptane-2-endo-(4-methoxy)benzyl-3-endo(trimethylsilylethoxycarbonyl)-amino-5-exo-methyl-6-exo-methyl Tricarboxylate (S6-50)

S6-49, copper(II) chloride, 10% Pd/C, and dry methanol are added to a flask with vigorous stirring. After degassing the suspension, the flask is charged with carbon monoxide to a pressure just above 1 atm. The pressure of carbon monoxide is maintained over 72 hours. The solids are filtered off, and the crude reaction mixture worked up in the usual way to afford S6-50.

Bicyclo[2.2.1]heptane-2-endo-(4-methoxy)benzyl-3-endo(trimethylsilylethoxycarbonyl)-amino-5-exo-6-exodicarboxylic Anhydride (S6-51)

S6-50, formic acid, and a catalytic amount of p-toluenesulfonic acid is heated at 90° C. overnight. Acetic anhydride is added to the reaction mixture, and it is refluxed for an additional 6 hours. Removal of the solvents and washing with ether affords S6-51.

Bicycle[2.2.1]heptane-2-endo-(4-methoxy)benzyl-3-endo-(trimethylsilylethoxycarbonyl)-amino-5-exo-carboxy-6-exo-methyl Dicarboxylate (S6-52)

To a solution of S6-51 in equal amounts of toluene and carbon tetrachloride is added quinine. The suspension is cooled to −65° C. and stirred for 1 hour. Three equivalents of methanol are added slowly over 30 minutes. The suspension is stirred at −65° C. for 4 days followed by removal of the solvents. The resulting white solid is partitioned between ethyl acetate and 2 M HCI, with S6-52 worked up from the organic layer.

Bicyclo[2.2.1]heptane-2-endo-(4methoxy)benzyl 3endo-(trimethylsilylethoxycarbonyl)amino-5exo-trimethylsilylethoxycarbonyl)amino-exo-methyl Dicarboxylate (S653)

To a solution of S6-52 in benzene is added triethylamine and diphenylphosphoryl azide. The solution is refluxed for 24 hours then cooled to room temperature. 2-Trimethylsilylethanol is added, and the solution is refluxed for an additional 48 hours. The benzene solution is partitioned between ethyl acetate and 1 M sodium bicarbonate. The organic layers are combined, washed with 1 M sodium bicarbonate, and dried with sodium sulfate. The solvent is evaporated under reduced pressure to give S6-53.

Bicyclo[2.2.1]heptane-2-exo-(4methoxy)benzyl-3endo-(trimethylsilylethoxycarbonyl)amino-5exo-(trimethylsilylethoxycarbonyl)amino-6-endo-methyl Dicarboxylate (S6-54)

To a solution of S6-53 in tetrahydrofuran is carefully added potassium tertbutoxide. The basic solution is refluxed for 24 hours followed by addition of acetic acid. Standard extraction methods give the double epimerized product S6-54.

Preparation of Hexamer:

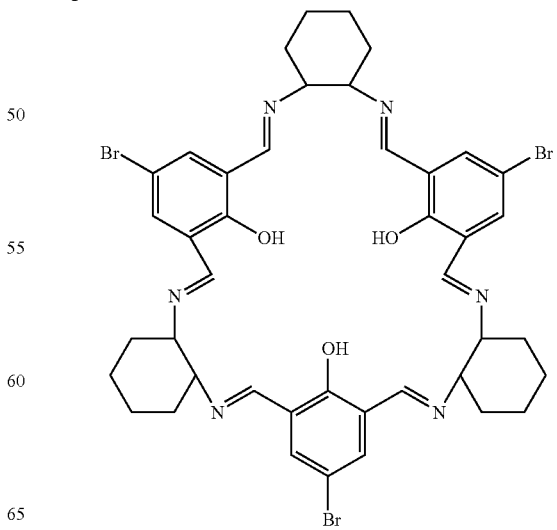

To 0.300 g R,R-1,2-trans-diaminocyclohexane (2.63 mmol) in 5 mL CH$_2$Cl$_2$ at 0° C. was added 0.600 g of 2,6-diformyl4-bromophenol (2.62 mmol) in 5 mL of CH$_2$Cl$_2$. The yellow solution was allowed to warm to room temperature and stirred for 48 hours. The reaction solution was decanted, and added to 150 mL of methanol. After standing for 30 minutes, the yellow precipitate was collected, washed with methanol, and air-dried (0.580 mg; 72% yield).

$^1$H NMR (400 MHz, CDCl$_3$) δ 14.31 (s, 3H, OH), 8.58 (s, 3H, CH=N), 8.19 (s, 3H, CH=N), 7.88 (d, 3H, J=2.0 Hz, ArH), 7.27 (d, 3H, J=2.0 Hz, ArH), 3.30-3.42 (m, 6H, CH$_2$—CH—N), 1.41-1.90 (m, 24H, aliphatic).

MS (FAB): Calcd for C$_{42}$H$_{46}$N$_6$O$_3$Br$_3$ 923.115; found 923.3 [M+H]$^+$.

Preparation of Hexamer:

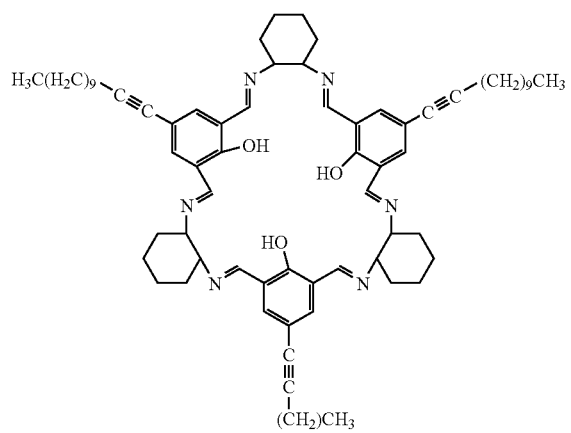

To 0.300 g R,R-1,2-trans-diaminocyclohexane (2.63 mmol) in 6 mL CH$_2$Cl$_2$ at 0° C. was added 0.826 g of 2,6-diformyl4-(1-dodec-1-yne)phenol (2.63 mmol) in 6 mL of CH$_2$Cl$_2$. The orange solution was stirred at 0° C. for 1 hour and then allowed to warm to room temperature after which stirring was continued for 16 hours. The reaction solution was decanted and added to 150 mL of methanol. A sticky yellow solid was obtained after decanting the methanol solution. Chromatographic cleanup of the residue gave a yellow powder.

$^1$H NMR (400 MHz, CDCl$_3$) δ 14.32 (s, 3H, OH), 8.62 (s, 3H, CH=N), 8.18 (s, 3H, CH=N), 7.84 (d, 3H, J=2.0 Hz, ArH), 7.20 (d, 3H, J=2.0 Hz, ArH), 3.30-3.42 (m, 6H, CH$_2$—CH—N), 2.25 (t, 6H, J=7.2 Hz, propargylic), 1.20-1.83 (m, 72H, aliphatic), 0.85 (t, 9H, J=7.0 Hz, CH$_3$).

$^{13}$C NMR (400 MHz, CDCl$_3$) δ 163.4, 161.8, 155.7, 136.9, 132.7, 123.9, 119.0, 113.9, 88.7, 79.7, 75.5, 73.2, 33.6, 33.3, 32.2, 29.8, 29.7, 29.6, 29.4, 29.2, 29.1, 24.6, 24.5, 22.9, 19.6, 14.4.

MS (FAB): Calcd for C$_{78}$H$_{109}$N$_6$O$_3$ 1177.856; found: 1177.8 [M+H]$^+$.

Preparation of Hexamer:

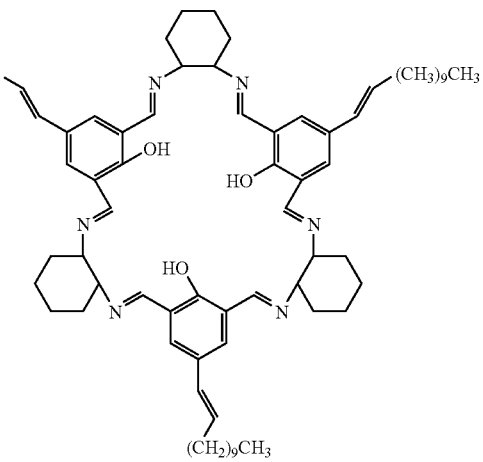

To 0.240 g of 2,6-diformyl-4-(1-dodecene)phenol (0.76 mmol) in 10 mL of benzene was added a 10 mL benzene solution of R,R-1,2-trans-diaminocyclohexane (0.087 g, 0.76 mmol). The solution was stirred at room temperature for 48 hours shielded from the light. The orange solution was taken to dryness and chromatographed (silica, 50/50 acetone/Et$_2$O) to give a yellow sticky solid (33% yield).

$^1$H NMR (400 MHz, CDCl$_3$) δ 14.12 (s, 3H, OH), 8.62 (s, 3H, CH=N), 8.40 (s, 3H, CH=N), 7.82 (d, 3H, J=2.0 Hz, ArH), 7.28 (d, 3H, J=2.0 Hz, ArH), 6.22 (d, 3H, vinyl), 6.05 (d, 3H, vinyl), 3.30-3.42 (m, 6H, CH$_2$—CH—N), 1.04-1.98 (m, 87H, aliphatic.

MS (FAB): Calcd for C$_{78}$H$_{115}$N$_6$O$_3$ 1183.90; found: 1184.6 [M+H]$^+$.

Preparation of Tetramer and Hexamer:

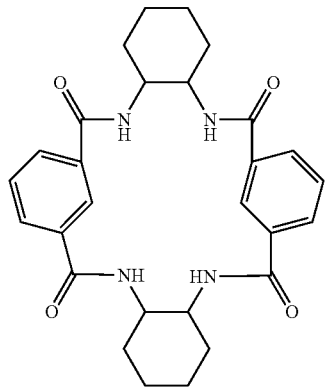

-continued

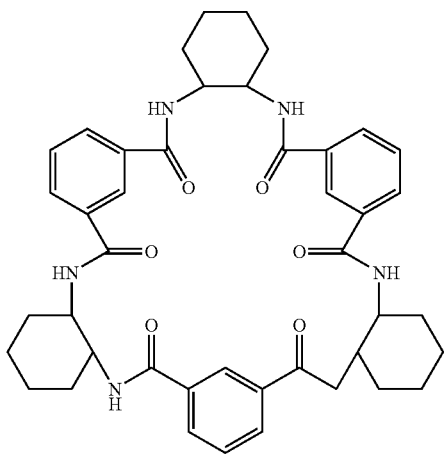

Triethylamine (0.50 mL, 3.59 mmol) and R,R-1,2-transdiaminocyclohexane (0.190 g, 1.66 mmol) were combined in 150 mL EtOAc and purged with $N_2$ for 5 minutes. To this solution was added 0.331 g isophthalolyl chloride (1.66 mmol) dissolved in 100 mL EtOAc dropwise over six hours. The solution was filtered and the filtrate taken to dryness. TLC (5% methanol/$CH_2Cl2$) shows the product mixture to be primarily composed of two macrocycles. Chromatographic separation (silica, 5% methanol/$CH_2Cl_2$) gave the above tetramer (0.020 g, 5% yield) and hexamer (about 10%).

Tetramer:

$^1$H NMR (400 MHz, $CDCl_3$) δ 7.82 (s, 1H), 7.60 (br s, 2H), 7.45 (br s, 2H), 7.18 (br s, 1H), 3.90 (br s, 2H), 2.22 (d, 2H), 1.85 (m, 4H), 1.41 (m, 4H).

MS (ESI): Calcd for $C_{28}H_{33}N_4O_4$ 489.25; found 489.4 $[M+H]^+$.

Hexamer:

MS (ESI): Calcd for $C_{42}H_{49}N_6O_6$ 733.37; found 733.5 $[M+H]^+$.

CONCLUSION

Thus, it will be appreciated that the present invention provides versatile synthons and modules for use in the formation of nanomembranes. Methods for the preparation of the synthons, for the linking together of synthons to form modules, in particular modules in which the ring of synthons define a pore in the resulting module, and for the connection of modules to form nanomembranes are also provided. The nanomembranes are useful, among other things, as filters.

Although certain embodiments and examples have been used to describe the present invention, it will be apparent to those skilled in the art that changes in the embodiments and examples shown may be made without departing from the scope and spirit of this invention.

Other embodiments are within the following claims.

What is claimed:

1. An amphiphilic compound of the structure:

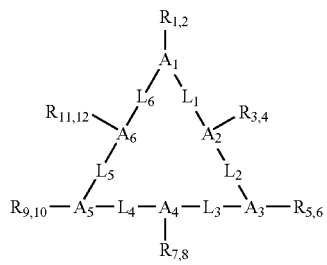

wherein:

$A_1$-$A_6$ are synthons, wherein $A_1$, $A_3$ and $A_5$ are each benzene and $A_2$, $A_4$, and $A_6$ are each cyclohexane;

$L_1$-$L_6$ are linkers, wherein $L_1$-$L_6$ are each independently selected from —C(O)O—, —OC(O)—, —C(O)NH—, —NHC(O)—, —$CH_2$NH—, —NH$CH_2$—, —N═CH—, and —CH═N—;

$R_1$, $R_3$, $R_5$, $R_7$, $R_9$ and $R_{11}$ are each independently selected from hydrogen and a lipophilic group selected from -(8C-28C)alkyl, —O(8C-28C)alkyl, —NH(8C-28C)alkyl, —OC(O)-(8C-28C)alkyl, —C(O)O—(8C-28C)alkyl, —NHC(O)-(8C-28C)alkyl, —C(O)NH-(8C-28C)alkyl, —CH═CH-(8C-28C)alkyl and —C≡C-(8C-28C)alkyl, wherein the carbon atoms of the (8C-28C)alkyl group may be interrupted by one or more —S—, double bond, triple bond or —SiR'R"— groups, wherein each carbon atom is optionally substituted with one or more fluorine atoms, and wherein R' and R" independently comprise (1C-18C)alkyl;

wherein each lipophilic group selected may be the same or different from each other; and wherein at least one of $R_1$, $R_3$, $R_5$, $R_7$, $R_9$ and $R_{11}$ is a lipophilic group; and $R_2$, $R_4$, $R_6$, $R_8$, $R_{10}$ and $R_{12}$ are each independently selected from hydrogen and a hydrophilic group;

wherein each hydrophilic group selected may be the same or different from each other; and wherein at least one of $R_1$, $R_3$, $R_5$, $R_7$, $R_9$ and $R_{11}$ is a hydrophilic group.

2. The amphiphilic compound of claim 1, wherein the hydrophilic group is selected from —OH, —$OCH_3$, —$NH_2$, —C≡N, —$NO_2$, —$^+$NRR'R"A$^-$, —$SO_3^-M^+$, —$OPO_2^{2-}M^+$, —OC(O)CH═$CH_2$, —$SO_2NH_2$, —$SO_2$NRR', —OP(O)(O$CH_2CH_2N^+$RR'R")O$^-$, —C(O)OH, —C(O)O$^-M^+$, guanidinium, aminate, pyridinium, —C(O)O$CH_3$, —C(O)O$CH_2CH_3$, —C(O)OCH═$CH_2$, —O($CH_2$)$_y$C(O)$NH_2$, —O($CH_2CH_2$O)zR''' and

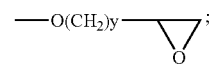

wherein R, R' and R" are independently selected from hydrogen and (1C-4C)alkyl, R''' is selected from hydrogen, $CH_2$C(O)OH and —$CH_2$C(O)$NH_2$, A$^-$ is a suitable anion, M$^+$ is a suitable cation, y is 1-6 and z is 1-50.

3. The amphiphilic compound of claim 1, wherein $L_1$-$L_6$ are the same.

4. An amphiphilic compound of the structure:

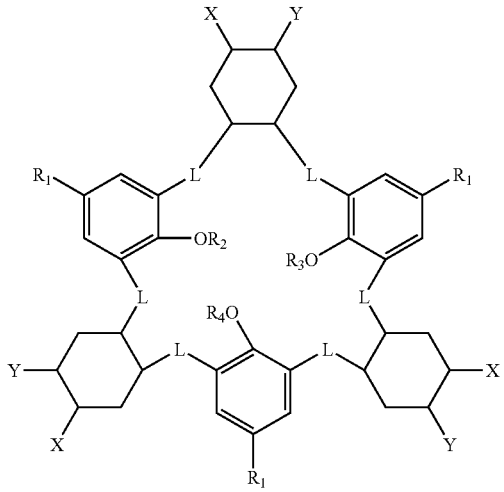

wherein:
X and Y are both —SH or —NH$_2$; or,
X is selected from —C(O)OH, —C(O)OCH$_3$, and —C(O)R, and Y is —NH$_2$; wherein R represents a leaving group readily displaced by a nucleophile;
R$_1$, is selected from —CH$_2$(10C-18C)alkyl, —CH═CH-(10C-18C)alkyl, —C≡C-(10C-18C)alkyl, —OC(O)-(10C-18C)alkyl, —C(O)O-(10C-18C)alkyl, —NHC(O)-(10C-18C)alkyl, —C(O)NH-(10C-18C)alkyl and —O-(10C-18C)alkyl;
R$_2$, R$_3$ and R$_4$ are independently selected from hydrogen, C(O)(CH$_2$)$_2$C(O)OCH$_3$, —C(O)CH═CH$_2$,

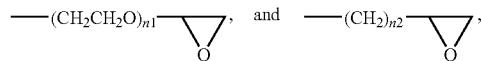

wherein n1 is 1-50 and n2 is 1-4, provided that at least one of R$_2$, R$_3$ or R$_4$ must be other than hydrogen; and,
L is selected from —C(O)O—, —OC(O)—, —C(O)NH—, —NHC(O)—, —CH$_2$NH—, —NHCH$_2$—, —N═CH—, and —CH═N—.

5. The amphiphilic compound of claim 4, wherein L is selected from —C(O)O—, —C(O)NH—, —CH$_2$NH— and —CH═N—.

6. An amphiphilic compound of the chemical structure:

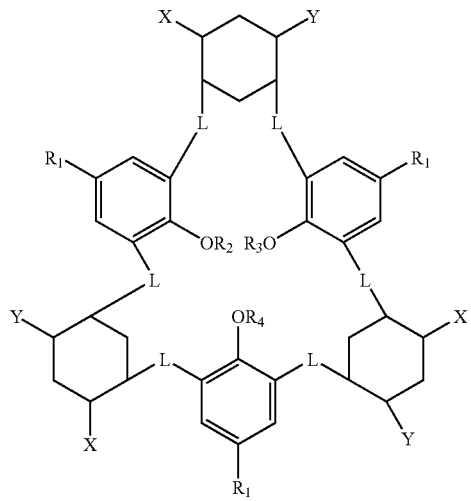

wherein:
X and Y are independently selected from hydrogen,

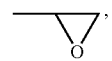

—OC(O)CH═CH$_2$, —SH and —NH$_2$; or,
X is —C(O)OH, —C(O)OCH$_3$, and —C(O)R, and
Y is selected from —NH$_2$, —OH and SH, wherein R represents a leaving group readily displaced by a nucleophile;
R$_1$ is selected from —CH$_2$-(10C-18C)alkyl, CH═CH-(10C-18C)alkyl, —C≡C-(10C-18C)alkyl, —OC(O)-(10C-18C)alkyl, —C(O)O(10C-18C)alkyl, —NHC(O)-(10C-18C)alkyl, —C(O)NH-(10C-18C)alkyl and —O-(10C-18C)alkyl;
R$_2$, R$_3$ and R$_4$ are independently selected from hydrogen, —C(O)(CH$_2$)$_2$C(O)OCH$_3$, —C(O)CH═CH$_2$,

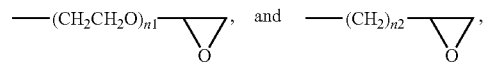

wherein n1 is 1-50 and n2 is 1-4, provided that at least one of R$_2$, R$_3$ or R$_4$ is not hydrogen; and
L is selected from —C(O)O—, —OC(O)—, —C(O)NH—, —NHC(O)—, —CH$_2$NH—, —NHCH$_2$—, —N═CH—, and —CH═N—.

7. The amphiphilic compound of claim 6, wherein L is selected from —C(O)O—, —C(O)NH—, —CH$_2$NH— and —CH═N—.

8. A method of synthesizing an amphiphilic compound of claim 1, comprising:
providing synthons A$_1$, A$_3$ and A$_5$, wherein each synthon comprises two functional groups that may be the same or different;
providing synthons A$_2$, A$_4$ and A$_6$ wherein each synthon comprises two functional groups that may be the same or different;
wherein the functional groups of synthons A$_1$, A$_3$ and A$_5$ can react with the functional groups of synthons A$_2$, A$_4$ and A$_6$;
contacting synthons A$_1$, A$_3$ and A$_5$ with A$_2$, A$_4$ and A$_6$ in a solvent; and, isolating the amphiphilic module.

9. The method of claim 8, wherein contacting synthons A$_1$, A$_3$, and A$_5$ with synthons A$_2$, A$_4$, and A$_6$, further comprises contacting synthons A$_1$, A$_3$, and A$_5$ with at least one reagent that catalyzes the reaction of the functional groups of synthons A$_1$, A$_3$ and A$_5$ with the functional groups of synthons A$_2$, A$_4$ and A$_6$.

10. A method for synthesizing an amphiphilic compound of claim 1 comprising:
placing synthon A$_1$, comprising a functional group in a solvent;
adding synthon A$_2$, comprising a functional group that reacts with the functional group of synthon A$_1$ to form a dimer;
adding synthon A$_3$, which comprises a functional group that reacts with the functional group of synthon A$_2$, to form a trimer;
adding synthon A$_4$, which comprises a functional group that reacts with the functional group of synthon A$_3$ to form a tetramer;

adding synthon $A_5$, which comprises a functional group that reacts with the functional group of synthon $A_4$ to form a pentamer; and adding synthon $A_6$, which comprises a functional group that reacts with the functional groups of synthons $A_5$ and $A_1$ to form a cyclic hexamer.

11. The method of claim 10, wherein at least one reagent is added to catalyze the reaction of a functional group of synthon $A_1$, $A_3$ or $A_5$ with a functional group of the next synthon $A_2$, $A_4$ or $A_6$ being added, or the at least one reagent first reacts with a functional group of synthon $A_1$, $A_3$ or $A_5$ to form an intermediate which then reacts with a functional group of the next synthon $A_2$, $A_4$ or $A_6$ being added to form a bond.

* * * * *